United States Patent
Tai et al.

(10) Patent No.: US 9,970,945 B2
(45) Date of Patent: May 15, 2018

(54) COMPOSITIONS, METHODS, AND ASSAYS USING PROTEO-LIPOSOME-TRANSFECTED OOCYTES FOR ANALYZING THE STRUCTURE, FUNCTION, AND ACTIVITY OF MEMBRANE PROTEINS

(71) Applicant: Georgia State University Research Foundation, Inc., Atlanta, GA (US)

(72) Inventors: Phang-Cheng Tai, Atlanta, GA (US); Ying-hsin Hsieh, Atlanta, GA (US); Chun Jiang, Marietta, GA (US); Jenny Jie Yang, Marietta, GA (US); Juan Zou, Atlanta, GA (US)

(73) Assignee: Georgia State University Research Foundtion, Inc., Atlanta, GA (US)

( * ) Notice: Subject to any disclaimer, the term of this patent is extended or adjusted under 35 U.S.C. 154(b) by 0 days. days.

(21) Appl. No.: 14/896,437

(22) PCT Filed: Jun. 9, 2014

(86) PCT No.: PCT/US2014/041585
§ 371 (c)(1),
(2) Date: Dec. 7, 2015

(87) PCT Pub. No.: WO2014/197905
PCT Pub. Date: Dec. 11, 2014

(65) Prior Publication Data
US 2016/0116485 A1    Apr. 28, 2016

Related U.S. Application Data

(60) Provisional application No. 61/832,288, filed on Jun. 7, 2013.

(51) Int. Cl.
*G01N 33/68* (2006.01)
*G01N 33/50* (2006.01)
*G01N 33/92* (2006.01)
*G01N 33/487* (2006.01)

(52) U.S. Cl.
CPC ... *G01N 33/6872* (2013.01); *G01N 33/48728* (2013.01); *G01N 33/5044* (2013.01); *G01N 33/92* (2013.01)

(58) Field of Classification Search
CPC ......... G01N 33/48728; G01N 33/5044; G01N 33/6872; G01N 33/92
See application file for complete search history.

(56) References Cited

U.S. PATENT DOCUMENTS

| | | | |
|---|---|---|---|
| 6,488,829 B1 * | 12/2002 | Schroeder ........ | G01N 33/48728 204/403.01 |
| 6,551,796 B1 * | 4/2003 | Abramson ........... | C07K 14/705 435/252.3 |
| 9,206,456 B2 * | 12/2015 | Lenormand ...... | A61K 47/48238 |
| 2015/0152077 A1 * | 6/2015 | Wang ................... | C07D 401/14 514/387 |

FOREIGN PATENT DOCUMENTS

WO    2013184755    12/2013

OTHER PUBLICATIONS

Li J, et al. Asian Journal of Pharmaceutical Sciences. 10(2):81-98. Apr. 2015. Available online at—https://doi.org/10.1016/j.ajps.2014.09.004.*
D\Avanzo, et al., "Differential lipid dependence of the function of bacterial sodium channels", PLoS ONE, 8(4): e61216 (2013).
Hsieh, et al., "SecA Alone Can Promote Protein Translocation and Ion Channel Activity", J. Biol. Chem. 286:44702-9 (2011).
Hsieh, et al., "Reconstitution of functionally efficient SecA-dependent protein-conducting channels: Transformation of low-affinity SecA-liposome channels to high-affinity SecA-SecYEG-SecDF YajC channels", Biochem Biophys Res Comm., 431:388-92 (2013).
Ivorra, et al., "Protein orientation affects the efficiency of functional protein transplantation into the xenopus oocyte membrane", J Membrane Biol., 185(2):117-27 (2002).
Jarecki, et al., "Function of Shaker potassium channels produced by cell-free translation upon injection into Xenopus oocytes", Sci Reports, 3:1040:1-7 (2013).
Lagree, et al., "A yeast recombinant aquaporin mutant that is not expressed or mistargeted in Xenopus oocyte can be functionally analyzed in reconstituted proteoliposomes", J Biological chem., 272(20):12422-6 (1998).
Le Caherec, et al., "Incorporation of proteins into (Xenopus) oocytes by proteoliposome microinjection: functional characterization of a novel aquaporin", J Cell Sci., 109 ( Pt 6):1285-1295 (1996).
Lin, et al., "Electrophysiological studies in Xenopus oocytes for the opening of *Escherichia coli* SecA-dependent protein-conducting channels", J Membr Biol., 214:103-13 (2007).

(Continued)

*Primary Examiner* — Robert S Landsman
(74) *Attorney, Agent, or Firm* — Pabst Patent Group LLP

(57) ABSTRACT

Compositions and methods for reconstituting a protein of interest in the plasma membrane of a *Xenopus* oocyte are disclosed. The method generally includes combining a pre-assembled membrane protein or proteins with a liposome to prepare a proteo-liposome. The proteo-liposome can have a specific composition of lipids. The proteo-liposome is incubated for sufficient time and under conditions suitable for the protein of interest to fold, associate with, or insert into the liposome's lipid bilayer. In some embodiments, the protein or proteins assemble into a protein channel or complex on or in the proteo-liposome's membrane. The treated oocytes can be used to determine the structure, function, or activity of the membrane protein of interest, the effect of a lipid microenvironment on a membrane protein of interest, or to identify compounds that modulate the function or activity of the membrane protein of interest.

36 Claims, 17 Drawing Sheets

(56) References Cited

OTHER PUBLICATIONS

Lin, et al., "*Escherichia coli* membranes depleted of SecYEG elicit SecA-dependent ion-channel activity but lose signal peptide specificity", J Membrane Biol., 245(11):747-57 (2012).
Maroto, et al., "TRPC1 forms the stretch-activated cation channel in vertebrate cells", Nature Cell Biol., 7(2):179-85 (2005).
Matsuoka, et al.,"Giant patch and macro patch", Springer Protocols handbooks—Patch Clamp Techniques: From Beginning to Advanced Protocols, Humana Press vol. 9, Chapter 14:207-18 (2012).
Miledi, et al., "Expression of functional neurotransmitter receptors in Xenopus oocytes after injection of human brain membranes", PNAS, 99:13238-42 (2002).
Pandhare, et al., "595-Pos Board B381 Injection of Affinity-Purified . . . for Functional Studies using Electrophysiology", Biophysical J, 102(3): Suppl 1:118A (2012).
Philips, et al., "Emerging roles for lipids in shaping membrane-protein function", Nature, 459:379-85 (2009).
Peng, et al., "Single channel study of deltamethrin interactions with wild-type and mutated rat Na(V)1.2 sodium channels expressed in Xenopus oocytes", Neurotoxicology, 30(3):358-67 (2009).
Siefani, et al., "Cut-open oocyte voltage-clamp technique", Methods Enzymol., 293:300-18 (1998).
Yang, et al., "SecE-depleted membranes of *Escherichia coli* are active. SecE is not obligatorily required for the in vitro translocation of certain protein precursors", J. Biol. Chem., 272:13660-5 (1997a).
Yang, et al., "Differential translocation of protein precursors across SecY-deficient membranes of *Escherichia coli*: SecY is not obligatorily required for translocation of certain secretory proteins in vitro", J. Bacteriol., 179 7386-93 (1997b).
You, et al., "Phospholipids induce conformational changes of SecA to form membrane-specific domains: AFM structures and implication on protein-conducting channels", PloS One, 8(8):e72560 (2013).
Yukutake, et al., "Mercury chloride decreases the water permeability of aquaporin-4-reconstituted proteoliposomes", Biol Cell, 100:355-63 (2008).
International Search Report and Written Opinion for corresponding PCT application PCT/US2014/041585 dated Nov. 21, 2014.
Cabelli, et al., "Characterization of membrane-associated and soluble states of SecA protein from wild-type and SecA51(TS) mutant strains of *Escherichia coli*", J Biol Chem., 266:24420-7 (1991).
Celis, "Microinjection of somatic cells with micropipettes: comparison with other transfer techniques", Biochem J, 223:281-91 (1984).
Chen and Tai, "ATP is essential for protein translocation into *Escherichia coli* membrane vesicles", PNAS, 82:4384-8 (1985).
Chen, et al., "Identification and characterization of protease-resistant SecA fragments: secA has two membrane-integral forms", J Bacteriol., 180:527-37 (1998).
Chen, et al., "A significant fraction of functional SecA is permanently embedded in the membrane. SecA cycling on and off the membrane is not essential during protein translocation", J Biol Chem., 271: 29698-706 (1996).
Chen, et al., "Molecular interaction and functional regulation of connexin50 gap junctions by calmodulin", Biochem J., 435:711-22 (2011).
Fiori, et al., "Permeation of calcium through purified connexin 26 hemichannels", J Biol Chem., 287:40826-34 (2012).
Gerido, et al., "Aberrant hemichannel properties of Cx26 mutations causing skin disease and deafness", Am J Physiol Cell Physiol., 293:C337-45 (2007).
Goldin, "Expressiom of ION channels in xenopus oocytes", Expression and Analysis of Recombinant Ion Channels, chapter 1:1-25, Wiley-VCH Verlag GmbH & Co. KGaA, (2006).
Gundersen, et al., "Messenger RNA from human brain induces drug- and voltage-operated channels in Xenopus oocytes", Nature, 308:421-4 (1984).
Huang, et al., "Fluorescein analogues inhibit SecA ATPase: the first sub-micromolar inhibitor of bacterial protein translocation", Chem Med Chem., 7:571-7 (2012).
Lill, et al., "The ATPase activity of SecA is regulated by acidic phospholipids, SecY, and the leader and mature domains of precursor proteins", Cell, 60:271-80 (1990).
Locke and Harris, "Connexin channels and phospholipids: association and modulation", BMC Biol., 7:52 (2009).
Miledi, et al., "Properties of acetylcholine receptors translated by cat muscle mRNA in Xenopus oocytes", EMBO J., 1:1307-12 (1982).
Oliver and Beckwith, "Identification of a new gene (secA) and gene product involved in the secretion of envelope proteins in *Escherichia coli*", J Bacteriol., 150:686-91 (1982).
Oliver, et al., "Azide-resistant mutants of *Escherichia coli* alter the SecA protein, an azide-sensitive component of the protein export machinery", PNAS, 87:8227-31 (1990).
Peracchia, "Chemical gating of gap junction channels; roles of calcium, pH and calmodulin". Biochim Biophys Acta, 1662:61-80 (2004).
Ramamurthy and Oliver, "Topology of the integral membrane form of *Escherichia coli* SecA protein reveals multiple periplasmically exposed regions and modulation by ATP binding", J Biological Chem., 272:23239-46 (1997).
Sanchez, et al., "Differentially altered Ca2+ regulation and Ca2+ permeability in Cx26 hemichannels formed by the A40V and G45E mutations that cause keratitis ichthyosis deafness syndrome", J Gen Physiol., 136:47-62 (2010).
Silhavy and Beckwith, "Isolation and characterization of mutants of *Escherichia coli* K12 affected in protein localization". Methods Enzymol., 97:11-40 (1983).
Sotkis, et al., "Calmodulin colocalizes with connexins and plays a direct role in gap junction channel gating", Cell Commun Adhes., 8:277-81 (2001).
Thornhill and Levinson, "Biosynthesis of electroplax sodium channels in Electrophorus electrocytes and Xenopus oocytes", Biochem., 26:4381-8 (1987).
Wang, et al., "Ring-like pore structures of SecA: implication for bacterial protein-conducting channels", PNAS, 100:4221-6 (2003).
Yu, et al., "Expression, purification, and characterization of Pseudomonas aeruginosa SecA", Protein Expr Purif., 50:179-84 (2006).

\* cited by examiner

A. SecAs channels

B. Liposome composition

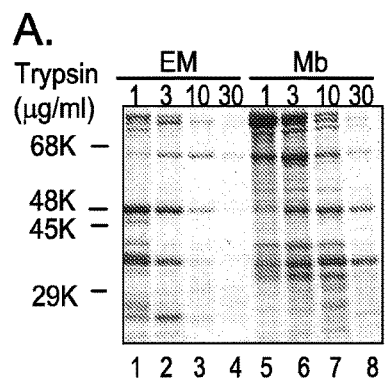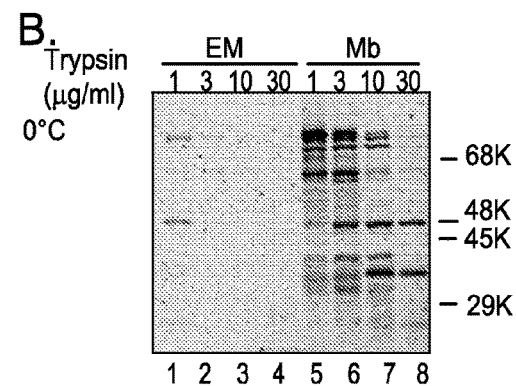
FIG. 12A
FIG. 12B
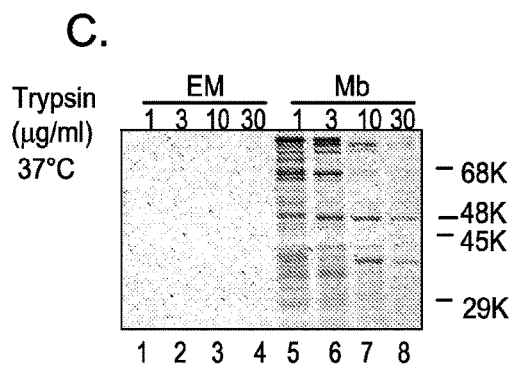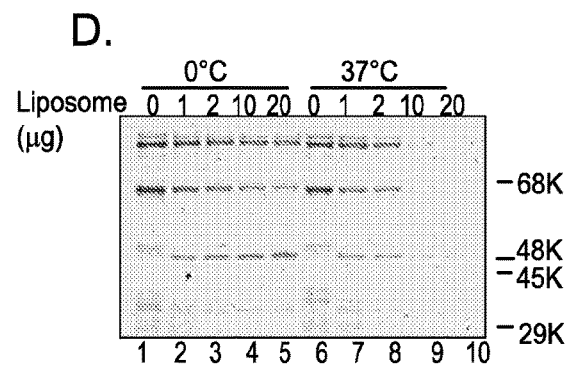
FIG. 12C
FIG. 12D

A.

B.

C.

COMPOSITIONS, METHODS, AND ASSAYS USING PROTEO-LIPOSOME-TRANSFECTED OOCYTES FOR ANALYZING THE STRUCTURE, FUNCTION, AND ACTIVITY OF MEMBRANE PROTEINS

CROSS-REFERENCE TO RELATED APPLICATIONS

This application is a 371 application of International Application No. PCT/US2014/041585, filed Jun. 9, 2015, which claims priority to U.S. Provisional Application No. 61/832,288, filed Jun. 7, 2013, by Phang-Cheng Tai, Ying-hsin Hsieh, Chun Jiang, Jenny Jie Yang and Juan Zou, all of which are incorporated herein by reference.

STATEMENT REGARDING FEDERALLY SPONSORED RESEARCH OR DEVELOPMENT

This invention was made with government support under agreement GM034766 awarded by the National Institutes of Health. The government has certain rights in the invention.

REFERENCE TO SEQUENCE LISTING

The Sequence Listing submitted Mar. 16, 2017, as a text file named "GSURF_2013-28_ST25.txt," created on Jan. 11, 2017, and having a size of 2,244 bytes is hereby incorporated by reference pursuant to 37 C.F.R. § 1.52(e)(5)."

FIELD OF THE INVENTION

The invention is in the field of membrane proteins, and compositions, methods, and assays for analyzing their structure, function, and activity.

BACKGROUND OF THE INVENTION

Membrane proteins, either alone or in complexes, carry out many important physiological functions in all cells in response to signaling and regulation. The synthesis and assembly of membrane proteins into the hydrophobic lipids phase to carry out various functions have long been intensively investigated. Many functional membrane proteins possess channel activities that could be monitored by electrophysiological methods in response to intracellular or extracellular stimuli or regulatory molecules. Oocyte injection has been widely used for monitoring membrane ion channel activity for years, and is well-known for studying channels in a controlled in vivo cellular environment. By injecting specific mRNA or cDNA into the oocytes, the target channels can be expressed and assembled in the oocyte membranes for whole cell voltage clamp recording (1, 2), patch clamp and other biochemical approaches (3).

This method is exquisitely sensitive because the channels are expressed and presented on the whole oocyte membrane surface; with the channel activity recording being based on the sum of the channel activities in the whole cell, the resulting ion current is detectable at μA levels. Additional advantages of this assay include low endogenous channel activities, large size of the oocytes, and the detection efficiency of target protein activity (4). So far it has been widely employed for analyzing characteristics and regulation of channels, domain mutations, and drug and drug resistance screening (5).

However, there are several major challenges for further application to the study of membrane proteins. First, not all target protein channels can be expressed in the oocytes, and in some cases, the mRNA or cDNA are not available, for example, in the use of clinical samples (6). Second, there is no methodology readily available for the study of complex systems with multiple, membrane protein complexes. Third, most membrane proteins, especially eukaryotic proteins, require special environments for folding, assembly, post-modification, and trafficking. The direct correlation of in vitro liposomes studies to the cellular physiological activities of these membrane proteins has not been achieved despite of the fact that tremendous effort and progress have been made for in vitro refolding and assembly of purified channel membrane proteins, using various liposome technologies. To date, it is not known whether such systems can indeed function for channel activity within an in vivo physiological cellular system. In addition, there is increasing evidence that different compositions of lipids actually modulate channel activities (7). Therefore, there remains a need for additional methods of analyzing characteristics and regulation of membrane proteins, such as channels, pumps, and receptors.

Accordingly, it is an object of the invention to provide compositions and methods for analyzing characteristics and regulation of membrane proteins, such as channels, pumps, and receptors in a physiologically relevant in vitro system.

It is also an object of the invention to provide compositions and methods for screening new compounds that bind to or act on membrane proteins.

SUMMARY OF THE INVENTION

Compositions and methods for expressing a protein of interest on the plasma membrane of an oocyte, preferably a *Xenopus* oocyte, are disclosed. The method generally includes reconstitution of a membrane protein or proteins of interest with a liposome to prepare a proteo-liposome. The proteo-liposome is incubated for sufficient time and under conditions suitable for the protein of interest to fold, assemble, and associate with, or insert into the liposome's lipid bilayer. In some embodiments, the protein or proteins assemble into a protein channel or complex on or in the proteo-liposome's membrane. The proteo-liposomes are introduced by microinjection into the oocyte. The protein or proteins of interest form functional membrane proteins on or in the membrane of the oocyte.

The protein is typically a membrane protein, for example a channel, transporter, receptor, cell adhesion molecule, enzyme, or a subunit thereof. The protein can be recombinant protein. The membrane protein or proteins can be 2 or more different proteins that together form a complex or a channel. For example the protein or proteins of interest can form a homo- or hetero-oligomers. If the membrane protein or proteins form a complex, the complex is allowed to form on or in the membrane of the proteo-liposome prior to introduction of the proteo-liposome into the oocyte.

The liposome can be formed by lipids from bacterial or eukaryotic cell membrane extracts or one or more types of synthetic lipids. The lipids of the liposome can include phosphatidic acid (phosphatidate) (PA), cardiolipin, phosphatidylethanolamine (cephalin) (PE), phosphatidylcholine (lecithin) (PC), phosphatidylserine (PS), phosphatidylinositol (PI), phosphatidylinositol phosphate (PIP), phosphatidylinositol bisphosphate (PIP2), phosphatidylinositol triphosphate (PIP3), ceramide phosphorylcholine (sphingomyelin) (SPH), ceramide phosphorylethanolamine (sphingomyelin), (Cer-PE) ceramide phosphoryl lipid or a combination thereof.

In some embodiments, there is differential lipid dependence for the function of the membrane protein, not only in the terms of lipids' categories, but the ratio of different lipids to each other. In a specific embodiment the liposome has a lipid ratio of PC/PS of 2:1 or a ratio PE/PG of 3:1 and the protein is a connexin such as Cx26. In another specific embodiment, the liposome has a lipid ratio of PE/PC of 3:1 or PE/PG of 3:1. These lipid compositions are particularly useful when the proteins form a channel, such as an ion or protein channel. For example, the protein can be a bacterial protein such as SecA or eukaryotic protein such as Cx26.

Oocytes prepared accordingly to the disclosed methods are also disclosed. The oocytes can be used to determine the structure, function, or activity of the membrane protein of interest, the effect of a lipid microenvironment of a membrane protein of interest, or to identify compounds that modulate the function or activity of the membrane protein of interest. For example, the oocytes can be subjected to a biochemical or physiological assay such as two-electrode whole cell voltage-clamp, cut-open oocyte voltage-clamp, macropatch clamp, or single channel analysis.

In some embodiments, the protein of interest is a mutant protein, for example, a protein that has a mutation that causes or contributes to a human disease. The mutations can be compared to wildtype protein in the assays disclosed herein to determine how the mutation affects the structure, function, or activity of the protein. The mutant protein can also be subjected to screening assays to identify compounds that specifically affect the mutant protein.

BRIEF DESCRIPTION OF THE DRAWINGS

FIG. 2A is a histogram bar graph showing channel activity of various bacterial SecA-liposomes in oocytes, measured in μA. Channels with SecA from various bacteria are labeled as follows; Sa, *S. aureus* SecA1 and SecA2, Ec, *E. coli* SecA; Pa, *P. aeruginosa*; Bs, *B. subtilus*; BaSecA, *B. anthraces* SecA1, Mtb, *M. tuberculosis* SecA1; Ms, *M. smegatatis* SecA1; SpSecA, *Streptococcus pyogenes* SecA1. FIG. 2B is a histogram bar graph showing channel activity of liposomes made of various lipids. PC/PS was 2:1, PE/PC and PE/PG ratios were 3:1. n=30.

FIG. 3A is a histogram bar graph showing channel activity efficiency of SecA-liposomes in oocytes, measured in μA. Measurements are compared for SecA channels alone and complex channels with SecYEG and SecDF•YajC. BA13 is native membrane depleted of SecA. Recordings were made after 3 hours of injections. FIG. 3B is a line graph showing the time course (in hours) of channel activity of SecA-liposomes in oocytes, measured in μA. Data are shown for SecA-liposomes alone, and complexes with SecYEG or with SecYEG and SecDF•YajC. N=20-50.

FIG. 4A is a line graph showing the non-competitive inhibition kinetics of Rose Bengal in EcSecA in vitro translocation ATPase and channel activity with *E. coli* membranes. FIG. 4B is a line graph showing the non-competitive inhibition kinetics of Rose Bengal in oocyte ion channel activity with EcSecA-liposomes. FIG. 4C is a line graph showing the non-competitive inhibition kinetics of Rose Bengal in oocyte ion channel activity with PaSecA-liposomes. FIG. 4D is a line graph showing the non-competitive inhibition kinetics of Rose Bengal in oocyte ion channel activity with SaSecA1-liposomes. n=20-30.

FIG. 5A is a histogram bar graph showing channel activity efficiency of SecA-liposomes in oocytes, measured in μA. Channel activity was measured in oocytes following injection of liposomes alone or Cx26-liposomes in the oocytes with or without 5 mM EGTA, and $CaCl_2$ as indicated. Lanes 4 and 6 were with 2 mM $CaCl_2$; lane 7 with 5 mM EGTA, and lane 8 was with 5 mM EGTA and 10 mM $CaCl_2$. FIG. 5B is a line graph showing the time course of Cx26 channel expression and activity with 5 mM EGTA in oocytes, measured in μA. FIG. 5C is a line graph showing channel activity of Cx26-liposomes with 5 mM EGTA, measured in μA, in oocytes incubated with various conc. of $CaCl_2$ in the extracellular bath solution for 30 mins before recording. Insert is a line graph showing the time course of channel activity in oocytes incubated with the 10 mM $CaCl_2$ in the extracellular bath solution. FIG. 5D is a line graph showing the time course of Cx26 channel activity injected into oocytes for 30 mins. During the recording, 10 mM EGTA was added in extracellular bath solution for 4 mins, followed by adding 30 mM $CaCl_2$ in the bath solution (indicated by arrows). FIG. 5E is a histogram bar graph showing Cx26 channel activity in oocytes, measured in μA, using different liposome compositions. The PC/PS ratio is 2:1 and PE/PG ratio is 3:1. n=15-20.

FIG. 6A is a line graph showing the channel activity, measured in μA, of various quantities of SecA-liposomes (0-120 ng) in oocytes-. SecA-liposomes were injected into oocytes with ATP-Mg, proOmpA in the presence of 0.47 ng SecYEG or together with 0.53 ng SecDF_YajC and various amounts of SecA. FIG. 6B is a histogram bar graph showing the channel activity of SecA-liposomes in oocytes, measured in μA, using different quantities of liposomes, with or without additional 2 mM ATP-1 mM $MgCl_2$. FIG. 6C is a line graph showing the channel activity of SecYEG-liposomes in oocytes, measured in μA in the presence of varied amounts of SecA-liposomes/SecYEG-SecDF•YajC. Membrane only control is native BA13 membrane (SecY needed was about 16% as in the membranes). n=40.

FIG. 7A is a histogram bar graph showing the % pOmpA translocation channel activity of liposomes in the presence or absence of SecA, SecYEG and SecDF•YajC in oocytes. The translocation activity of proOmpA with membranes (M) was set as 100%. Lanes 1-7 contain 10 μg liposome and variably 10 μg SecA mixed with translocation buffer and energy source, 66 ng SecYEG, 55 ng SecDF•YajC reconstituted into SecA-liposomes mixture. Lane 8 shows translocation activity with 3.5 μg of native 773 membrane vesicles (M) containing 165 ng of SecYEG and 1 μg SecA. FIG. 7B is a line graph showing the % channel activity of various liposome compositions containing 0-10 μg SecA in oocytes. Reduced requirements of SecA for SecA-liposomes with increased SecYEG/SecDF•YajC as in 3.5 μg of 773 (Membrane) vesicles. The amounts of purified SecYEG used were 40% (66 ng) or 100% (165 ng) of the amount of SecY in membranes. n=4.

FIG. 9A is a scatter dot plot to show quantitation of relative amounts of SecY in membranes and in the purified SecYEG preparation. To determine the relative amount of purified SecYEG to membranes used for oocytes recording and translocation assays, the amount of SecY was compared by Western blot and analyzed by Bio-Rad Quantity One software. Serial amounts of membranes and purified SecYEG preparations were quantified to generate a standard curve to determine the SecY amounts in BA13 Membranes and Purified SecYEG. FIG. 9B is an image of western blot of SecY in the membrane and in the purified SecYEG preparations, with lanes corresponding to: 1) Mock, 2) *E. coli* membranes (3.5 μg) and 3-6) 0.08, 0.17, 0.51, 0.68 μg purified SecYEG, respectively. The SecYEG amount of Lane 4 was used in the translocation experiments of FIG. 7A.

FIGS. 10A and 10B are photographs of electrophoresis gels showing lanes 1-12 (indicated at bottom), each containing 10 μg SecA without (−) or with (+) liposomes, with *E. coli* lipid mixtures (EM), treated with indicated concentrations of trypsin (0.1-30 μg/ml). Molecular weight markers (protein bovine serum albumin (68-kDa), ovalbumin (45-kDa), and carbonic anhydrase (29-kDa)) are labeled (left). FIG. 10C shows two photographs of gels: 1. (upper panel) is an electrophoresis gel staining with Coomassie blue and 2. (lower panel) is the corresponding immune-blot transferred to PVDF membrane sheets and developed by immune-blotting with a specific antibody against $SecA_{665-820}$-A5 [6, 9]. Lanes 1-5 are labeled (top), each containing 10 μg SecA digested in 3 μg/ml trypsin. FIGS. 10D and 10E are photographs of electrophoresis gels showing lanes 1-12 (bottom), each containing 10 μg SecA digested as in FIG. 10A, using the mixtures of lipids indicated. EM: the mixture of *E. coli* lipid extracts, PE: L-α-Phosphatidylethanolamine; PG:1,2-Dioleoyl-sn-Glycero-3-[Phospho-rac-(1-glycerol)] CL: Cardiolipin PC: 1,2-Dioleoyl-sn-Glycero-3-Phosphocholine.

FIGS. 12A-12D. FIGS. 12A-12C are photographs electrophoresis gels showing lanes 1-8, each containing 20 μg liposomes of *E. coli* lipid mixtures and 20 μg BA13 inverted inner membrane (mb), mixed in 100 μl DTK buffer on ice with 10 μg SecA (FIG. 12A), 1 μg of [$^{35}$S] SecA (FIG. 12B), 10 μg SecA incubated at 37° C. for 15 min, chilled on ice prior to the addition of trypsin (FIG. 12C). All samples were treated with the indicated concentration of Trypsin (1-30 μg/ml). FIG. 12D is a photograph of an electrophoresis gel showing lanes 1-10 each containing 2 μg of [$^{35}$S]SecA, mixed with different amounts of liposomes, as indicated. Protein mixtures in lanes 1-5 were incubated on ice and in lanes 6-10 were incubated at 37° C. for 15 min. All samples were cooled on ice and treated with a final concentration 1 μg/ml trypsin.

FIG. 13A is a photograph of an electrophoresis gel showing lanes 1-6 each containing 1 μg [$^{35}$S] SecA in 100 μl DTK buffer, mixed with 20 μg SecYEG-depleted membrane (SecA-mb), 20 μg wildtype membrane (SecE-mb), or 20 μg SecA-depleted BA13 membrane (MC1000-mb). After pre-incubation at 37° C. for 15 min, the samples were cooled on ice and incubated for 15 mins without (lanes 1-3) or with (lanes 4-6) 30 μg/ml trypsin. FIG. 13B is a photograph of an electrophoresis gel showing lanes 1-6 containing the reactions mixtures of FIG. 13A, in the presence of 20 μg of membranes, N39, C28, BSA or Cytochrome C (lane 3) or liposomes alone (lane 6). FIG. 13C is a line graph showing the % of M48 domain fragment in each liposomal fraction, quantitated after gel electrophoresis, relative to the amount of the M48 domain obtained from mb-associated SecA, as a function of total protein (0-25 μg). Reactions were carried out as in FIG. 13B, in the presence of various amounts of N39, N53, C28, CvaA, BSA, and CCO (Cytochrome C Oxidase, which was taken as 100% at 20 μg). The amount of M48 domain from CCO was calculated from immunoblots while other amounts were calculated from autoradiograms. The data were from 2-4 sets of independent experiments, and presented as mean+SE.

FIG. 14A is a photograph of an electrophoresis gel showing lanes 1-6 each containing 1 μg [$^{35}$S] SecA in 100 μl DTK buffer, in the presence of 2 mM ATP or AMP-PNP and 4 mM Mg(OAc)2 and incubated for 15 mins with 30 μg/ml trypsin. FIG. 14B is a photograph of an electrophoresis gel showing lanes 1-4 containing Mb or N39 with EM, under the proteolytic reaction conditions of FIG. 14A at the trypsin concentrations indicated. FIG. 14C is a photograph of an electrophoresis gel showing lanes 1-10 each containing 1 μg [$^{35}$S]SecA in 100 μl DTK buffer, in the presence of 2 mM ATP or AMP-PNP and 4 mM Mg(OAc)2. The effect that integrity of the membrane has upon stability of the M48 domain was ascertained by undertaking proteolysis at different concentration of trypsin in the presence of Triton-x100 (1%) or malto-dodecylmaltoside (DM, 2%) as indicated. Reaction conditions used were similar to those defined in FIG. 14A.

FIG. 15A is a panel of photomicrographs illustrating structural variations adopted by purified SecA and a series of its truncated domains, determined by incubating with or without lipid bilayers (+/−L) prepared from *E. coli*-extracted lipid mixtures. Images N39+L and M48+L are zoomed-in images of bilayers and are not shown to scale with the other images. FIG. 15B is a schematic diagram showing potential trypsin cleavage sites of N68, and N39 and M48 in SecA, illustrated with the location of the two nucleotide binding sites, each with its attendant Walker A and B motifs (orange bars). The location of each of the potential cleavage sites in the X-ray crystal structure of SecA in either the open-state (a) or in the closed-state (b) are also shown. Potential cleavage-site 1 (609-613) is magenta, the cleavage-site forming the N39 region is red and the cleavage-site separating M48 from C10 is yellow. FIG. 15C is cartoon diagram illustrating how the SecA asymmetric dimer forms functional channels allowing protein precursors to be translocated across the cytoplasmic membrane into the periplasm. The two distinct forms of integral SecA (SecAM and SecAS) together create a structural channel, that can be observed for SecA alone using AFM and TEM (lower right frames). SecAM consists of N39, M48 and C10, and SecAS, consists of N68 with ATPase activity and C34, and appears to adopt the same conformation as SecA in its fully soluble form.

DETAILED DESCRIPTION OF THE INVENTION

Figure 1:
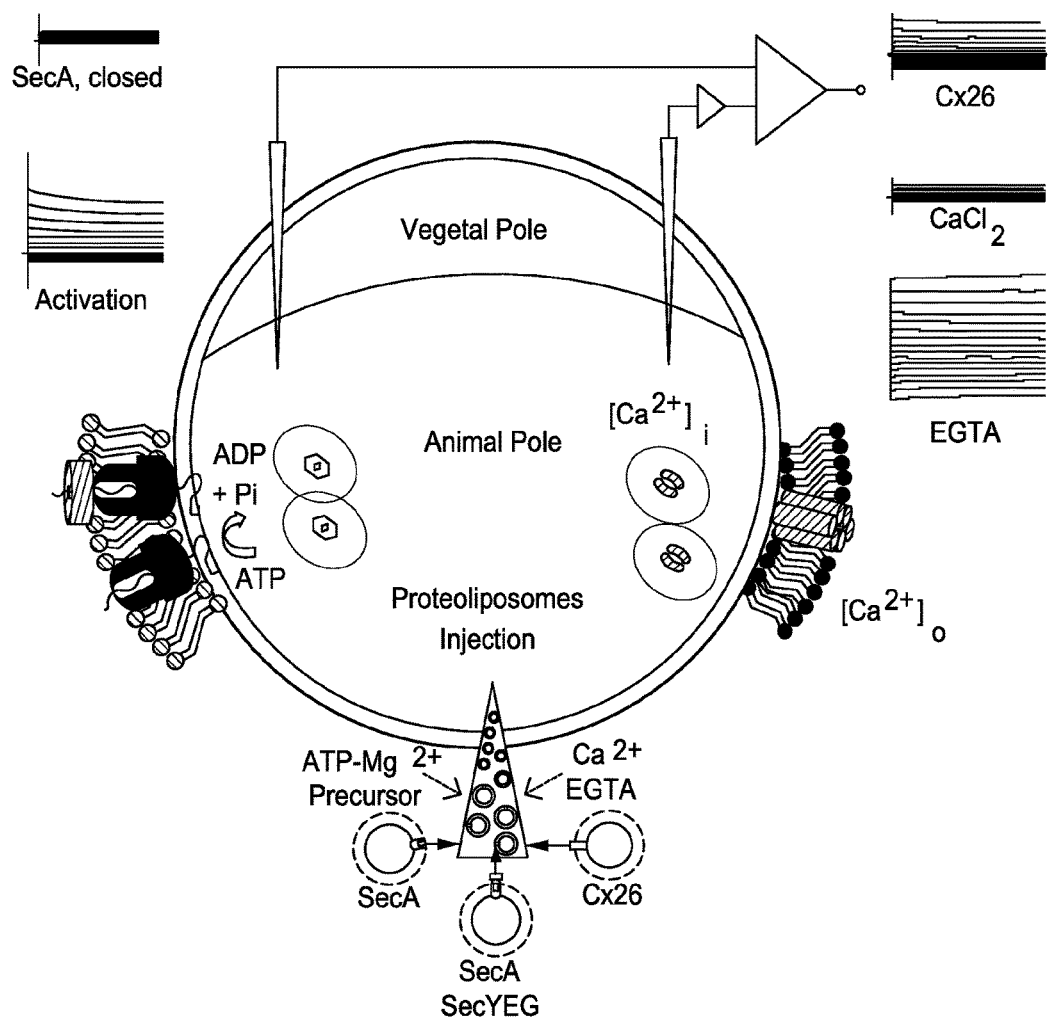
FIG. 1 is a schematic representation of ion-current recording of injected proteo-liposomes in *Xenopus* oocytes. Pre-assembled SecA-liposomes or Cx26-liposomes along with other essential components are injected into oocytes at the dark side animal pole (bottom) for detection of whole-cell channel activity. Two-electrode recording is done after 0.5-3 hours, depending on the proteo-liposomes detection efficiency. For SecA channel, the closed SecA channel is activated by precursors and ATP-$Mg^{2+}$, while Cx26 channel is regulated by $Ca^{2+}$. Graphical representation of the measured ionic flux that accompanies activation of SecA (left) and Cx26 (right) channels is provided for each group of channel activity respectively above the schematic diagram.

Disclosed are methods and compositions for assaying one or more reconstituted proteins of interest in the plasma membrane of an oocyte. The method can include combining the proteins of interest with a liposome to prepare a proteo-liposome; allowing sufficient time for the proteins of interest to fold, associate with, or insert into the liposome's lipid bilayer, and pre-assemble into one or more functional membrane proteins; introducing the proteo-liposome into the oocyte to produce a modified oocyte; and subjecting the oocyte to a biochemical or physiological assay.

Also disclosed are methods and compositions for reconstituting one or more proteins of interest in the plasma membrane of an oocyte to produce a modified oocyte. The method can include combining the proteins of interest with a liposome to prepare a proteo-liposome; allowing sufficient time for the proteins of interest to fold, associate with, or insert into the liposome's lipid bilayer, and pre-assemble into one or more functional membrane proteins; and introducing the proteo-liposome into the oocyte to produce a modified oocyte.

Also disclosed are methods and compositions for determining the structure, function, or activity of a membrane protein of interest by subjecting an oocyte modified via the disclosed methods to a biochemical or physiological assay. Also disclosed are methods and compositions for determining the effect of a lipid microenvironment of a membrane protein of interest by subjecting an oocyte modified via the disclosed methods to a biochemical or physiological assay. Also disclosed are methods and compositions for screening test compounds by subjecting an oocyte modified via the disclosed methods to a biochemical or physiological assay before and after treatment with a test compound and selecting compounds that increase or decrease the function or activity of the protein or proteins of interest.

In some embodiments, the physiological assay is selected from the group consisting of two-electrode whole cell voltage-clamp, cut-open oocyte voltage-clamp, macropatch clamp, and single channel analysis. In some embodiments, at least one of the proteins is a channel, transporter, receptor, cell adhesion molecule, enzyme, or a subunit thereof. In some embodiments, the proteins are two or more different proteins that together form a membrane complex or channel. In some embodiments, the time for the proteins of interest to fold, associate with, or insert into the liposome's lipid bilayer is sufficient to allow assembly of the complex or channel in the lipid bilayer of the proteo-liposome. In some embodiments, the proteo-liposome is introduced into the oocyte by injection. In some embodiments, at least one of the proteins is recombinant or isolated protein. In some embodiments, the liposome comprises lipids from bacterial extracts. In some embodiments, the liposome comprises one or more synthetic lipids.

In some embodiments, the liposome comprises phosphatidic acid (phosphatidate) (PA), phosphatidylethanolamine (cephalin) (PE), phosphatidylcholine (lecithin) (PC), phosphatidylserine (PS), cardiolipin, phosphatidylinositol (PI), phosphatidylinositol phosphate (PIP), phosphatidylinositol bisphosphate (PIP2), phosphatidylinositol triphosphate (PIP3), ceramide phosphorylcholine (sphingomyelin) (SPH), ceramide phosphorylethanolamine (sphingomyelin), (Cer-PE) ceramide phosphoryllipid or a combination thereof. In some embodiments, the liposome comprises a ratio of PC/PS of 2:1. In some embodiments, the liposome comprises a ratio of PE/PG of 3:1.

In some embodiments, at least one of the proteins is a connexin. In some embodiments, the connexin is Cx26. In some embodiments, the liposome comprises a ratio of PE/PC of 3:1. In some embodiments, the liposome comprises a ratio of PE/PG of 3:1.

In some embodiments, at least one of the proteins of interest forms a bacterial channel. In some embodiments, at least one of the proteins of interest is SecA.

In some embodiments, at least one of the proteins of interest forms a mammalian channel. In some embodiments, the biochemical or physiological assay determines the structure, function, or activity of at least one of the proteins of interest. In some embodiments, the biochemical or physiological assay determines the effect of a lipid microenvironment of at least one of the proteins of interest.

In some embodiments, two or more oocytes are subjected to the biochemical or physiological assay, wherein the lipid composition of the proteo-liposomes introduced in the oocytes are different. In some embodiments, the oocyte is subjected to the biochemical or physiological assay before and after treatment with a test compound, the method further comprising selecting test compounds that increase or decrease the function or activity of at least one of the proteins of interest.

In some embodiments, at least one of the proteins of interest is a mutant protein. In some embodiments, the mutation of the mutant protein is a human disease mutation.

Also disclosed are modified oocytes. In some embodiments, the oocyte is modified by combining one or more proteins of interest with a liposome to prepare a proteo-liposome; allowing sufficient time for the proteins of interest to fold, associate with, or insert into the liposome's lipid bilayer, and pre-assemble into one or more functional membrane proteins; and introducing the proteo-liposome into the oocyte to produce a modified oocyte. In some embodiments, the modified oocyte includes a functional, reconstituted mammalian or bacterial channel-forming protein. In some embodiments, the channel formed by the channel-forming protein is an ion channel. In some embodiments, the channel formed by the channel-forming protein is a protein or peptide channel. In some embodiments, the channel-forming protein is reconstituted in the lipid membrane of the oocyte.

In some embodiments, the oocyte is a *Xenopus* oocyte.

Also disclosed are proteo-liposomes comprising an ion channel-forming protein and a PC/PS ratio of 2:1 and a PE/PG ratio of 3:1.

I. Definitions

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein the term "isolated" is meant to describe a compound of interest (e.g., nucleic acids, polypeptides, etc.) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids or polypeptides are at least 60% free, preferably 75% free, and most preferably 90% free from other associated components.

As used herein, the terms "engineered" and "recombinant" cells are intended to refer to a cell into which an exogenous DNA segment or gene, such as a cDNA or gene has been introduced. Therefore, engineered cells are distinguishable from naturally occurring cells which do not contain a recombinantly introduced exogenous DNA segment or gene. Engineered cells are thus cells having a gene or genes introduced through the hand of man.

The term "reconstituted" refers to a protein that is not directly expressed in the oocyte from a nucleic acid.

The term "pre-assembly" refers to a protein associating with or incorporating into a lipid membrane, for example, a proteo-liposome. If the protein is a channel or complex, pre-assembly includes formation of the channel or complex in the lipid membrane.

II. Compositions and Methods of Preparing Treated Oocytes

Compositions and methods for reconstituting functional membrane proteins in an oocyte lipid bilayer environment are disclosed. The compositions include an oocyte, referred to herein as a "treated oocyte", which has been modified by the addition of proteo-liposome composition including lipids and one or more membrane proteins. As discussed in more detail below, the proteo-liposome is prepared prior to addition to the oocyte by combining the membrane protein with the lipids under conditions that allow insertion or association of the membrane protein into or onto the lipid bilayer of a liposome. The constitution of the proteo-liposome and conditions of liposome formation allow the one or more membrane proteins, which is typically a recombinant protein(s) to fold and gain structure and functionality in the proteo-liposome. If the membrane protein is a membrane protein complex, the constitution of the proteo-liposome and the conditions of liposome formation allow for formation of the membrane complexes in the liposome, a process referred to herein as pre-assembly.

The proteo-liposomes are transferred to an oocyte under conditions that allow for disbursement of the membrane proteins or protein complex into the plasma membrane of the oocyte, which maintaining the structural, functional, and/or assembled stated achieved in the proteo-liposome. It is believed that the membrane proteins and liposomal lipids co-segregate in the oocytes plasma membrane such that the membrane proteins are distributed within the plasma membrane of the oocyte in a lipid environment characteristic of the proteo-liposome.

These compositions can be used to determined factors that contribute to activation and inhibition of membrane proteins, such as channels, transports, and receptors, in a controlled, cellular, and physiological, environment.

The compositions, methods, and assays disclosed herein exhibit several advantages, overcoming limitations associated with studying membrane protein complex systems using RNA/DNA expression techniques. First, this method bypasses the requirement and limitations for expression, folding, assembly and trafficking of membrane proteins, when using RNA/DNA microinjection-into-oocyte techniques. These can be particularly important when the protein of interest is a non-endogenous protein. Furthermore, it is known that membrane proteins such as connexins function as a hexamer for hemi-channel requires special machinery for proper folding and trafficking, as well as assembly of multiple protein complexes.

Second, the disclosed compositions, methods, and assays are more efficient than traditional methods. The disclosed proteo-liposomes methods reduces the time required for detecting channel activities to half-to-three hours, and the efficiency is about 70-80% of oocytes. In contrast, general cDNA injection usually takes two to three days for protein expression and the expression rates are 20-30%. Furthermore, the disclosed methods are very sensitive needing only ng of preassembled protein for each assay, and 20-30 oocytes can be easily tested on each variable. Moreover, the channel activities are sums of 200,000-1,000,000 of single channel activity at 50-100 pS, making it easy to detect.

Third, the disclosed compositions, methods, and assays can be used to identify the role of lipids for folding, assembly and function of membrane protein complexes.

Fourth, the controlled and simplified cellular environment allows the in vitro biochemical assays e.g. membrane protein functions to correlate to the semi-physiological process in the single cell oocytes.

Lastly, the disclosed compositions, methods, and assay can be used to examine the function of membrane proteins whose function is largely altered upon interacting with lipids.

Furthermore, the disclosed compositions, methods, and assays the small amount of preassembled proteins, and a small number of oocytes can be used to generate statistically meaningful data and membrane protein regulators such as $Ca^{2+}$ can be introduced into the extracellular bath solution or direct injection into the oocyte together with proteo-liposomes to study the effects of these regulators on the membrane proteins.

Certain embodiments of the disclosed methods differ from previous oocyte studies (Le Caherec et. al., (19)) which reported the injection of the reconstituted proteo-liposomes into oocytes for monitoring functional aquaporin channels. These studies demonstrated the fusion of liposomes into oocytes membranes and observed microscopically the water swelling activities without damaging the original functions of target proteins. The fusing of liposomes containing trapped water molecules into host cell cytoplasm is common in pharmacological methods (20). The direct microinjection of hydrophobic target protein into oocyte membranes has also being demonstrated. However, there is no application in microinjection of proteo-liposomes with channel activity for physiological studies.

A. Compositions

1. Proteo-Liposomes

Proteo-liposomes are protein-lipid compositions that include the membrane protein or proteins of interest and one or more lipids in an amount effective to form a liposome.

a. Lipids

The proteo-liposomes disclosed herein include one or more species of lipids in an effective amount to form a liposome. As discussed in more detail below, it has been discovered that the lipid composition of the liposome can be important for the assembly, structure, and function of the membrane protein in vivo and in the in vitro assays described herein. Therefore, the lipid content of the proteo-liposome can be selected based on the desired level of function or activity of the membrane protein once the proteo-liposome is delivered to the oocyte. For example, in some embodiments, the effect of different lipids on the function or activity of the membrane protein is known and selected based on the desired result. In some embodiments, the effect of different lipids on the function or activity of the membrane protein is determined experimentally by testing different lipid species alone or in combination using the physiological assays disclosed herein.

A "lipid" for constructing the lipid bilayer is typically a molecule having a hydrophilic head and hydrophobic tails. The lipids can be naturally occurring lipids or synthetic lipids. The lipid can have 12 to 50 carbon atoms. In preferred embodiments, the proteo-liposome includes one or more phospholipids or its derivative. The phospholipid can have 16 to 24 carbon atoms.

A phospholipid can have two acyl groups, for example, one selected from the group consisting of C12 saturated chain phospholipid, a C14 saturated chain phospholipid, a C16 saturated chain phospholipid, a C18 saturated chain phospholipid, a C20 saturated chain phospholipid, a C22 saturated chain phospholipid, and a combination thereof. The acyl group of the phospholipid can be saturated or unsaturated.

Exemplary phospholipids useful for forming the proteo-liposomes disclosed herein include diacylglyceride phospholipids such as phosphatidic acid (phosphatidate) (PA), phosphatidylethanolamine (cephalin) (PE), phosphatidylcholine (lecithin) (PC), phosphatidylserine (PS); phosphoinositides such as phosphatidylinositol (PI), phosphatidylinositol phosphate (PIP), phosphatidylinositol bisphosphate (PIP2) and phosphatidylinositol triphosphate (PIP3); and phosphosphingolipids such as ceramide phosphorylcholine (sphingomyelin) (SPH), ceramide phosphorylethanolamine (sphingomyelin), and (Cer-PE) ceramide phosphoryl lipid.

The phospholipid can be a mixture of two or more phospholipids. For example, a lipid bilayer having various phase transition temperatures may be produced due to the mixture of two or more phospholipids.

Other membrane-forming materials may be used which are not phospholipids, for example, sterol or its derivative, sphingolipid or its derivative, bola lipids or bacterial lipids. The sterol or its derivative may be cholesterol or its derivative, or squalene or its derivative. The sphingolipid may be sphingomyelin or its derivative, or ganglioside or its derivative. The phospholipid, sterol, or sphingolipid includes an intermediate or a precursor produced during a synthesis process in vivo. For example, the hydrophobic moiety includes phosphoglyceride, sphingosine, ceramide, or cerebroside. Additionally, block copolymers including a water-soluble polymer (e.g., polyethylene glycol) and a water-insoluble polymer (e.g., polypropylene oxide and polyethylethylene) may be employed.

If the proteo-liposome includes two or more lipids, the lipid content can be an equal or unequal ratio of the different lipid species. For example, in a liposome bilayer composed of 70 mole % phospholipid and 30 mole % cholesterol, and the phospholipid is the primary lipid.

In some embodiments, the ratio of one phospholipid to another is important for the function of the protein. For example, the Examples below shows that a lipid ratio of PC/PS of 2:1 or a ratio PE/PG of 3:1 can be particularly useful when the protein is a connexin such as Cx26. The Examples also show that a lipid ratio of PE/PC of 3:1 or PE/PG of 3:1 can be particularly useful when the proteins form a bacterial channel, for example, SecA. Therefore, in some embodiments, the ratio of one lipid to another is 1:1, 1:2, 1:3, 1:4, 1:5, 1:6, 1:7, 1:8, 1:9, 1:10, or more.

Most natural membranes are a complex mixture of different lipids. Therefore, the lipids used to form the proteo-liposomes can be a heterogeneous mixture of lipids that are found in the membranes, for example, the plasma membranes, of cells. The lipids can be derived or isolated from natural sources such as plasma membrane extracts of prokaryotic or eukaryotic cells. For example, the lipids of the proteo-liposomes can be from a prokaryotic or eukaryotic cell. In some embodiments, the proteo-liposomes are formed from membrane extracts from prokaryotic cells such as *E. coli*. In some embodiments, the proteo-liposomes are formed from membrane extracts from eukaryotic cells. The eukaryotic cells can be plant cells, mammalian cells, or avian sources, for example chicken brain homogenates. The lipids can be chemically synthesized lipids that mimic the natural lipids from bacteria or eukaryotic lipids. Methods of preparing liposomes from cell membranes are known in the art and can include disrupting biological membranes (such as by sonication).

The lipid or lipids can originate from any system, organ, cell, or tissue. The lipids can be from any species of interest. The Examples below illustrate that bacterial lipid extracts and synthetic lipids are effective for preparing pre-assembled proteo-liposomes. In some embodiments, the lipids are from bacteria. In some embodiments the lipids are from mammals, for example, humans. In some embodiments, the lipids are important for the pre-assembly of protein complex such as SecA channels, or connexin hemichannels.

b. Proteins

The proteo-liposomes also include one or more proteins of interest. The protein of interest is typically a membrane protein. Membrane proteins include integral membrane proteins and peripheral membrane proteins. The protein can be, for example, a membrane receptor, a transporter, an enzyme, a channel, or a cell adhesion molecule from microbial or eukaryotic sources. The one or more proteins of interest can form a protein complex in the proteo-liposome. The protein complex can have 1, 2, 3, 4, 5, 6, 7, 8, 9, 10, or more proteins of the same species or different species. For example, the protein complex can be a homo- or hetero-dimer, trimer, etc. In some embodiments, one or more proteins for a subunit, and 2 or more subunits for a protein complex. For example, one or more membrane proteins, when combined with the lipid components, can form a protein complex that is a functional channel, transporter, receptors, adhesion molecule, or enzymes.

The protein or proteins of interest can originate from any system, organ, cell, or tissue. The protein or proteins of interest can be from any species of interest. The Examples below illustrate that the disclosed compositions and methods are effective for studying structure, function, and activity of bacterial SecA protein(s) and mammalian Cx26 connexin protein(s). Therefore, in some embodiments, the proteins are bacterial proteins. In some embodiments, the proteins are mammalian proteins, for example, human proteins. In some embodiments, the proteins form channel complexes such as SecA channels, or connexin hemichannels.

Exemplary proteins and protein complexes that can be membrane proteins or form protein complexes in or on cell membranes include, but are not limited to, cyclooxygenases, hydrolases, oxidoreductases, peptidoglycan, glycosyltransferases, peptidases, dehydrogenases, dihydroorotate dehydrogenases (DHODH, class 2) polymerases, ADP-Ribosylation factors, isomerases, multimeric, monomeric/dimeric, and mitochondrial outer membrane beta-barrel membrane proteins, Omp85-TpsB outer membrane transporter superfamily proteins, beta-sheet pore-forming proteins, toxins, outer membrane proteins, bacterial rhodopsins, G Protein-Coupled Receptors (GPCRs), autonomously folding "membrane proteins" (Sec-independent), glycoproteins, SNARE Protein Family, integrin adhesion receptors, histidine kinase receptors, immune receptors, ion channels, potassium and sodium ion-selective channels, protein-conducting channels, aquaporins and glyceroporins, formate nitrate transporter (FNT) family proteins, urea transporters, gap junctions, Amt/Rh proteins, intramembrane proteases, membrane-bound metalloproteases, H+/Cl− exchange transporters, bacterial mercury detoxification proteins, multi-drug efflux transporters, Membrane-Associated Proteins in Eicosanoid and Glutathione Metabolism (MAPEG), Major Facilitator Superfamily (MFS) Transporters, Solute Sodium Symporter (SSS) family proteins, Nucleobase-Cation-Symport-1 (NCS1) family proteins, Betaine/Choline/Carnitine Transporter (BCCT) family proteins, Amino Acid/Polyamine/Organocation (APC) superfamily proteins, amino acid secondary transporters, Cation Diffusion Facilitator (CDF) family proteins, antiporters, Energy-Coupling Factor (ECF) Transporters, ATP Binding Cassette (ABC) Transporters, Superfamily of K+ Transporters (SKT proteins), P-type ATPase, V-type ATPase. F-type ATPase, phosphotransferases, hydrolases, oxygenases, oxidoreductases, Mo/W bis-MGD oxidoreductases, electron transport chain complexes, including Complex I, Complex II, Complex III (Cytochrome bc1), Cytochrome b6f of Oxygenic Photosynthesis, and Complex IV (Cytochrome C Oxidase), nitric oxide reductases, photosystems, light-harvesting complex proteins, and photosynthetic reaction center proteins.

Typically, the one or more proteins of interest are isolated or purified. For example, the protein of interest can be a recombinant protein that is expressed in a recombinant protein expression system.

i. Expressing Recombinant Proteins

The engineering of DNA segment(s) for expression in a prokaryotic or eukaryotic system may be performed by techniques generally known to those of skill in recombinant expression. It is believed that virtually any expression system may be employed in the expression of the disclosed membrane proteins.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene.

Recombinant cells include those having an introduced cDNA or genomic DNA, and also include genes positioned adjacent to a promoter not naturally associated with the particular introduced gene.

To express a recombinant encoded protein or peptide, whether mutant or wild-type, one would prepare an expression vector that includes a nucleic acid encoding a membrane protein under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as E. coli and B. subtilis transformed with recombinant phage DNA, plasmid DNA or cosmid DNA expression vectors.

Certain examples of prokaryotic hosts are E. coli strain RR1, E. coli LE392, E. coli B, E. coli 1776 (ATCC® No. 31537) as well as E. coli W3110 (F−, lambda−, prototrophic, ATCC® No. 273325); bacilli such as Bacillus subtilis; and other enterobacteriaceae such as Salmonella typhimurium, Serratia marcescens, and various Pseudomonas species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, E. coli is often transformed using pBR322, a plasmid derived from an E. coli species. Plasmid pBR322 contains genes for ampicillin and tetracycline resistance and thus provides easy means for identifying transformed cells. The pBR322 plasmid, or other microbial plasmid or phage must also contain, or be modified to contain, promoters that can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector that can be used to transform host cells, such as E. coli LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems.

While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used. This plasmid contains the trpl gene, which provides a selection marker for a mutant strain of yeast lacking the ability to grow in tryptophan, for example ATCC® No. 44076 or PEP4-1. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autograph californica* nuclear polyhidrosis virus (AcNPV) is used as a vector to express foreign genes. The virus grows in *Spodoptera frugiperda* cells. The isolated nucleic acid coding sequences are cloned into non-essential regions (for example the polyhedron gene) of the virus and placed under control of an AcNPV promoter (for example, the polyhedron promoter). Successful insertion of the coding sequences results in the inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed.

Examples of useful mammalian host cell lines are VERO and HeLa cells, Chinese hamster ovary (CHO) cell lines, W138, BHK, COS-7, 293, HepG2, NIH3T3, RIN and MDCK cell lines. In addition, a host cell may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems can be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HinDIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides downstream of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems may be used, including, but not limited, to the herpes simplex virus thymidine kinase, hypoxanthine-guanine phosphoribosyltransferase and adenine phosphoribosyltransferase genes, in $tk^-$, $hgprt^-$ or $aprt^-$ cells, respectively. Also, antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin.

The protein can optionally include additional sequences or moieties, including, but not limited to linkers and purification tags.

In a preferred embodiment the purification tag is a polypeptide. Polypeptide purification tags are known in the art and include, but are not limited to His tags which typically include six or more, typically consecutive, histidine residues; FLAG tags, haemagglutinin (HA) for example, or MYC tag. Methods of using purification tags to facilitate protein purification are known in the art and include, for example, a chromatography step wherein the tag reversibly binds to a chromatography resin.

Purifications tags can be N-terminal or C-terminal to the fusion protein. The purification tags N-terminal to the fusion protein are typically separated from the polypeptide of interest at the time of the cleavage in vivo. Therefore, purification tags N-terminal to the fusion protein can be used to remove the fusion protein from a cellular lysate following expression and extraction of the expression or solubility enhancing amino acid sequence, but cannot be used to remove the polypeptide of interest. Purification tags C-terminal to the fusion protein can be used to remove the polypeptide of interest from a cellular lysate following expression of the fusion protein, but cannot be used to remove the expression or solubility enhancing amino acid sequence. Purification tags that are C-terminal to the expression or solubility enhancing amino acid sequence can be N-terminal to, C-terminal to, or incorporated within the sequence of the polypeptide of interest.

In some embodiments, to fusion protein includes one or more linkers or spacers. In some embodiments linker or spacer is one or more polypeptides. In some embodiments, the linker includes a glycine-glutamic acid di-amino acid sequence. The linkers can be used to link or connect two domains, regions, or sequences of the fusion protein.

It is contemplated that the isolated nucleic acids can be used to generate the recombinant proteins used in the compositions, methods, and assays used herein. The isolated nucleic acids "overexpressed", i.e., expressed in increased levels relative to its natural expression in human cells, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

Although many proteins with therapeutic or commercial uses can be produced by recombinant organisms, the yield and quality of the expressed protein are variable due to many factors. For example, heterologous protein expression by genetically engineered organisms can be affected by the size and source of the protein to be expressed, the presence of an affinity tag linked to the protein to be expressed, codon biasing, the strain of the microorganism, the culture conditions of microorganism, and the in vivo degradation of the expressed protein. Some of these problems can be mitigated by fusing the protein of interest to an expression or solubility enhancing amino acid sequence. Exemplary expression or solubility enhancing amino acid sequences include maltose-binding protein (MBP), glutathione S-transferase (GST), thioredoxin (TRX), NUS A, ubiquitin (Ub), and a small ubiquitin-related modifier (SUMO).

In some embodiments, the compositions disclosed herein include expression or solubility enhancing amino acid sequence. In some embodiments, the expression or solubility enhancing amino acid sequence is cleaved prior administration of the composition to a subject in need thereof. The expression or solubility enhancing amino acid sequence can be cleaved after expression of the protein. In some embodiments, the expression or solubility enhancing is a ULP1 or SUMO sequence. Recombinant protein expression systems that incorporate the SUMO protein ("SUMO fusion systems") have been shown to increase efficiency and reduce defective expression of recombinant proteins in E. coli., see for example Malakhov, et al., J. Struct. Funct. Genomics, 5: 75-86 (2004), U.S. Pat. No. 7,060,461, and U.S. Pat. No. 6,872,551. SUMO fusion systems enhance expression and solubility of certain proteins, including severe acute respiratory syndrome coronavirus (SARS-CoV) 3CL protease, nucleocapsid, and membrane proteins (Zuo et al., J. Struct. Funct. Genomics, 6:103-111 (2005)).

ii. Purification of Expressed Proteins

Composition and methods for purification, or the substantial purification, of an encoded protein or peptide are also disclosed. The term "purified protein or peptide" as used herein, is intended to refer to a composition, isolatable from other components, wherein the protein or peptide is purified to any degree relative to its naturally-obtainable state, i.e., in this case, relative to its purity within a hepatocyte or p-cell extract. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, polyethylene glycol, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE. It will therefore be appreciated that under differing electrophoresis conditions, the apparent molecular weights of purified or partially purified expression products may vary.

B. Oocytes

The oocytes utilized in the disclosed methods are typically oocytes from the African clawed frog *Xenopus laevis*, also known as the *Xenopus*. The *Xenopus laevis* oocyte is a popular model for electrophysiology studies such as those described herein because of their large size (~1.0-1.2 mm) which makes their handling and manipulation easy.

Oocytes are precursors to mature egg cells and are stored in the ovarian lobes of the adult female frog. The oocytes have two poles, the animal pole and the vegetal pole. The animal pole is dark brown in color and the vegetal pole is yellow. The oocytes are typically classified in stages (from stage I to stage VI) depending their developmental state. Stage V and VI oocytes are typically used in the compositions and methods disclosed herein. The oocytes are harvested by survival surgery or after euthanization of the frog, or can be purchased from a commercial vendor such NASCO®.

Typically, a section of an ovary is isolated from a frog and put into a storage solution (for example, OR-2). Oocytes are isolated from this partial ovary. Methods of isolating oocytes from *Xenopus* are known in the art, see, for example, Mao, et al., PNAS, 101:1087-1092 (2004), Xu, et al., *J. Biol. Chem.*, 276:12898-12902 (2001), and Lin, et al., *J. Membr. Biol.*, 214(2): 103-113 (2006).

The oocyte plasma membrane is surrounded by a vitelline membrane that provides shape and structure to the oocyte. The vitelline membrane does not affect electrophysiological recordings because it is absent of channels and transporters and has a large-enough mesh to allow permeation of ions and small molecules. However, for some embodiments such single channel recordings and two-cell patch clamp recordings, the vitelline membrane is removed because it hinders the formation of high resistance seal between the patch pipette and the oocyte membrane.

Around the vitelline membrane is a layer of follicular cells that separates the oocyte from the external environment. By contrast to the vitelline membrane, the follicular cells express ion channels and transporters that are electrically coupled to each other and to the oocyte by gap junctions. The follicular cells can be left intact or removed, either manually, by treatment with collagenase, or a combination thereof. The follicular cells can create serious interference during electrophysiological recordings, therefore, this layer of cells is typically eliminated prior to use of the oocytes in the disclosed compositions and methods.

Typically, the oocytes are cultured for 2-3 days in media until the oocytes mature. Suitable media and culture conditions are known in the art.

B. Methods of Preparing Treated Oocytes

The treated oocytes are prepared by introducing proteo-liposomes into the oocyte. Prior to introduction into the oocyte, the proteo-liposomes are prepared with materials and under conditions suitable for folding and preassembly of the protein or protein complexes in the proteo-liposome.

1. Preparation of Proteo-Liposomes a. Liposome Preparation

Typically, total lipid extracts, such total lipid extracts from *E. coli*, or synthetic lipids, are dried and resuspended in a suitable buffer. An exemplary buffer is TAK buffer containing Tris-HCl 50 mM pH 7.6, 20 mM $NH_4Cl$ and 25 mM KCl.

If more than one synthetic lipid is used, the different lipids can be combined in a desirable ratio. For example, the Examples below utilize ratios such as PC/PS of 2:1, or PE/PG of 3:1, or PE/PC of 3:1, or PE/PG of 3:1. The suspension can be disrupted, for example using sonication, to induce mixing of the lipid species and formation of liposomal particles. The liposomes are general prepared in a particle size of between about 1 nm and 1,000 nm, or between about 10 nm and 500 nm, or between about 75 nm and 250 nm, or between about 100 nm and 150 nm. The Examples below illustrate the preparation and use of particles that are about 130 nm. In some embodiments, the particles are uniform or similar in size. In some embodiments, the particles include broad range of different sized particles. Preferably the particles are uniform or nearly uniform in size.

In some embodiments, the liposomes are inverted membranes using known methods. For example, inverted membrane can be prepared using sucrose gradients, see, Yang, *J. Biol. Chem.*, 272, 13660-13665 (1997) and Yang, J. Lian, *J. Bacteriol.*, 179 7386-7393 (1997).

The liposomes can be aliquoted and stored, for example at −80° C., until use.

b. Reconstitution of Membrane Proteins

Isolated or purified membrane protein or proteins of interest are contacted or mixed with the liposomes to form proteo-liposomes in a step referred to herein as pre-assembly. The liposomes and proteins are incubated under appropriate conditions and for sufficient time to allow the proteins to fold, associate or integrate on or into the liposomal membrane, and regain structure and function. If the protein or proteins of interest function in a protein complex, the liposomes and proteins are incubated under appropriate conditions and sufficient time for the proteins to form the protein complexes. In preferred embodiments, the protein of interest will readily interact with liposomes, so its reconstitution with liposomes can be carried out by direct binding or by dialysis with denatured protein. For example, in the working Examples below, the proteins of interest were mixed with either total lipid extracts from *E. coli*, or synthetic lipids, in TK buffer (10 mM Tris-HCl, pH 7.6 and 50 mM KCl) by vortex and incubated at 4° C. for at least 30 minutes.

The ratio of liposome to protein can range from 100:1 to 1:1, or 50:1 to 5:1, or be about 10:1. For example, in the Examples below liposomes treated with detergent were mixed with purified connexin protein Cx26 at 10:1 ratio. Then the mixture was dialyzed in dialysis solution (0.25 M Sucrose, 0.4 M KOAC, 20 mM triethanolamine hydrocholoride pH 7.5, 1.5 mM $Mg(OAC)_2$ and 1 mM EDTA) at 4° C. for 15-18 hours to reconstitute the Cx-26-proteo-liposomes.

2. Preparation of Treated Oocytes

Treated oocytes are prepared by contacting the proteo-liposomes including pre-assembled membrane proteins with oocytes. An exemplary method of delivering the proteo-liposomes to the oocytes is injection. Suitable methods of oocyte injection are known in the art. An exemplary injection method is described in Lin, et al., *J. Membr. Biol.*, 214(2): 103-113 (2006). Briefly, proteo-liposomes in various concentrations can be prepared as described herein, and injected into the dark animal pole of the oocytes using a borosilicate glass pipette (for example, 1.2 mm outside diameter, 0.69 mm inside diameter) connected to a suitable injector (such as Nanoject II by Drummond Scientific, Broomall, Pa.). The glass pipettes can be pulled from a Micropipette Puller (such as Flaming/Brown model P-97, Sutter Instrument). Typically, the tip is trimmed to 15-18 μm in inner diameter prior to use.

The oocytes can be maintained at 23° C. in ND-96 buffer (96 mM NaCl, 2 mM KCl, 1 mM MgCl2, 1.8 mM CaCl2, 5 mM HEPES, 40 mg/l sodium pyruvate and 100 mg/l geneticin [pH 7.4]) with tetracycline (100 mg/l) to prevent bacterial growth in the buffer solution. One of skill in the art understands that this is one of many exemplary injection methods useful in preparing the disclose oocytes, and steps of the injection method and reagents used in the method can be modified accordingly.

The preferred amount of proteo-liposome to be injected for each specific membrane protein can be determined using routine methods, for example dosage escalation studies. Generally, oocytes are injected with between about 1 ng and 1,000 ng, or between about 5 ng and 500 ng, or between about 7.5 ng and 25 ng, or about 10 ng of proteo-liposome.

It is believed that one or more of magnesium (Mg), ATP, calcium, and EGTA are factors that can be important for achieving activity of certain membrane proteins, such as channel proteins, in the plasma membrane of the oocyte. Therefore, these factors can be added or present during any or all of the steps associated with preparation and use of the treated oocytes. For example, the Mg, ATP, calcium, EGTA or a combination thereof can be present in the liposome preparation buffer, the proteo-liposome preparation buffer, the injection buffer, the oocyte incubation or maintenance buffer, or any combination thereof.

Prior to introduction in the oocytes, the proteo-liposomes are incubated under conditions suitable for folding of the protein of interest, for the protein of interest to traffic to an associate with or integrate into the lipid bilayer of liposome, if the protein is a protein complex, for the complex to assemble. The incubation period can be, for example, 1, 5, 10, 15, 20, 30 or more minutes depending on the protein of interest. In some embodiments, the protein is give 1, 2, 3, 4, 5, 6, 12, 24, or 36 hours to pre-assemble. In a preferred embodiment, the proteins pre-assemble in 4 minutes or less. The pre-assembly can be carried out, for example, at 30° C. Following injection, membrane proteins can be detected in the oocyte plasma membrane after as little as 30 minutes.

III. Methods of Using Treated Oocytes

The treated oocytes disclosed herein can be used in a variety of assays, including, for example physiological assays to study the membrane protein of interest. For example, assays can be selected and utilized to characterize the assembly, orientation, activity, lipid requirements, structure, function, or structure-function correlations of the membrane proteins of interest. In some embodiments, the assays are used to compare the a wildtype protein to a mutant to determine the effect of the mutation or mutations on assembly, orientation, activity, lipid requirements, structure, function, or structure-function correlations of the membrane proteins of interest.

The treated oocytes disclosed herein can also be used in screening assays. For example, the oocytes can be used to screen for compounds that increase or decrease the assembly, orientation, activity, lipid requirements, structure, function, or structure-function correlations of the membrane proteins of interest.

A. Physiological Assays

The disclosed treated oocytes can be used in a variety of physiological assays. Such assay are known in the art, see for example, Goldin, A. L. (2006) *Expression of Ion Channels in Xenopus Oocytes*, in Expression and Analysis of Recombinant Ion Channels: From Structural Studies to Pharmacological Screening (eds J. J. Clare and D. J. Trezise), Wiley-VCH Verlag GmbH & Co. KGaA, Weinheim, FRG., which is incorporated by reference herein in its entirety.

Preferred assays include, but are not limited to, electrophysiology assays such as two-electrode whole cell voltage-clamp, cut-open oocyte voltage-clamp, macropatch clamp, and single channel analysis. In some embodiments, the assays are biochemical assays. Techniques such as serial recording (using the Roboocyte, for example) and parallel recording (using the OpusXpress, for example) can also be employed.

For example, in a particular preferred embodiment the protein or proteins of interest for an ion channel. The opening of protein conducting channels of the reconstituted ion channels in the treated oocyte's plasma membrane can be monitored using voltage clamp methods that are known in the art, such as one adapted from an electrophysiological method described in Hsieh, et al., *J. Biol. Chem.*, 286:44702-44709 (2011), Lin, et al., *J. Membr. Biol.*, 245:747-757 (2012), and Dalal, et al., *Methods Mol. Biol.*, 619:45-156 (2010).

In some embodiments, additional factors are injected into the oocyte or added to the extracellular bath. The factors can include, for example, buffers or other elements needed to carry out the physiological or biochemical assay, membrane protein regulators, $Ca^{2+}$ ect., or combinations thereof.

B. Exemplary Applications

1. Structural and Functional Relationship

In some embodiments, the disclosed compositions, methods, and assays are used to study the structure-function relationship of the protein or protein complex of interest. One of the most powerful uses for oocytes in the study of ion channels has been to correlate molecular structure with biochemical and electrophysiological functions. The Examples below illustrate that preassembled connexin hemichannel in a proteo-liposome can be integrated into the membrane of the oocyte membrane and exhibit channel activity. Thus, the ratio of the complex such as monomer, dimer, and hexamer can be examined. For example, it is possible to adjust the ratio of each subunit in the proteo-liposome and preassembled them first before injection to examine channels with a relatively well controlled composition. *Xenopus* oocytes do not have lots of endogenous channel contamination (Taglialatela, et al., *Biophys J.*, 61(1): 78-82 (1992)), adding to the advantages of this system.

2. Membrane Protein Regulation

In some embodiments, the disclosed compositions, methods, and assays are used to study regulation of the membrane protein or protein complex. For example, the treated oocytes can be treated with various factors to induce conformation changes in the protein or complex. In some embodiments, the membrane protein or complex is a receptor and the treated oocytes are used to analyze ligand binding under physiologically relevant conditions. In other embodiments, the membrane protein is a channel which is analyzed in the presence of factors or co-factors such as calcium, protons, calmodulin, etc. In some embodiments, ligand binding assays against different channel mutation or variation combinations can be carried out on a single oocyte.

3. Exemplary Proteins

Proteins that can be studied using the disclosed methods include protein receptors, pumps, and other membrane proteins that have previous been shown to integrate into oocyte plasma membrane using alternative techniques should as RNA/DNA delivery methods. Exemplary proteins, and the species thereof, are listed in

TABLE 1

Broad species specificity for functional protein expression in *Xenopus oocytes*

| Model organism | Species | Expressed construct | References |
|---|---|---|---|
| Plant (dicot) | *Arabidopxis* | $Ca^{2+}$ regulated channel (glutamate receptor) | Roy et al. 2008 |
| Plant (monocot) | *Oryza* | $Ca^{2+}$ permeable channel (HKT) | Lan et al. 2010 |
| Green algae | *Chlamydomonas* | Light-activated $Ca^{2+}$ channel (ChR2) | Nagel et al. 2003 |
| Alveolate | *Plasmodium* | $Ca^{2+}$ ATPase (PfATP6) | Eckstein-Ludwig et al. 2003 |
| Amoeba | *Dictyastelium* | $P_2X$ receptors ($dP_2X$) | Ludlow et al. 2009 |
| Euglenozoa | *Trypanosomes* | $K^+$ transporter (TbHKT1) | Mosimann et al. 2010 |
| Yeast | *Saccharomyces* | Outward rectifier $K^+$ channel (YORK) | Lesage et al. 1996 |
| Sponge | *Amphmedon* | Inward rectifier $K^+$ channel (AmqKir) | Tompkins-Macdonald et al. 2009 |
| Mollusc | *Laligo* | Voltage-activated $Ca^{2+}$ channel (Ca,2) | Kimura and Kubo 2002 |
| Worm | *C. elegans* | $Ca^{2+}$ permeable channel (MEC4(d)) | Bianchi et al. 2004 |
| Insects | *Blatelis, Drosophila* | Voltage-activated $Ca^{2+}$ channel (DSC1, BSC1) | Zhou et al. 2004; Zhang et al. 2011 |
| Flatworm | *Schistosoma* | Ligand-gated $Ca^{2+}$ channel ($P_2X$) | Agboh et al. 2004 |
| Cnidarian (jellyfish) | *Cyanea* | Voltage-activated $Ca^{2+}$ channel ($C\gamma Ca_1$) | jeziorski et al. 1998 |
| Echinoderm (sea urchin) | *Strongylocentrous purpuratus* | Intracellutar $Ca^{2+}$ Channel (TPC) | Brailoiu et al. 2009 |
| Chordate (lunicate) | *Halocynthia* | Voltage-activated $Ca^{2+}$ channel (TuCa1) | Izumi-Nakaseko et al. 2003 |

Where possible, there examples illustrate $Ca^{2+}$-permeable channels or transporters. Because of limited space, only single examples are shown for each model.

4. Mutation Analysis

In some embodiments, the disclosed compositions, methods, and assays are used to examine the effect of one or more mutations on the structure, function, or activity of a particular protein or complex. In a preferred embodiment, the mutation is one characteristic of a disease. For example, the discloses compositions, methods, and assays, allow for direct analysis of the effects of ion channel mutations that cause human diseases including mutant voltage-gated sodium channels that cause diseases of the musculoskeletal, cardiovascular and nervous system, Alzheimer disease, etc.

In some embodiments, the mutated proteins are utilized in the screening methods disclosed herein to identify compounds that modulate the activity of the mutant protein.

5. Lipid Microenvironment Analysis

In some embodiments, the disclosed compositions, methods, and assays are used to examine the effect of different lipids, or combinations of lipids, on the structure, function, or activity of a particular protein or complex. The lipid bilayer is important for maintaining the integrity of cellular compartments and plays an important role in providing the hydrophobic and charged interactions needed for membrane protein structure, conformational flexibility and function.

For example, it is known that the anionic phospholipids are important for SecA ATPase activity (11), protein translocation and ring-pore structures (21). The Examples below show that lipid microenvironment in the plasma membrane is important for structure and function of certain membrane proteins such as SecA in bacteria. More specifically, the Examples support a model in which SecA alone is capable of forming a lipid-specific, asymmetric dimer that is able to function as a viable-protein conducting channel in the membrane.

Thus even though SecA cannot function with oocytes membranes (9) the protein does function in the oocytes with *E. coli* lipid extracts which contains mostly PG, cardiolipin and PE. However, the Examples below also illustrate that the ratios of synthetic lipids can be important for some membrane proteins such as SecA channels. For example, with respect to SecA, PG alone does not function, and proper ratios of PG/PC or PG/PE work well, but not PS/PE.

The Examples also show that human Cx26 reconstituted with PC/PS functions well. This is consistent with lipids associated to the protein using Mass spectrometry by Locke and Harris (7). Furthermore, the Examples show that Cx26 hemi-channel is also assembled in proteo-liposomes by synthetic PG/PE and bacterial lipids. Thus *E. coli* lipid extracts or synthetic PG/PE mixtures might be generally used for reconstituted liposomes to be injected into oocytes.

Other studies have shown the lipid dependence of activity for voltage-gated sodium channels by comparing the activity of three bacterial sodium channel homologues (NaChBac, NavMs, and NavSp) by cumulative 22Na+ uptake into proteoliposomes containing a 3:1 ratio of 1-palmitoyl 2-oleoyl phosphatidylethanolamine and different "guest" glycerophospholipids. D'Avanzo, et al., *PLoS ONE*, 8(4): e61216 (2013) reported a unique lipid profile for each channel tested. NavMs and NavSp showed strong preference for different negatively-charged lipids (phosphatidylinositol and phosphatidylglycerol, respectively), while NaChBac exhibited a more modest variation with lipid type.

The disclosed compositions, methods, and assays can be used to investigate the effect of specific lipids, and combinations of lipids on the structure, function, and activity of membrane proteins. For example, the disclosed compositions, methods, and assays can be used to determine if lipids interact directly with the voltage-sensing subdomains of voltage-gated sodium channels.

Philips, et al., *Nature*, 459:379-385 (2009) stated that studies of membrane proteins have revealed a direct link between the lipid environment and the structure and function of some of these proteins. Although some of these effects involve specific chemical interactions between lipids and protein residues, many can be understood in terms of protein-induced perturbations to the membrane shape. The disclosed compositions, methods, and assays can be used to investigate the free-energy cost of such perturbations quantitatively, and gather measurements of channel gating in model systems of membrane proteins with their lipid partners.

Therefore in some embodiments, the protein of interest is pre-assembled in liposomes with various different lipid compositions, each of which are introduced into an oocyte and analyzed using biochemical, physiological, or a combination thereof. By comparing the results of the assays using oocytes injected with proteo-liposome of different liposome compositions, one can determine the effect of the lipid composition on the folding, structure, function, or activity of the protein, and screen for the most effective lipid composition for any protein of interest. The lipid composition can be varied by the types of lipids used, the ratios thereof, or a combination thereof.

C. Methods of Screening Test Compounds

In some embodiments, the treated oocytes are used to identify modulators that increase or decrease the activity or function of the membrane protein or complex of interest. The modulators can be nucleic acids, polypeptides, proteins, small molecules, or other classes of compounds.

In some embodiments, screening assays can include random screening of large libraries of test compounds. Alternatively, the assays may be used to focus on particular classes of compounds suspected of modulating the activity of the protein or complex of interest. Assays can include physiological and biochemical assays such as those disclosed above, or other assays design based on the structure, function, or a combination thereof of the protein on complex of interest. Specific assay endpoints or interactions that may be measured in the disclosed embodiments can be determined based on the function of the protein or channel. For example, if the protein or complex of interest is an ion channel, the assay may be measuring the opening of protein conducting channels by voltage clamp methods. In some embodiments, the assay, or measurement of the assay endpoints, includes standard methods such as ELISA, Western blotting, or combinations thereof.

An exemplary screen is provided in the Examples below, where various test compounds were evaluated in the channel activity assay using both EcSecA-proteo-liposomes and BsSecA-proteo-liposomes.

Electrophysiological assays such as those discussed above and exemplified in the Examples below are preferred assays for determining the effect of a test compound or drug on a channel such as a voltage-gated channel. The compositions, methods, and assays disclosed herein can be used to analyze multiple channel variations such as mutations or different compositions of subunits, and the effect of various compounds or drugs on the variations or mutations.

The human genome project identified about 300-400 putative ion channel genes. Traditionally, the pharmaceutical industry has focused on only about 30 ion channels, leaving a huge untapped source of possible ion channels as drug targets. While ion channels were first discovered and studied in neuronal and muscle cells, they are found in all cells of the body and have been implicated in a wide range of neurological and muscular disorders, including migraine, epilepsy, myotonia, and cardiac rhythm problems.

Ion channels have also been implicated in disorders of other tissues such as cystic fibrosis. Furthermore, many drugs that target gene products other than ion channels also interact with ion channels, indicated that drug investigations need to test putative compounds for crossreactivity, especially in the area of targets involved in the cardiac action potential and contractility.

Voltage-clamp techniques are typically used to study the plasma membrane proteins, such as ion channels and transporters that control bioelectrical signals. Many of these proteins have been cloned and can now be studied as potential targets for drug development. The two traditional approaches used for heterologous expression of cloned ion channels and transporters involve either transfection of the genes into small cells grown in tissue culture or the injection of the genetic material into larger cells. The standard large cells used for the expression of cloned cDNA or synthetic RNA are the egg progenitor cells (oocytes) of the African frog, *Xenopus laevis*.

Until recently, cellular electrophysiology was performed manually by a single operator, one cell at a time. However, methods of high throughput electrophysiology have been developed which are automated and permit data acquisition and analysis from multiple cells in parallel. These methods can be used in combination with the disclosed compositions, methods, and assays and are useful for primary screening as well as for thorough characterization of test compounds. Some examples of studies that can benefit from high throughput electrophysiology include pharmaceutical screening of targeted compound libraries, secondary screening of identified compounds for subtype selectivity, screening mutants of ligand-gated channels for changes in receptor function, scanning mutagenesis of protein segments, and mutant-cycle analysis.

Several auto-screen protocols have been established, for example Oocyteexpress. See also Roger, et al., *Combinatorial Chemistry & High Throughput Screening*, 12:38-50 (2009). These screening protocols can be used in combination with the disclosed compositions, methods, and assays.

EXAMPLES

Example 1: Direct Injection of SecA-Liposomes into Oocytes

Materials and Methods
Protein Purification:

*E. coli* SecA was obtained from BL21(λDE3)/pT7-SecA, as described (23). SecA homologs from other bacteria were purified similarly from BL21.19 as described previously (22, 23, 26). Purified proOmpA, were prepared as described (30), and SecYEG and SecDF•YajC were purified as described (10). Gap junction protein Cx26 was expressed in insect Sf9 using the Bac-to-Bac baculovirus expression system (INVITROGEN®, Invitrogen Corporation). MCx26-His6 cDNA was inserted into the modified pFast Bac HT A vector (without N-terminal his tag) at BamHI and HindIII restriction sites. Recombinant baculoviruses were prepared following the instructions of the manufacturer (INVITROGEN®, Invitrogen Corporation). Insect Sf9 cells were cultured in the Sf-900™ II SFM media and were infected at a density ~1×10$^6$ cells/ml for expression. The baculovirus-expressed connexins harboring a His6 tag was purified using HISPUR™ Cobalt column (Thermo Scientific®, Thermo Fisher Scientific Inc.) according to published methods. Protein concentration was determined by A280/260 ratio or Bradford assay (10).

Liposomes Preparation:

*E. coli* total lipids extracts or synthetic lipids (Avanti Polar Lipid, Inc) were dried in the Thermo Savant vacuum and resuspended in TAK buffer containing Tris-HCl 50 mM pH 7.6, 20 mM NH4Cl and 25 mM KCl. The PC/PS ratio was 2:1 and the PE/PG ratio was 3:1. The suspension was subjected to sonication (Fisher Scientific Sonic Dismembrator Model 500) at the amplitude of 70% for 8 to 10 minutes with two minute pause in a 0° C. ice-water bath. The particle sizes of opalescent liposomes were measured by a Beckman Coulter N5 submicron particle size analyzer and showed a normal distribution with a peak around 130 nm. The liposomes were aliquoted and stored at −80° C. until use.

Reconstitution of SecA-Liposomes:

Liposomes from *E. coli* lipid mixtures or synthetic lipids, and purified SecA were mixed in the TK buffer (10 mM Tris-HCl, pH 7.6 and 50 mM KCl) by vortex and incubated at 4° C. for at least 30 mins to form the SecA-liposomes. SecYEG-SecDF•YajC reconstitution with liposomes was as described (10).

Treatment of Oocytes for Injection:

Oocytes were obtained from *Xenopus laevis*. The frogs were anesthetized in 0.3% 3-aminobenzoic acid ethylester for 30-40 mins 4. A small abdominal incision was made and ovaries were taken out as needed. The incision was closed and the frog was placed in recover tank until wake up. The oocytes clusters were digested with 2 mg/ml of Type IA collagenase in the OR2 solution (82 mM NaCl, 2 mM KCl, 1 mM $MgCl_2$, and 5 mM HEPES, pH 7.4) for 25-30 mins or until 70% of tissue digestion was done. After three times of wash with OR2 solution, the second digestion was done for less than 5 mins to make sure 90% of digestion was completed. The oocytes then were washed with excess OR2 solution to remove the collagenase and then incubated with 2% Fetal Bovine Serum (FBS) for 5 mins to remove the tissue residues. After wash, the oocytes were maintained in 16° C. in ND96 (96 mM NaCl, 2 mM KCl, 1 mM $MgCl_2$, 1.8 mM $CaCl_2$, 5 mM HEPES, pH 7.4, 40 mg/l sodium pyruvate, 100 mg/l geneticin, and 100 mg/l tetracycline) solution for 2-4 days in order to keep stable and constant results.

SecA-Liposomes Injection:

SecA-liposomes with proOmpA and other essential components were mixed in the TK buffer (10 mM Tris-HCl, pH 7.6 and 50 mM KCl) and incubated at 30° C. for 4 mins before injection. The 50 nl sample mixture was then injected into dark Animal Pole site of oocytes by using Nanoject II injector (Drummond Scientific Co., Broomall, Pa.). The injected oocytes were stored at 23° C. in ND-96 solution for 3 hours. The typical working concentration for each component for SecA liposomes is 120 liposomes, 120 ng SecA, 2 mM ATP, 1 mM $Mg(OAC)_2$ and 0.28 pmole proOmpA. For SecYEG or SecYEG/SecDF•YajC reconstitution, the amount of SecYEG is 0.47 ng and the SecDFYajC is 0.53 ng. The effective concentration of chemical in the oocytes was estimated based on the average volume of oocytes at 500 nl with 50 nl injections.

Two Electrons Whole Cell Recording:

Voltage Clamp was performed to measure the opening of protein conducting channels. When the channel on the cell membrane was opened, ions pass through the membrane and generate the ionic current. Thus, the recording of ionic current could also mean the opening of the protein conducting channel. Currents through the plasma membranes of oocytes were measured after the oocytes were injected with tested materials. The cells were place in a recording chamber (BSC-HT, Medical System, Greenvale, N.Y.) on a supporting nylon mesh, so that the perfusion solution bathed both the top and the bottom surface of the oocytes. Two electrode voltage clamping was performed using an amplifier (Geneclamp 500, Axon instruments Inc., Foster City, Calif.) at room temperature (23-25° C.). Cells were impaled using electrodes filled with 3 M KCl. One of the electrode (1.0-2.0 MΩ) used for voltage recording was connected to the HS-2×1 L headstage (input resistance, 1011Ω), and the other electrode (0.3-0.6 MΩ) was used for current recording to the HS-2×10 MG headstage (maximum current, 130 μA). The electrode was connected through a silver wire that was chloridized freshly for each experiment. Oocytes were used for further experiments only if their leak currents measured as the difference before and after a leak subtraction were less than 10% of the peak currents. The leak subtraction was not applied for data acquisition and analysis. Current records were low-pass filtered (Bessel, 4-pole filter, 3 db at 5 kHz), digitized at 5 kHz (12 but resolution), and analyzed using pClamp6 (Axon Instruments). The highest and lowest records were eliminated, and then the data are presented as mean±S.E. (standard error; n, number of oocytes). The expression rates for each injection sample were also collected as a record to determine the channel activity efficiency.

Results

Figure 2A:
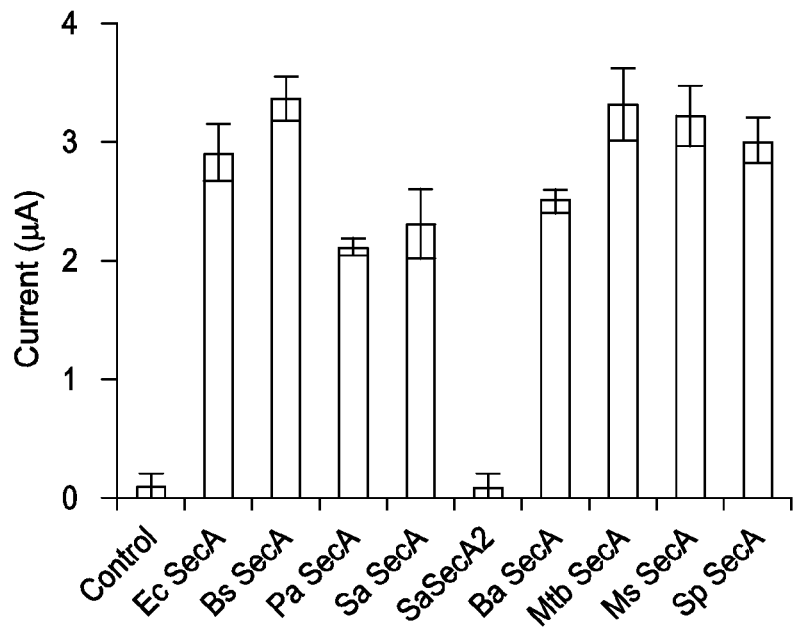
FIGS. 2A-2B.

Pre-assembled membrane proteins embedded in liposomes are able to incorporate into oocyte plasma membranes upon injection, which enables the detection of channel activity. Through direct injection of proteo-liposomes together with important factors such as ATP-Mg, and precursor proOmpA, increased outward currents with *E. coli* SecA were detected (FIG. 1, FIG. 2A). Liposomes with purified SecA homologs from other bacteria, including *Bacillus subtilis, Bacillus anthraces, Staphylococcus aureus, Streptococcus pyogenes, Pseudomonas aeruginosa, Mycobacterium tuberculosis*, and *Mycobacterium smegatatis* all showed similar channel activities (FIG. 2A).

Figure 2B:
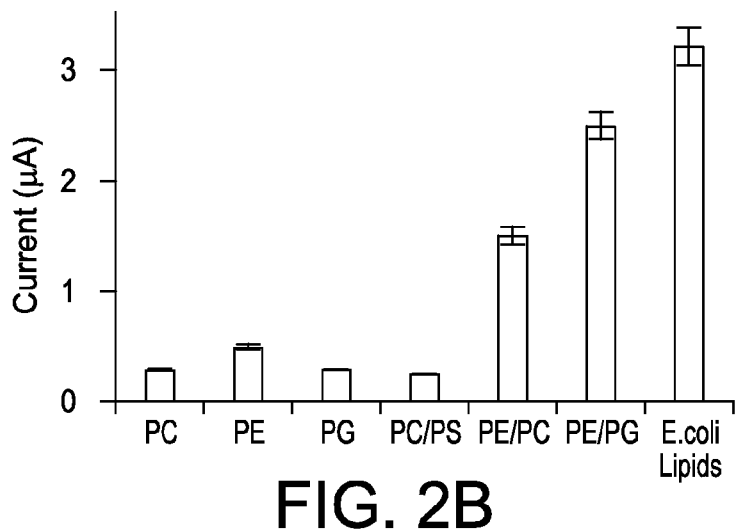

Soluble SecA readily interacts with liposomes, so its reconstitution with liposomes by direct binding or by dialysis with denatured SecA, followed by injection with other essential components revealed similar channel activity. On the other hand, the soluble SecA2 homologs from some Gram-positive bacteria (e.g. SecA from *S. aureus*, SaSecA2) do not form the pore ring structures with liposomes, and have no channel activities, indicating specificity in their channel formation. In this system, the liposomes made of *E. coli* lipid extracts or synthetic PG/PE mixtures (1:3 ratios) were necessary for SecA to incorporate into oocyte membranes for the current to be recorded; the PG/PE, itself was not active (FIG. 2B).

Example 2: Incorporation of Reconstituted Complex Channels

Results

Figure 3A:
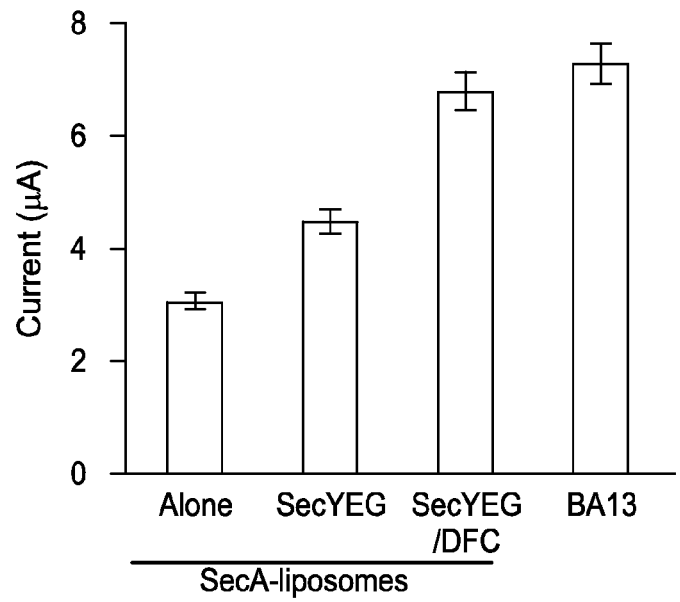
FIGS. 3A-3B.
Figure 3B:
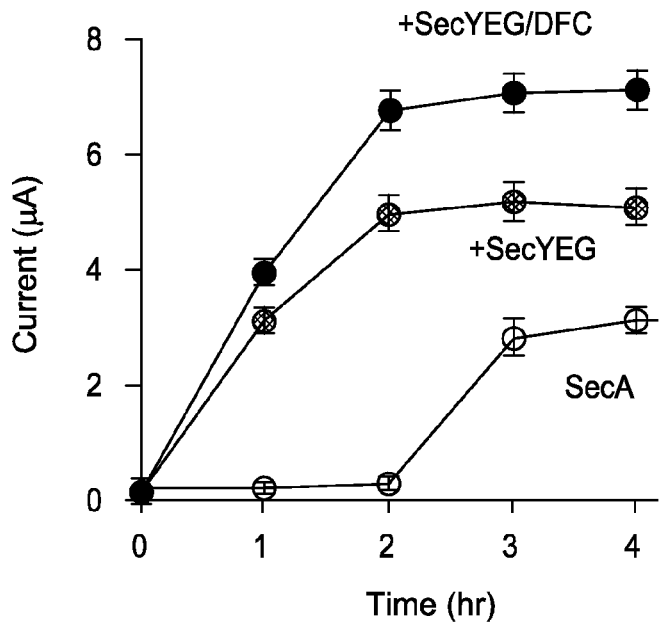

The SecA-liposome channels consisting of a single SecA protein with low efficiency and moderate specificity (9). Injection of reconstituted SecA-liposomes with either purified SecYEG (which by itself, in the absence of SecA has no channel activity), or SecDF•YajC enhanced the channel activity to levels that are equivalent to those found for the native BA13 membranes in oocytes (FIG. 3A). The reconstituted complexes also restored the specificity of the channel activity in the oocytes, which corresponded to the specificity of protein precursors translocation exhibited by the native BA13 membranes in oocytes (10). A Comparison of SecA-alone channels (i.e. absent all other complexes) with the channels of SecA-SecYEG and SecA-SecDF•YajC complexes eliminated the need for co-injecting ATP-$Mg^2$+ (see (10)). Moreover, detection of channel activity of the pre-assembled protein complexes in the oocytes was rapid, reaching max activity within 2 hours (FIG. 3B).

Example 3: Detection of SecA Channel Inhibition in Single Cells

Materials and Methods

SecA is essential for bacterial growth and serves as an ATPase for protein translocation across membranes. SecA also possesses intrinsic ATPase activity that is increased upon interaction with lipids, and further enhanced with protein precursors and SecYEG (11, 12). The conformational changes of SecA alter the sensitivities and affect differently on the various ATPase activity of SecA by SecA inhibitors, sodium azide (13) and Rose Bengal (14). SecA functions in the membranes, thus the inhibition of translocation ATPase by azide (13) and Rose Bengal correspond to the effect on protein translocation in E. coli system (14). To correlate these in vitro ATPase assays to physiological cellular conditions, the effective inhibition of channel activity in oocytes at sub-μM concentration by Rose Bengal (Table 2) also corresponded to the similar inhibition of SecA-dependent translocation ATPase and protein translocation with E. coli SecA system (14). The injection of liposomes reconstituted with SecA homologs allowed the similar assessments for other bacterial systems, which otherwise lack the homologs assays due to the strain specificity for translocation ATPase or protein translocation. RB was used as an example to test SecA-dependent channel activity sensitivity to inhibitors (Table 2).

Results

By injecting SecA-liposomes, or reconstituted with SecYEG or SecYEG-SecDF•YajC and various concentration of RB, the IC50 for their sensitivity to Rose Bengal was determined. The SecA-liposomes and the membranes depleted in SecYEG (Re-13 membrane) were about 10 times more sensitive to RB than those with SecYEG (Table 2). Suppressor mutant membranes (15, 16) was even higher: the RB IC50 for wild-type membrane was 4.7 μM and suppressor PrlA665 membranes at 100 μM; the removal of PrlA665 SecY rendered the sensitivity of reconstituted membranes to the same sensitivity of IC50 at 0.4 μM, while the IC50 was about the same with the addition of wild-type SecYEG. Thus the sensitivity of SecA channel activities is greatly influenced by the presence and the properties of SecYEG. The results from various bacterial channel activities were remarkably similar for BaSecA, SaSecA, and PaSecA reconstituted-liposomes (Table 2). The complex of EcSecYEG with various SecA homologs (with the exception of PaSecA) showed intermediate sensitivity to RB as compared to the SecA-liposome and membranes, indicating some interaction of SecA homologs with E. coli heterocomplex of SecYEG for the channel opening activities (Table 2). The addition of SecDF•YajC further increased the IC50 almost to the same extents with membranes. Thus, with proteo-liposomes injection methods, the channel activity of various SecAs and their interaction with SecYEG complex, and also of inhibition effects in single cells were determined.

(SaSecA1), P. aeruginosa (PaSecA) and B. anthraces (BaSecA1). Reconstituted liposomes were injected together with pOmpA and ATP-$Mg^{2+}$ as described. When indicated, SecYEG at 0.47 ng and SecDF•YajC at 0.53 ng were used for reconstitution, which were the same amount as in SecA-depleted BA13 membranes; Re-13.: Reconstituted membranes after removing SecYEG from B13 membranes. n=20-30.

Example 4: Determination of SecA Inhibitor Kinetics in Cells

Results

Figure 4A:
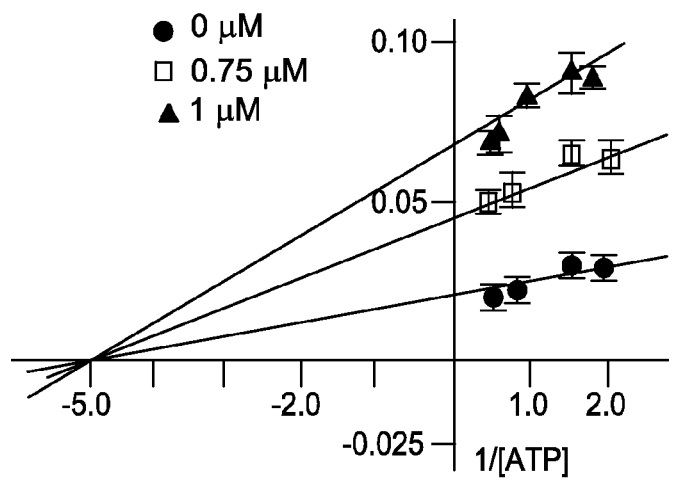
FIGS. 4A-4D.
Figure 4B:
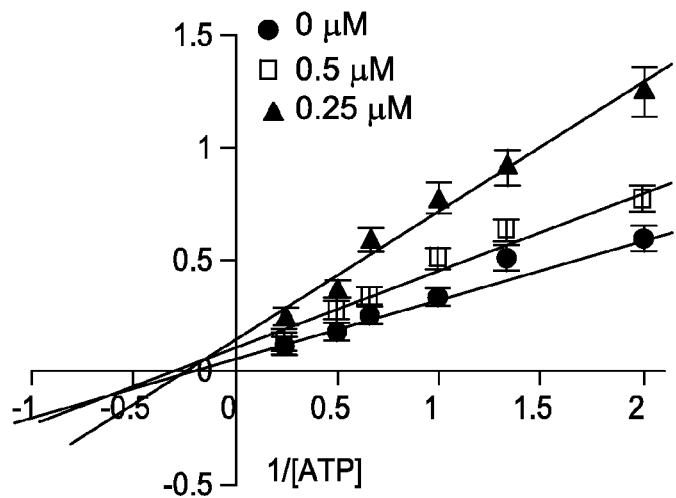
Figure 4C:
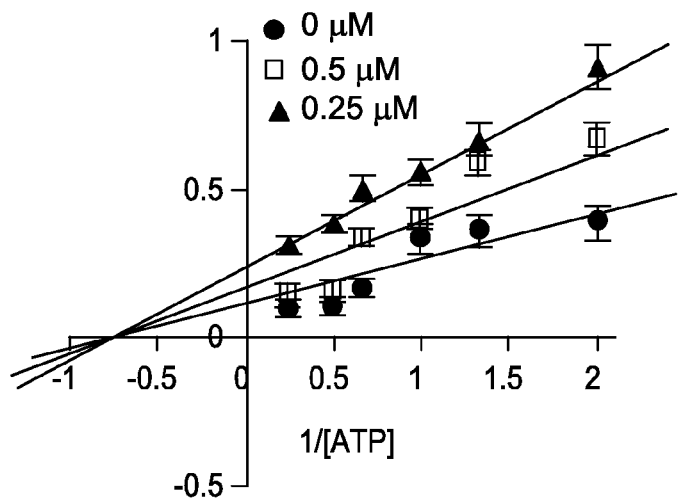
Figure 4D:
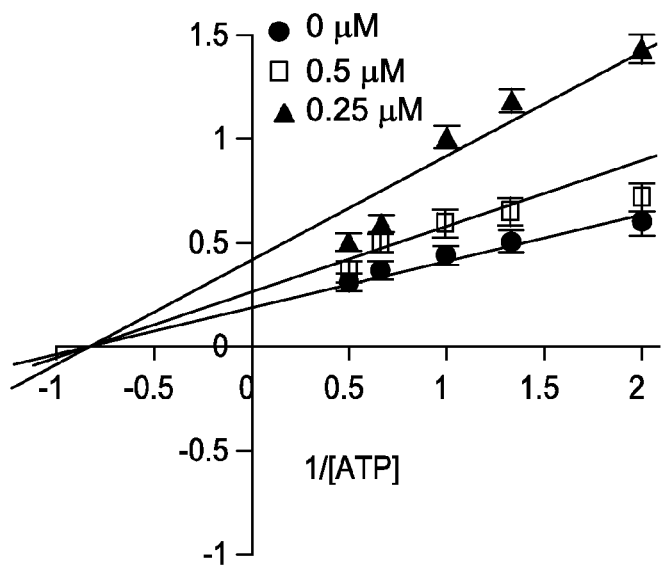

Soluble SecA intrinsic ATPase showed non-competitive inhibition at low ATP with RB, but competitive inhibition at high ATP (data not shown). SecA functions in the membrane, demonstrating that the E. coli SecA translocation ATPase (which requires SecYEG and precursors for high activity) was non-competitive with ATP in vitro (FIG. 4A). The channel activity on injected EcSecA-liposomes in the oocytes also showed similar non-competitive inhibition in regards to ATP (FIG. 4B). Since there is no suitable biochemical assay for translocation or translocation ATPase for those SecAs from different bacteria, the unique capability of this oocyte method is to address the inhibition mechanism and kinetics of ATP to different bacterial SecA. Using the injected SecA-liposomes in the oocytes, the RB also showed non-competitive inhibition with ATP for the channel activity for PaSecA (FIG. 4C) and SaSecA1 (FIG. 4D). Thus, this method allowed the monitoring of inhibitor kinetic activity which otherwise would not be possible.

Example 5: Hemi-Channel Activity of the Reconstituted Gap Junction Protein Cx26

Methods and Materials

Reconstitution of Cx26-Liposomes:

The E. coli liposomes treated with detergent were mixed with purified Cx26 protein at 10:1 ratio. Then the mixture was dialyzed in dialysis solution (0.25 M Sucrose, 0.4 M KOAC, 20 mM triethanolamine hydrocholoride pH7.5, 1.5 mM Mg(OAC)2 and 1 mM EDTA) at 4° C. for 15-18 hours to reconstitute the Cx-26-proteoliposomes.

Cx26-Liposomes Injection:

10 ng reconstituted Cx26-proteoliposomes was mixed with or without EGTA or $CaCl_2$ and injected into oocytes. The injected oocytes were incubated at 23° C. for 30 mins with 1.8 mM $CaCl_2$ to suppress the bubbling. Recording bath solution was 90K (90 mM KCl, 5 mM HEPES, 3 mM

TABLE 2

Rose Bengal $IC_{50}$ (μM) inhibition of SecA channel activity in oocytes.

| SecAs | Liposomes. | Lipo. + SecYEG | Lipo + SecYEG + SecDF•C | BA13 memb | Re-13 memb | RE-13 memb + SecYEG | RE-13 memb + SecYEG-DF•C |
|---|---|---|---|---|---|---|---|
| EcSecA | 0.4 | 3.0 | 3.8 | 4.7 | 0.4 | 4.2 | 4.4 |
| BsSecA1 | 0.3 | 3.1 | 4.5 | 5.8 | 0.5 | 5.0 | 5.2 |
| PaSecA | 0.3 | 1.1 | 2.0 | 5.1 | 0.3 | 5.1 | 5.1 |
| SaSecA1 | 0.4 | 3.1 | 4.2 | 6.1 | 0.5 | 5.6 | 5.0 |
| BaSecA1 | 0.3 | 3.3 | 4.0 | 6.1 | 0.5 | 5.0 | 5.3 |

The $IC_{50}$ of channel activities for Rose Bengal was determined with liposomes reconstituted with SecAs (120 ng) of E. coli (EcSecA), Bacillus subtilis BsSecA), S. aureus $MgCl_2$) without $Ca^{2+}$. For $Ca^{2+}$ inhibition, the $CaCl_2$ was added in the extracellular recording bath solution during the recording.

Results

Figure 5A:
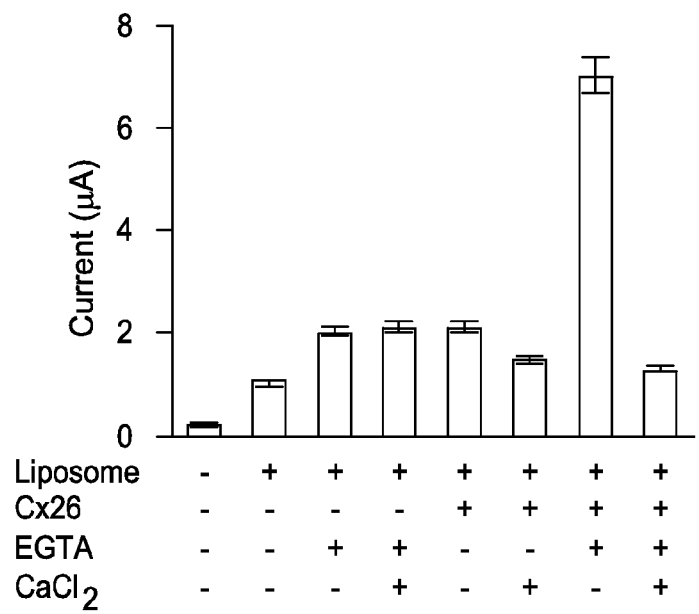
FIGS. 5A-5E.
Figure 5B:
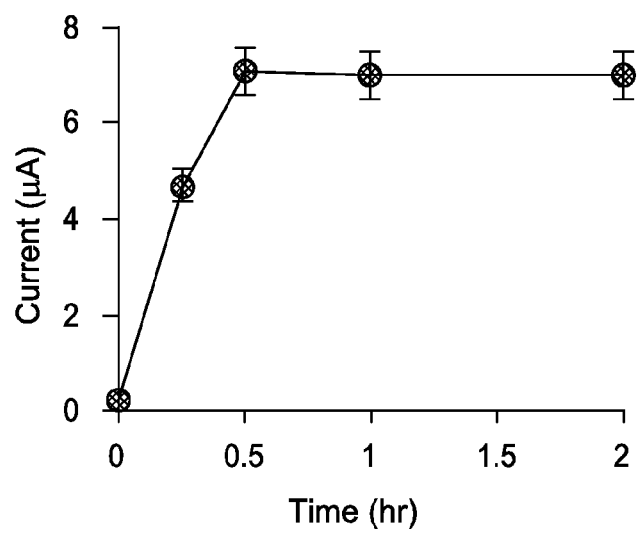
Figure 5C:
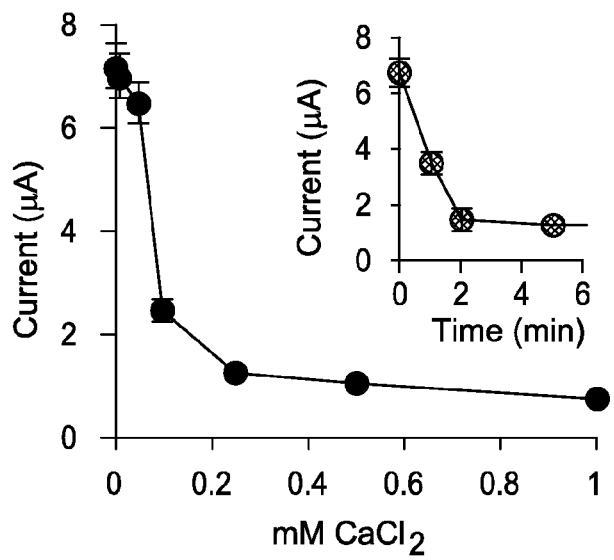

Application of the proteo-liposomes injection method was demonstrated for injection of oocytes with other complexed channel proteins. Gap junction membrane proteins are regulated by both intracellular and extracellular calcium (17). The hemi-channel activities have been monitored by injected cDNA into oocytes or dye permeability using liposome assembled proteins. In the current method of injecting proteo-liposomes, the Cx26 gap junction protein was purified from insect cell expression, and reconstituted with $E.$ $coli$ total lipids through dialysis to form Cx26 proteo-liposomes. The liposomes with or without purified Cx26 (10 ng) were injected into oocytes (with or without EGTA to chelate endogenous $Ca^{2+}$). As shown in FIG. 5, the hemi-channel activity was stimulated greatly to 7 µA by co-injection with 5 mM EGTA (FIG. 5A, lane 7); and $CaCl_2$ reduced the activity (FIG. 5A, lane 8). In contrast, liposomes alone yielded very small background current, and EGTA slightly increased the current, indicating there is small endogenous channel activity (FIG. 5A, lanes 2 and 3) that is $Ca^{2+}$-independent (lane 4). CX26-proteo-liposomes injection generated a small ionic channel activity around 2 µA, presumably in the presence of the endogenous $Ca^{2+}$ inside the oocytes. This activity was slightly inhibited by co-injection with 2 mM $CaCl_2$ (FIG. 5A, lanes 5 and 6). These results indicated that the channel activities were regulated by intracellular $Ca^{2+}$ concentrations. The channel activities in the injected oocytes could be observed within minutes of injection and reach maximum after 30 mins (FIG. 5B). It could be inhibited by further incubation of the injected oocytes with $CaCl_2$ in the extracellular bath solution. This inhibition was $Ca^{2+}$-dependent (FIG. 5C), and was rapid with the half-time of about 1 min (FIG. 5C, insert) that is consistent with previous reports using oocytes with DNA injection 18. These results showed that the Cx26 channel activity can be regulated by both intracellular and extracellular $Ca^{2+}$.

Figure 5D:
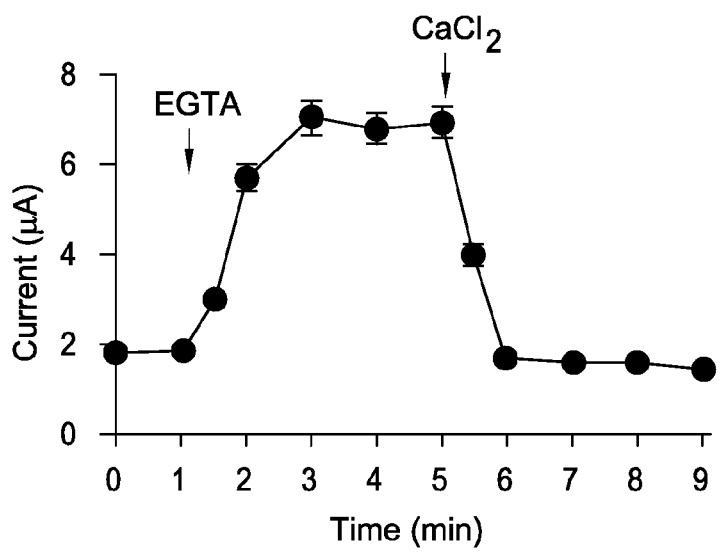

The ease of injection of reconstituted Cx26-liposomes and rapid detection of activity in the oocytes allowed further manipulation of monitoring channel activity. Since the effect of $Ca^{2+}$ is rapid and can be controlled with incubation of the injected oocytes in the extracellular recording bath solution, all $Ca^{2+}$-regulation from the same groups of oocytes was examined. Oocytes were first injected with Cx26-liposomes for 30 mins. The oocytes' channel activities were recorded, and then incubated extracellularly with 10 mM EGTA to induce the current, followed by adding excess $CaCl_2$ to regulate the channel activities (FIG. 5D). As expected, the currents of injected Cx26-liposomes alone were small at 2 µA, and it was stimulated to 7 µA by 10 mM EGTA in the extracellular recording bath solution (FIG. 5D). The chelating of endogenous $Ca^{2+}$ generated an expected increased ion current within 2 mins. The further addition of 30 mM $CaCl_2$ in the same extracellular bath solution drastically decreased the currents to 1.3 µA with 2 mins of incubation (FIG. 5D). These observations showed that $Ca^{2+}$ could regulate Cx26 channel activity extra-cellularly, and were compatible with the studies using cDNA injection as a tool but with much greater signal and in a controlled manner without limitation of long and variation expression level. Thus, the liposomes made of $E.$ $coli$ lipids are able to fold and assemble Cx26 to generate hemi-channel activity similar to that with cDNA injection, and may be used as a general method to study their channel function.

Figure 5E:
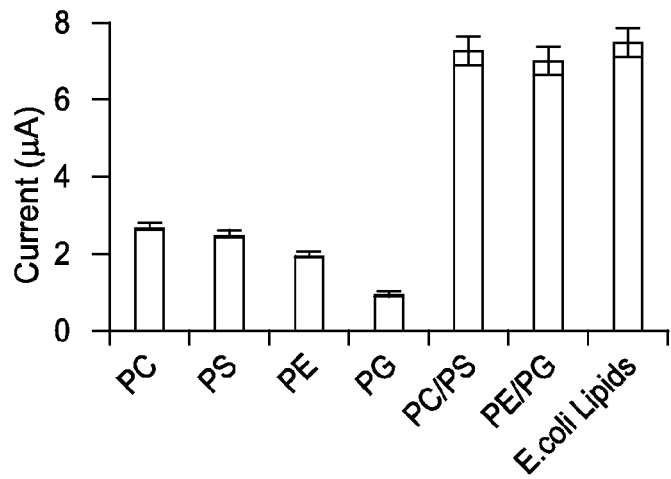

This method revealed which key lipid components are required for assembling Cx26 to achieve maximal channel activity. Previous studies showed that PC and PS at 2:1 ratio are required for the Cx26 channel activity (7). Thus, purified synthetic PC or PS liposomes reconstituted with Cx26 was used for channel activity with and without EGTA. The Cx26-proteoliposomes with PC or PS only generated small channel activity (FIG. 5E); however, with PC/PS at 2:1 ratio, the channel activity was similar to those liposomes reconstituted with $E.$ $coli$ lipids or synthetic PG/PE (FIG. 5E). Thus, adequate lipid compositions, such as PE/PG or PC/PS are important for achieve optimal channel activity of Cx26 hemi-channels.

Discussion of Results for Examples 1-5

A simple and efficient method to monitor channel activity for electrophysiological studies is presented. The method comprises direct injection of proteoliposomes instead of cDNA. Generally, expression usually takes 2-3 days with cDNA injection, and the expression rates are 20-30%. However, the proteoliposomes injection increases the expression time to within about 30 minutes to three hours. The efficiency is about 70-80%.

The advantages of such injection with proteo-liposomes for monitoring SecA channel activity are also evident. The basic characteristics of these oocytes SecA-channel activities have been verified with patch clamp and single channel recording without oocytes and are mostly supported by in vitro biochemical assays of protein translocation (9). SecA exists in soluble and membrane forms in $Escherichia$ $coli$ cells and serves as a motor ATPase to hydrolyze ATP as energy during the translocation to push the precursor protein across the cytoplasm (12, 22). The purified soluble SecA can insert into liposomes, and become integrate membrane proteins (23, 24). Moreover, upon interacting with anionic lipids, SecA forms ring-like pore structures that could serve as protein-conducting channels (21). Indeed, injecting SecA together with liposomes into oocytes elicits specific SecA-specific channel activities (9). The detection of SecA-liposome channel activity in the oocytes exemplified a big advantage of the injection of proteo-liposomes over the traditional injection of cDNA or mRNA methods which have been attempted with numerous efforts without success. It is clear now why previous attempts were not successful with SecA for several reasons. Without co-injection with anionic phospho-liposomes, SecA does not form ring structures (21) and does not elicit channel activity (FIG. 2B). Moreover, SecA alone channels require more ATP-$Mg^{2+}$, and higher concentrations of SecA to function (9). These requirements would have not been possible to meet in the simple injection of mRNA and cDNA in the oocytes.

These limitations may explain why no bacterial channel has been expressed in the oocytes; the proteo-liposomes injection may allow future studies of other bacterial channels. Moreover, the semi-physiological assays of channel activity in the oocytes allow the assessments of functional activities and inhibitors of SecA homologs from other bacteria that otherwise are not available. Another big advantage of the proteo-liposomes injection is the ability to reconstitute with interacting membrane complexes. The reconstituted SecA-liposomes with SecYEG-SecDF•YajC forms efficient supercomplex channels that are as efficient as in the native membranes in the oocytes (10, 23, 25, 26). The formation of such 7 components complex would have been difficult to accomplish with the traditional CDNA/mRNA methods. The incorporation of SecA-SecYEG-SecDF•YajC complex channels are also more efficient, faster and with higher current than SecA-alone channel. The proteoliposome assay allow the assessments of functional activities and inhibitors of SecA homologs from other bacteria that otherwise are not available.

The ratios of synthetic lipids are important for SecA channels: PG alone does not function. Proper ratios of PG/PC or PG/PE work well, however, the combination of PS/PE does not.

The proteoliposomes injection method was also investigated for application with other channel proteins. Cx26 is a gap junction protein which is regulated by calcium (Gerido et al., American Journal of Physiology: Cell Physiology, 2007, 293:C337-345). Previous studies used cDNA injection into oocytes and characterized its channel activity. The activity can be studied either hemi-channel in single oocytes or the whole channel by coupling two oocytes together for whole cell voltage recording.

In the current method, the Cx26 protein was purified, and reconstituted with $E.$ $coli$ total lipids through dialysis to form Cx26-proteoliposomes. The liposomes with or without Cx26 (10 ng) were injected into oocytes with or without EGTA for channel expression. Liposomes alone yields very small background current, and EGTA slightly increased the current, indicating there is small endogenous channel activity. This channel activity is not Ca2+-regulated.

CX26-proteoliposomes injection generated a small ionic channel activity around 2 µA presumably in the presence of the endogenous Ca2+ inside the oocytes: this activity was slightly inhibited by co-injection with 2 mM CaCl2. On the other hand, the channel activity was stimulated greatly to 7 µA by co-injection with 5 mM EGTA to chelate endogenous Ca2+. Co-injection of EGTA with CaCl2 reduced the activity. These results indicate that the channel activity is regulated by intracellular Ca2+ concentrations.

The observed channel activity in the injected oocytes could be observed within minutes of injection and reached a maximum after 30 mins. Inhibition of channel activity was shown to be Ca2+-dependent, and was rapid with a half-time of about 1 min.

Since the effect of Ca2+ is rapid and can be controlled with incubation of the injected oocytes in the extracellular recording bath solution, Ca2+-regulation from the same oocyte was investigated. First, the oocytes were injected with Cx26-liposomes and the oocytes channel activity recorded 30 mins later. The oocytes were then incubated extracellularly with 10 mM EGTA to induce the current, followed by adding excess CaCl2 to regulate the channel activities. The currents of injected Cx26-liposomes alone were small at 2 µA. The current was increase to 7 µA by addition of 10 mM EGTA in the extracellular recording bath solution, within 2 mins of addition. Addition of 30 mM CaCl2 in the same extracellular bath solution drastically decreased the current to 1.3 µA within 2 mins of incubation. These observations showed that Ca2+ regulated Cx26 channel activity extracellularly. The results were comparable with the study using cDNA injection as a tool. Thus the Cx26-proteoliposomes could generate hemi-channel activity similar to that with cDNA injection, and may be used as a general method to study their channel function.

Moreover, injection of the proteo-liposome further showed that the Cx26 channel can also be regulated by intracellular Ca2+. This phenomenon have not been clearly demonstrated since Ca2+ and EGTA cannot be easily manipulated with the injection of traditional cDNA or mRNA, as these conditions may affect the synthesis and assembly of Cx26 in the oocytes membranes.

Calmodulin (CaM) is considered one of the potential gap junction channel closers because of the co-localization of CaM and Cx32 (29), inhibition of CaM expression results in inhibition on CO2-induced gap junction uncoupling (28) and CaM-dependent $Ca^{2+}$ induced uncoupling of Cx50 gap junction channel (27). Therefore, the method can be used to investigate the role of CaM and intracellular calcium in regulating hemi-channel action.

Reconstituted Cx26-proteoliposomes (with synthetic PC or PS) only generated small channel activity in the presence of EGTA. However, reconstitution with a mixture of PC and PS at 2:1 ratio, the channel activity was stimulated to the levels compared to using natural $E.$ $coli$ lipids. The successful application of this method to probe the $Ca^{2+}$ regulation of gap junction Cx26 hemi-channel indicates the emergence of an assay for reconstituted membrane channel activity in general, and in illuminating gap junction regulation molecules in particular.

This method offers several advantages including: increased expression speed of the channel activity, the ability to investigate regulation of intracellular and extracellular $Ca^{2+}$, the small amount of preassembled proteins (only 10 ng Cx26 is needed), and a small number of oocytes can be used to generate statistically meaningful data.

The addition of gap junction regulators into the extracellular bath solution or direct injection of regulators into the oocyte together with Cx26-liposome can be easily accomplished and manipulated. With the proteo-liposome injection method described here, additional related issues, using lipid-protein interaction as an example, can be addressed. The presence of particular species of lipids in the surrounding membrane is required for proper activity of membrane channel (7). By reconstituting Cx26 into different liposomes, differential lipid dependence of the function of gap junction channel can be revealed using a more sensitive way instead of measuring permeability (7). In addition, this method can be correlated with protein structure study. The proteins applied in the structure characterization can be pre-tested for channel activity to assure that the membrane proteins are functional.

In summary, injection of reconstituted proteo-liposomes in the oocytes does not require protein of interest to be expressed from DNA thus shorten the time required for preparation. The method allows for monitoring channel activities for reconstituted liposomes with purified membrane proteins in a semi-physiological condition. The method also allows monitoring the channel activities of interacting membrane protein complexes and regulatory molecules or co-factors.

Example 6: Reconstitution of Efficient Ion-Channels

Materials and Methods
Liposome and Membrane Preparation

The preparation of liposomes is as described previously (Y.-h. Hsieh, et al., $J.$ $Biol.$ $Chem.$ 286:44702-44709 (2011)). Briefly, $E.$ $coli$ total lipids (Avanti) were dried, re-suspended in 150 mM KCl, and sonicated in an ice water bath until the solution became clear (usually for 3-5 min), resulting in an average size of liposomes about 130 nm. Samples of these liposomes were stored at −80° C. and thawed only once before use. BA13 SecA-depleted membranes were from $E.$ $coli$ BA13 cells grown at 42° C. to deplete the SecA [19]. $E.$ $coli$ 773 is an ompA-deleted strain; the OmpA-depleted 773 membranes were used for assaying proOmpA translocation. Inverted membrane vesicles were prepared using sucrose gradients as described previously.

Protein Purification

SecA was purified from BL21(λDE3)/pT7-SecA as described previously. ProOmpA was prepared as described previously. SecDF•YajC was purified from BL21(λDE3) cells containing plasmid pET543 secDF•yajC (from Dr. A. Driessen) as described. SecYEG was prepared from *E. coli* BL21(λDE3) strain harboring pBAD/secEhisYG (from Dr. F. Duong) and purified as described. Briefly, cell-free lysates were passed through a Ni-NTA affinity column (QIAGEN®), the Sec-YEG fractions were further purified by a SP-Sepharose cation exchange chromatography (GE Healthcare). SecYEG complex was eluted at 300-400 mM NaCl in Tris-HCl pH 7.9 buffer containing 1% Triton X-100, 10% glycerol and 1 mM DTT; samples were stored at −80° C. in the same buffer until use. The Sec-YEG and SecDF•YajC complexes were more than 90% pure as revealed by Coomassie Blue Stain or Silver Stain after SDS gel electrophoresis.

In Vitro Protein Translocation

The translocation of pOmpA into liposomes is as described previously (Y.-h. Hsieh, et al., *J. Biol. Chem.* 286:44702-44709 (2011)). SecYEG and SecDFC were diluted in $H_2O$ at 10-20× before reconstituting into sonication-prepared liposomes. Reconstituted liposomes, SecA and pOmpA were added to the translocation buffer (Y.-h. Hsieh, et al., *J. Biol. Chem.* 286:44702-44709 (2011)) separately. Liposomes (10 μg) or OmpA-deleted 773 membranes (3.5 μg) with 10 μg or indicated amounts of SecA were used in 0.1 ml translocation mixtures (Y.-h. Hsieh, et al., *J. Biol. Chem.* 286:44702-44709 (2011)). The reactions were at 37° C. for 45 min, and the mixtures were processed for immunoblots as previously described (Y.-h. Hsieh, et al., *J. Biol. Chem.* 286:44702-44709 (2011)).

*Xenopus* Oocyte Preparation and Injection

Oocytes were obtained from live frog *Xenopus laevis* (XENOPUS EXPRESS™ Xenopus Express, Inc) and injected with sample mixtures as described previously. Briefly, the 50 nl sample mixtures were injected into dark pole site of oocytes using Nanoject II injector (Drummond Scientific Co., Broomall, Pa.). The effective concentration of each component was based on the average volume of 500 nl oocytes. The ion current was recorded after three hours of incubation at 23° C. Unless otherwise noted, the amount for each component is 120 ng liposomes, 120 ng SecA, 14 ng proOmpA, 2 mM ATP, and 1 mM $Mg^{++}$ and where indicated, 0.47 ng of Sec-YEG and 0.53 ng of SecDF•YajC.

Voltage Clamp Measurement

The voltage clamp adapted from an electrophysiological method was used to measure the opening of protein conducting channels as described previously. The current was recorded after 3 h of incubation after injection at 23° C. Inward currents and outward currents were recorded to measure the net currents for channel opening.

Protein Quantification

Figure 8:
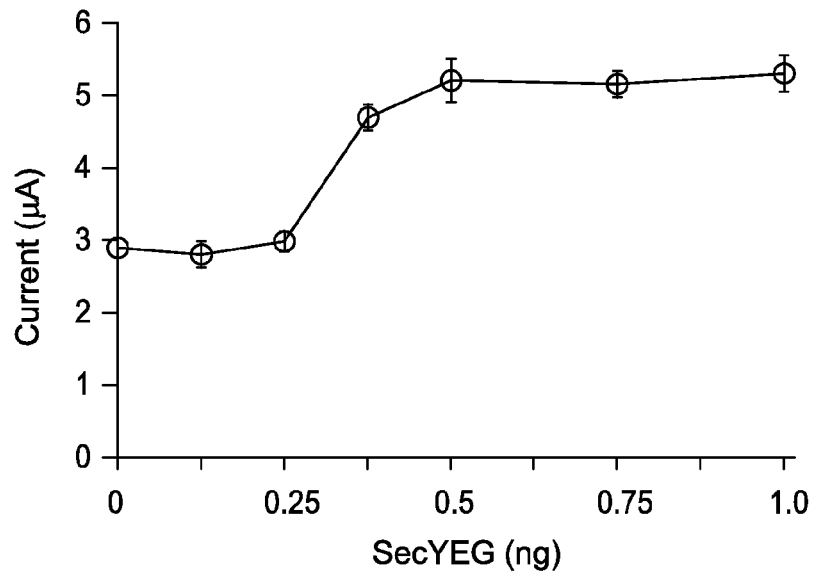
FIG. 8 is a line graph showing the ion-channel activity, measured in μA, of various quantities of SecYEG (0-1 ng) in oocytes. For dose-dependent enhancement of SecA-liposome channel activity in the presence of SecYEG, 120 ng SecA-liposomes with ATP-Mg was injected in the presence of 0-1 ng purified SecYEG.
Figure 9A:
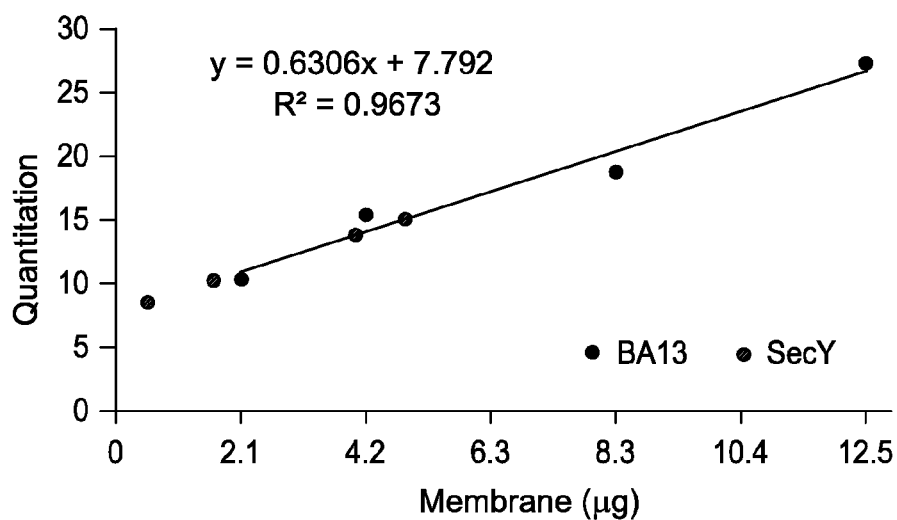
FIGS. 9A-9B.

Protein amounts were estimated from A280/A260 ratios, and confirmed by Bradford assay (Bio-Rad) using BSA as standards or by SDS-PAGE with sliver staining using BSA as standards. The relative amounts of purified SecYEG and SecDF.YajC compared to the membrane were determined by immunoblots with SecY and SecF antibodies. The amounts were quantitated by Bio-Rad Quantity One software and were fitted by linear regression (FIGS. 8 and 9).

Results

SecA-liposomes alone are capable of promoting protein translocation in vitro and for eliciting ion channel opening activity in the oocytes (Y.-h. Hsieh, et al., *J. Biol. Chem.* 286:44702-44709 (2011)). However, the SecA liposomes require increased amounts of SecA, and additional ATP-Mg for channel activity; and even then the activity is only about 50% of the native membranes (Y.-h. Hsieh, et al., *J. Biol. Chem.* 286:44702-44709 (2011)). Since SecYEG plays a role in the channel efficiency, the SecYEG dose titration assay was performed to determine its relation with channel activity in the SecA liposomes (FIG. 8).

Figure 6A:
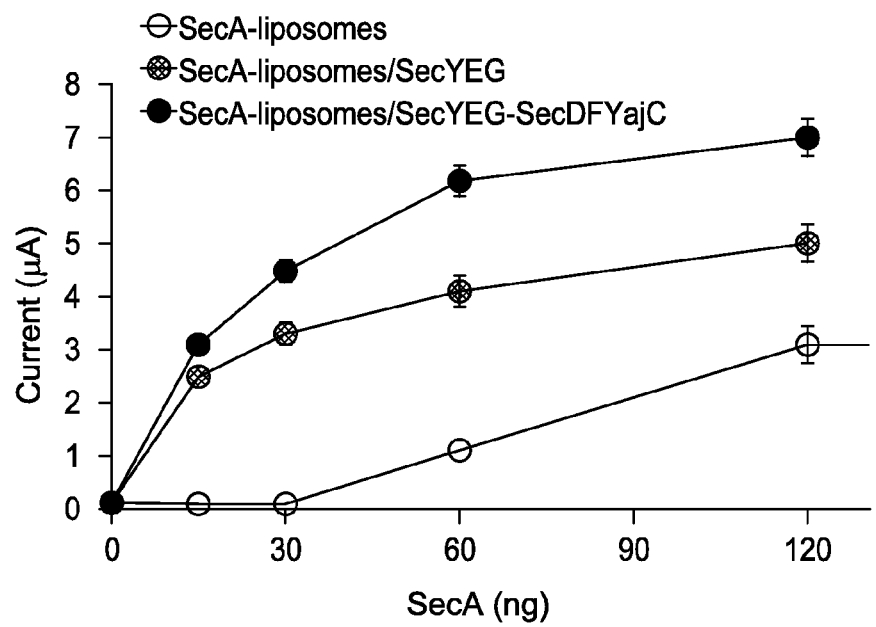
FIGS. 6A-6C.

With 120 ng SecA-liposomes, 0.47 ng of Sec-YEG increased the ion-channel activity from 3 μA to 5 μA. Additional SecYEG failed to facilitate the channel activity further. However, the ion-channel activity of SecA-SecYEG liposomes is only about 70% of native membrane vesicles containing intrinsic SecYEG, suggesting that other membrane proteins or factors may be required for a fully functional ion-channel activity. Thus, other Sec accessory proteins which may play a role for efficiency, such as YidC or SecDF•YajC were tested. Purified YidC had no additional activity (data not shown). SecDF•YajC have been shown to interact with SecYEG and to regulate the SecA membrane cycling and to maintain proton motive force during the later steps of protein precursors translocation in the cells. SecDF•YajC, like SecYEG by themselves, were not active for channel activity without SecA (FIG. 6A, and data not shown). Addition of SecDF•YajC further enhanced the channel activity of SecA-SecYEG (FIG. 6A). The increase of activity of SecA-liposomes was more pronounced at lower concentrations of SecA (FIG. 6A). Conversely, in the presence of SecYEG and/or SecDF•YajC, less SecA was required to achieve the same level of channel activities (FIG. 6A). Thus, in SecYEG reconstituted liposomes, 15 ng SecA was sufficient to activate the SecA-liposomes channel activity which otherwise requires 120 ng SecA. Moreover, previous studies showed that the SecA-liposomes need additional ATP-Mg to elicit channel activity in the oocytes (Y.-h. Hsieh, et al., *J. Biol. Chem.* 286:44702-44709 (2011)), even though there is sufficient ATP in the oocytes to support the channel activity with native membranes containing SecYEG.

Figure 6B:
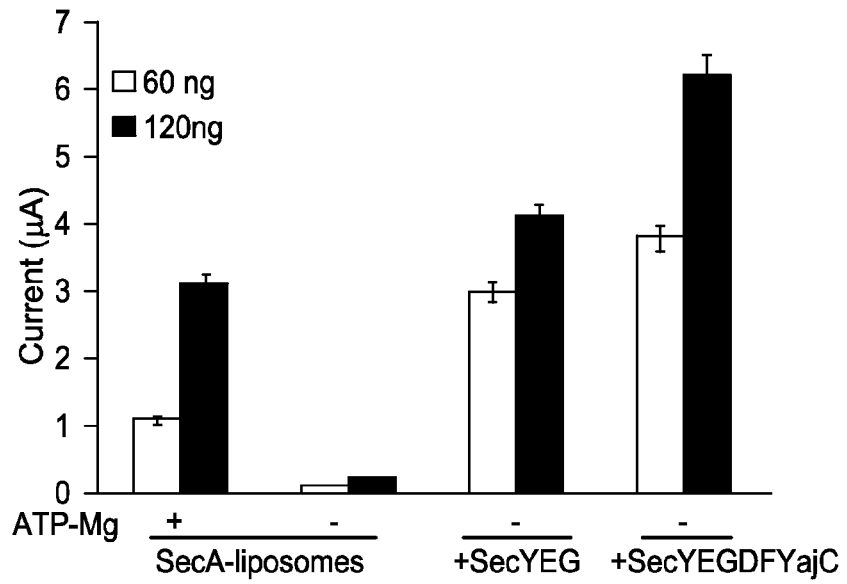
Figure 6C:
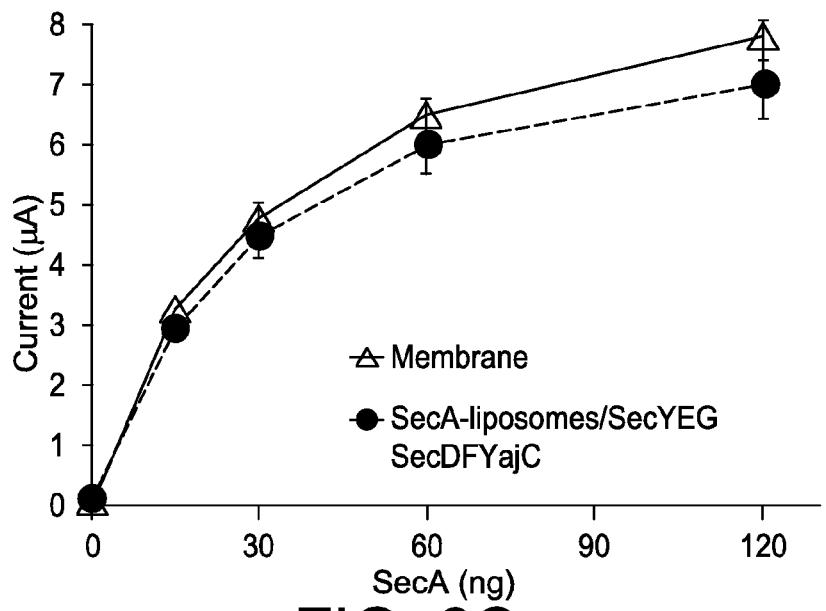

The data disclosed herein demonstrate that additional ATP-Mg was no longer required in the presence of 0.47 ng of SecYEG and/or 0.52 ng of SecD•YajC for SecA-liposomes to function as ion-channels in the oocytes (FIG. 6B). These data show that SecA-SecYEG liposomes not only regain the signal peptide recognition function but also increase the ion channel efficiency. It is further noted that for the liposomes to function, SecA was in excess over SecYEG, consistent with the findings that there are more SecA than SecYEG in the cell. Indeed, the channel activity of SecA-SecYEG complex together with SecDF•YajC was comparable to that of native membranes containing SecYEG (FIG. 6C). These data indicated that the reconstituted proteo-liposomes with SecYEG SecDF•YajC were almost fully functional as native membranes for ion-conducting channels.

Figure 9B:
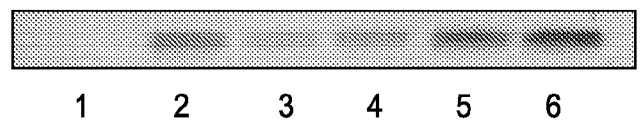

To assess the amount of SecYEG used for reconstituted proteo-liposomes, the amount of SecY (FIG. 6C) was quantified by Western immune blots as described in the Methods (FIG. 9B). Based on the linear equation generated from native membrane vesicles, the amount of purified SecY needed to achieve >90% activity (FIGS. 6C, 7A and 8B) was only ⅙ of that membrane used in the assays. Increasing Sec-YEG and SecDF•YajC to equivalent amounts found in native membranes marginally improved the channel activity (data not shown). Thus SecA liposomes, when reconstituted with SecYEG and SecDF•YajC, maintain ion channel activity that is almost equivalent to native membranes containing these same components, under the condition that proton motive force is not a factor.

Example 7: Reconstitution of Efficient Protein Translocation Channels Results

Figure 7A:
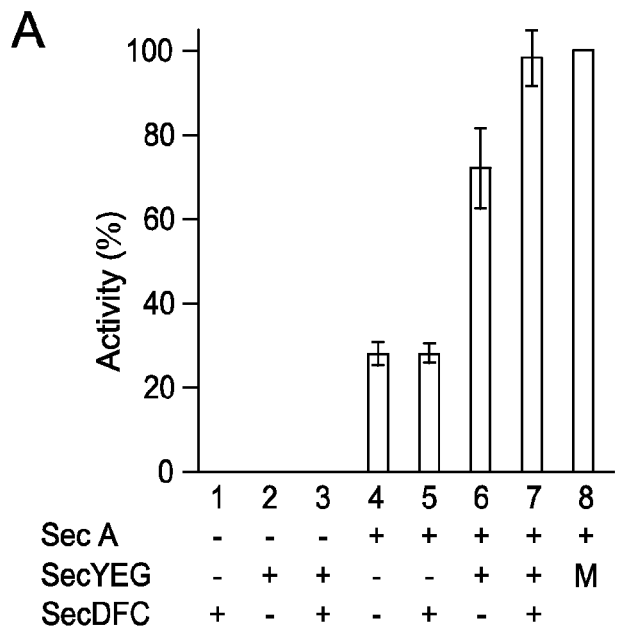
FIGS. 7A-7B.

Previous work (Y.-h. Hsieh, et al., *J. Biol. Chem.* 286: 44702-44709 (2011)) has showed that SecA-liposomes can promote protein translocation. However, such SecA-liposomes lack signal peptide specificity because unfolded OmpA, without signal peptide, can also be translocated (Y.-h. Hsieh, et al., *J. Biol. Chem.* 286:44702-44709 (2011)). Moreover, such SecA-liposomes are far less efficient, requiring considerably more SecA to achieve only 50% of the translocation activity when both SecA and SecYEG are present. As shown previously, addition of SecYEG to the SecA-liposomes enhanced translocation activity (FIG. 7A, Lane 6). More importantly, the translocation activity of the variously reconstituted liposomes was almost able to reach the same level as that of native membranes: from ~30% translocation of SecA-liposomes (Lane 4) to 75% with SecA-SecYEG (Lane 6), when compared to native membranes (Lane 8). In addition, as with ion channel activity, the efficiency of proOmpA translocation is also increased to more than 97% when SecDF•YajC is reconstituted with SecA-SecYEG-liposomes (FIG. 7A, Lane 7). It is also worthy of note that SecYEG (FIG. 7A, Lane 2) and SecDF•YajC (Lanes 2-3), absent SecA, is not active, and that SecDF•YajC (in the absence of SecYEG) exhibits no additional activity with SecA-liposomes (Lanes 4, 5).

Figure 7B:
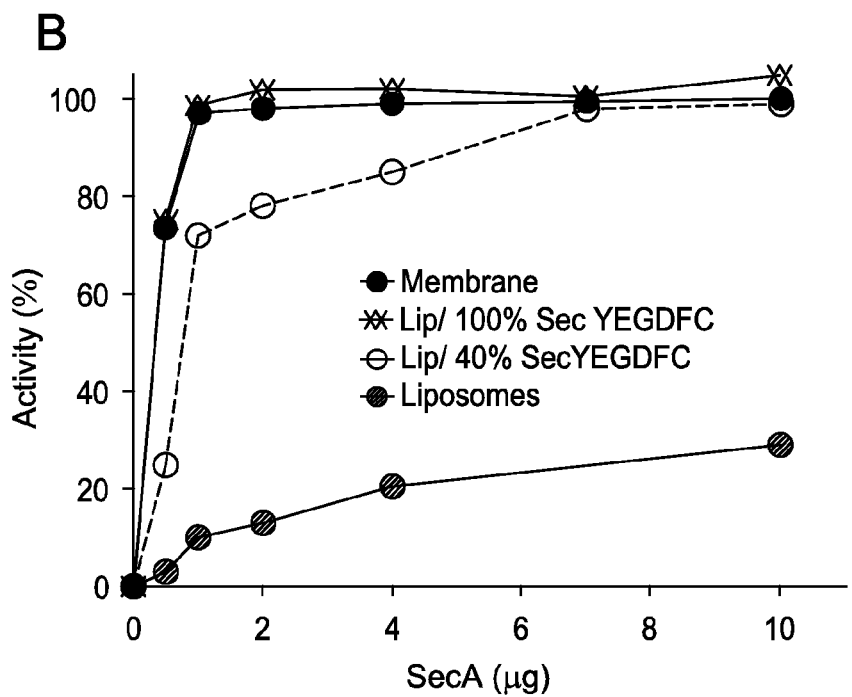

Efficiency of the reconstituted liposomes was examined in view of the requirements of SecA in the translocation of proOmpA. Much less SecA was needed to more efficiently translocate pro-OmpA by SecYEG-SecDF•YajC-liposomes (FIG. 7B, asterisk*) than with SecA-only liposomes (FIG. 7B, open circle). These effects are much more pronounced at low SecA concentrations, and are also dependent on the amount of SecYEG in the reconstituted liposomes. The SecYEG complex used in the translocation contained only about 40% of SecY in the membranes (FIG. 7A, Lane 8); there was an appreciable difference in the efficiency of proOmpA translocation at the lower concentration of SecA (FIG. 7B). However, when similar amounts of purified SecYEG were used in the liposomes as were present in the membranes (FIG. 7B, closed circle), decreasing the concentration of SecA had virtually no effect on the efficiency of proOmpA translocation between the reconstituted SecYEG-SecDF.YajC and membrane vesicles (FIG. 7B). Thus, the reconstituted SecA-liposomes with both SecYEG and SecDF•YajC function almost as efficiently in ion-channel activity (FIG. 6C) and protein translocation (FIG. 7B) as do in the native membrane protein-conducting channels. It is noted that the protein-conducting channel of the reconstituted proteo-liposomes does not contain signal peptidase, thus the signal peptide is not cleaved from the translocated proOmpA. Nevertheless the translocation of precursors by reconstituted channels is almost fully functional as native membranes containing SecYEG-SecDF•YajC.

Discussion of Results for Examples 6 and 7

Tsukazaki et al. recently reported the fine structures of SecDF from *Thermus therphilus*, and identified an ATP-independent step in protein translocation that requires both SecDF and proton motive force in a pH-dependent manner. They proposed that SecDF serve as membrane integrated chaperones, driven by proton motive force to achieve ATP-independent protein translocation. While it has previously been shown that SecDF regulates the proton motive force during the translocation process, which is precursor specific, the proton motive force by SecDF•YajC has little effect on proOmpA translocation when ATP is saturated in assays. The data disclosed herein demonstrate SecDF•YajC enhances translocation of proOmpA and the ion-channel activity of SecA-liposomes in the presence of SecYEG with sufficient ATP and constant pH, under which proton motive force does not play an important role; indeed, SecDF•YajC itself has no channel activity without SecYEG. Hence, under the conditions used here, SecDF•YajC is able to enhance translocation of proOmpA through a mechanism other than proton motive force.

The evolution of the Sec components and pathways has been reviewed. Previously, some of the evolutionary implications of having two SecA-dependent protein-conducting channels in membranes: the low-affinity SecA-only channels and high-affinity SecA-SecYEG-channels [40-44], which now should include SecDF•YajC. In demonstrating the conversion of low-affinity channels to high-affinity channels these data effectively mimic a form of in vitro molecular evolution. It should be emphasized again that SecYEG liposomes even with SecDF•YajC are not active in translocation, while SecA-liposomes are active, albeit with lower efficiency and specificity, much like Prl suppressors. It is reasonable, therefore, to consider again the question of whether the two SecA-dependent protein-conducting channels have evolved independently or that SecA started as the basic primitive core channels, and evolved (with the recruitment of Sec-YEG-SecDF•YajC) to form the more efficient and more specific channels that are found today: much like the development of a number of amino acid transport systems in bacteria, as well as the recruitment of various sigma factors by RNA polymerase. Though this evolutionary argument is philosophical and difficult to prove experimentally, it is tempting to speculate that SecAalone channel was the most primitive prototype channel. The SecA-alone channel promotes ion-channel activity translocation of proteins even without signal peptides and no other membrane protein in a process that requires only ATP but was inefficient and with low specificity, like PrlA suppressors. Such channel would have then gained increased efficiency and specificity with the addition of SecYEG-SecDF•YajC. Presently, both types of channels are functional in bacteria (with SecA analogs still present in chloroplasts), which provide an energy-rich environment that enables both types of channels to function under rapid growth conditions. The high ATP requirement for SecA to function as both a motor and a core channel protein may have ultimately led to its evolutionary extinction in higher organisms, which primarily employ SecYEG analogs with the Sec61 complex. In these more highly evolved complexes the co-translational secretion derives the necessary energy from protein synthesis and thus does not require SecA-mediated ATP hydrolysis to cross the membranes.

In summary, this work shows that SecA-liposomes reconstituted with SecYEG-SecDF•YajC are as fully functional as native membranes in protein-conducting channels for protein translocation and ion-channel activity. Moreover, this study also establishes that the low-affinity SecA-channels can be transformed into higher efficient high-affinity SecA-SecYEG-SecDF•YajC channels with higher specificity.

Example 8: Phospholipids Induce SecA to Form Lipid-Specific Domains as Revealed by Limited Proteolysis Methods and Materials
Bacteria Strains BA13, a secA13(am) supF(ts) mutant and MC4100 were from D. Oliver. *E. coli* RR1/pMAN789-Ns and pMAN789-Cs were from S. Mizushima, *E. coli* PS289 (MC1000, leu+, ara+, phoAΔPvuII, pcnB80, zadL::Tn10 (Tcs Strr), secEΔ19-111, recA::cat/pBAD22 secE+) and its wild-type *E. coli* MC1000 were from C. Murphy and J. Beckwith. The rabbit region-specific SecA antibodies, A2 (SecA 211-350) and A5 (SecA 665-820), were prepared from the plasmid constructs from D. Oliver.

Buffers and Media

The following buffers were used where indicated: DTK buffer (1 mM, dithiothreitol, 10 mM Tris-HCl, pH 7.6, 50 mM KCl); DTKM buffer [1 mM dithiothreitol, 10 mM Tris-HCl, pH 7.6, 50 mM KCl, 10 mM Mg(OAC)2]; DE20 (1 mM DTT, 20 mM EDTA); LinA and MinA media were prepared as described.

Biochemicals

Gel media for protein purification (S-SEPHAROSE®, Q-SEPHAROSE®, and SEPHACRYL® S-300) were from GE Pharmacia Biotech Inc. Trypsin, treated with Na-p-tosyl-L-lysine chloromethyl ketone, and all other chemicals are reagent grade, unless indicated otherwise, obtained from Sigma. [$^{35}$S] protein labeling mix (Expre [$^{35}$S] [$^{35}$S], 1175 Ci/mmol) was from DuPont NEN. The plasmid pET-5a was from Promega. The lipids were from Avanti Polar Lipids, Inc; CL, Cardiolipin (Heartdisodium salt) in chloroform; EM, *E. coli* total lipid extract in chloroform; PE, L-α-Phosphatidylethanolamine (*E. coli*) in chloroform; PG, 1,2-Dioleoyl-sn-Glycero-3-[Phospho-rac-(1-glycerol)] (sodium salt) in chloroform and PC, 1,2-Dioleoyl-sn-Glycero-3-Phosphocholine powder).

Purification of [$^{35}$S]SecA

[$^{35}$S]SecA was purified from BL21(λDE3)/pT7-secA according to procedures described previously. Cells were grown in MinA medium at 37° C. IPTG (0.5 mM) was used to induce SecA overexpression at O.D.600 of 0.5. After 10 min, [$^{35}$S] protein labeling mix was added (1 mCi/liter) and the culture was incubated for an additional 2 hrs. The harvested cells were washed once with DTKM buffer, resuspended in DTKM buffer containing 5 µg/ml DNase and 0.5 mM PMSF, and lysed by passing through a French Press at 15,000 psi. The cell lysates were centrifuged at 8,000 rpm for 15 min. to remove the debris, followed by another centrifugation at 55,000 rpm for 90 min in a Beckman Ti-70 rotor to remove ribosomes and membranes. The supernatant S100 was loaded onto an S-Sepharose column equilibrated with 25 mM phosphate buffer, pH 6.4, and was eluted by a NaCl gradient. [$^{35}$S]SecA was eluted at 0.3 M NaCl. The fractions containing [$^{35}$S] SecA were precipitated with ammonium sulfate. The pellet was then dissolved in 0.15 M ammonium bicarbonate buffer and loaded onto a Sephacryl S-300 column. The final SecA product was virtually pure, as determined by SDS-PAGE and visualized by autoradiography.

Preparation of Inverted Membrane Vesicles

Membrane vesicles from *E. coli* MC1000, MC4100 and SecA amber mutant, BA13, were prepared by standard membrane preparation procedures. SecE-depleted membrane was prepared from SecE mutant strain PS289 according to procedures previously described. The amount of SecA, SecY, SecE and SecG were determined by immunoblots (The SecE-depleted membranes used in the preparation contained SecE<1%; SecY<1%; SecG 1%; SecA 650%, as compared to MC1000 normal membranes).

Liposomes Preparations 1 mg of lipids (in chloroform) were dried in a speed vacuum (Automatic Environment SpeedVac system AES1010-120), resuspended in 50 µl of 50 mM Tris-HCl (pH 8.0) buffer, and sonicated (output at 6 with SONIFIER® 450 by Branson Ultrasonics Corporation from VWR Scientific Company) in a water bath at 4° C. for 15 min. PC/PE– was mixed at 1:1; PC/PG, PC/CL PE/CL and PE/PG: were mixed at ratios of 3:1.

Purification of SecA and Truncated SecA Proteins

*E. coli* was purified from BL21(λDE3)/pT7-secA, cultured at 37° C. in LinA medium supplemented with 0.5% glucose, and induced with IPTG (0.5 mM) at O.D.600 of 0.5. The culture was incubated for additional 2 hrs. Other procedures were the same as that of [$^{35}$S] SecA, as previously described. N95, C34 and C28 were similarly purified from soluble fractions using S-Sepharose column and followed by gel-filtration. C95 was purified according to Breukink et al, and N53 and N39 were purified according to Matsuyama et al. The cloned M48*-kDa (344-810) with 6 His-tag in C-terminal was PCR amplified from pT7SecA with the addition of NdeI and BamHI and ligated into pET-5a. It was then treated with the same enzymes. The PCR primers were 5'-primer: GCT CAT ATG CAG GGC CGT CGC TGG TCC G (SEQ ID NO:1). 3'-primer: GGA TCC TTA ATG ATG ATG ATG ATG ATG CAT GGA GAA CGA TTC ACG (SEQ ID NO:2). The cloned M48*-kDa was over-expressed in BL21 (λDE3) strain and purified with Ni-NTA agarose (QIAGEN®) according to the manufacturer's instructions.

Purification of CvaA Protein

The gene of cvaA was cloned by PCR. His6-tag was added to its C-terminus. Primers for cvaA gene were 5' forward (GGGAATTCCATATGTTTCGCCATGAT GCTTTAGAAAAC (SEQ ID NO:3)) and 3' reverse primer (CCGGAATTCTTAATGATGATGATGA TGATGTCATTGATCGGTCCTGTTGCACTGTG (SEQ ID NO:4)). The gene of cvaA was inserted into the pET-5a vector to yield pET5a/cvaA. *E. coli* HMS174 containing pET5a/cvaA was grown in LinA medium supplemented with 0.5% glucose and ampicillin (100 µg/ml) at 37° C. Then 0.5 mM IPTG was added at OD600 of 0.6. Cells were harvested after 2 hrs of further incubation. CvaA was overproduced as insoluble inclusion bodies and purified following the manufacturer's protocols (Xpress™ System Protein Purification provided by Invitrogen Corporation).

Sequencing of SecA Fragments

SecA (10 µg) and N95 (10 µg) were digested with trypsin at 1 µg/ml on ice for 15 min in 100 µl DTK buffer in the presence or absence of lipids (20 µg). The reaction was stopped with 10% TCA. SecA fragments were separated by SDS-PAGE, transferred to PVDF membrane sheets, and visualized by Coomassie Blue staining. Individual bands were then excised from the PVDF membrane sheets and subjected to N-terminal peptide-sequencing analysis by Edman degradation in the Core Facility of Biology Department, Georgia State University. When the excised band contained multiple peptides, all possible amino acids were called and aligned against the known sequences of SecA.

Proteolysis of Soluble and Lipid-Integrated SecA

Trypsin at the indicated amounts was added to DTK buffer containing SecA in the presence or absence of various lipids, (or ATP, or AMP-PNP as indicated) and incubated on ice for 15 min. The reaction was stopped with an equal volume of 20% cold TCA and incubated on ice for 30 min.

The precipitates were recovered by centrifugation at 14,000 rpm for 10 min in a table-top centrifuge, washed with 1 ml of cold acetone, and air dried. SecA fragments were then separated by SDS-PAGE, and visualized either by Coomassie Blue staining or by Western blotting with anti-SecA rabbit serum after being transferred to polyvinylidene difluoride (PVDF) membrane (PROBLOTT®; Applied Biosystems, Inc.).

Stabilization of Membrane Proteins in M48 Formation

[$^{35}$S] SecA (1 µg) was incubated with liposomes (20 µg) prepared from *E. coli* lipid mixtures, in the presence of various amounts of proteins including BSA, CvaA, N39, N53, C28 or cytochrome C oxidase (a gift of C. A. Yu), in 100 µl of DTK buffer (pH 8.0) at 37° C. for 15 min. After chilled completely on ice, the reaction mixtures were treated with 20 µl of trypsin (final concentration, 30 µg/ml) on ice for 15 min, and stopped by the addition of cold 10% TCA. SecA fragments were separated by SDS-PAGE. The resulting gels were dried and exposed to KODAK® (Rochester, N.Y.) BioMax MR-1 film for autoradiograms. The lipid specific [$^{35}$S] M48 band was quantified by QUANTITY ONE® software (Bio-Rad Laboratories, Inc.).

Results

Soluble SecA integrates into membrane vesicles upon interaction with membranes. Two distinct, membrane-integrated forms of SecA have been revealed by the presence of proteolysis-resistant fragments: one N-terminal 68-kDa fragment that resembles the one produced by limited proteolysis of soluble SecA, and the other M48 that starts at glutamate residue 361. These fragments are specific to SecA in the presence of membranes without protein translocation. To examine the effects of phospholipids on SecA conformation, the proteolytic profiles of SecA in the presence and absence of phospholipids were analyzed. FIGS. 10A-10E are images of protein electrophoresis gels and immune-blots showing proteolysis patterns of soluble SecA and various phospholipids-associated SecA.

The overall sensitivity of SecA to low concentrations of trypsin differed little in the presence or absence of liposomes prepared from *E. coli* lipids. However, the profiles of proteolytic fragments, as determined by SDS-PAGE, were distinct (FIG. 10A): at 1-3 µg/m of trypsin, soluble SecA gave rise to a major N-terminal 68-kDa band and several smaller fragments, including a 50-kDa fragment (FIG. 10A, lanes 3, 4) having an N-terminal sequence of 9VFGSRN (SEQ ID NO:5) (Table 3).

Figure 10A:
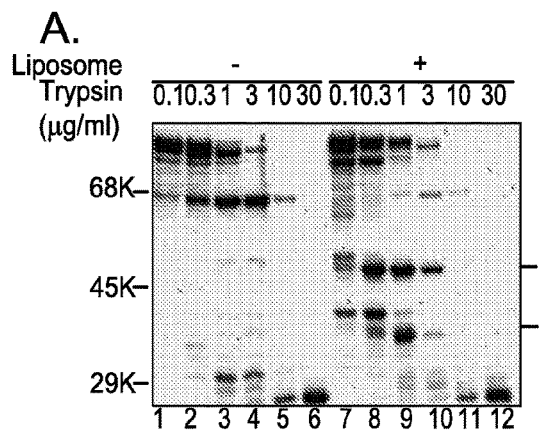
FIGS. 10A-10E.
Figure 10B:
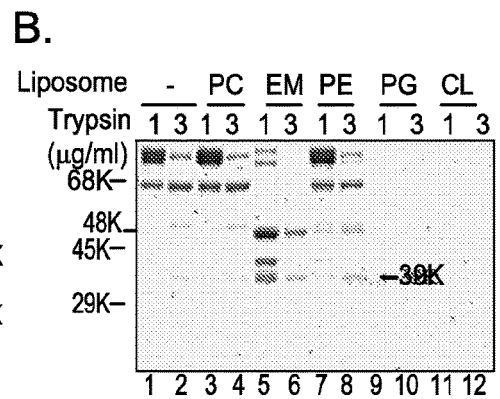
Figure 10C:
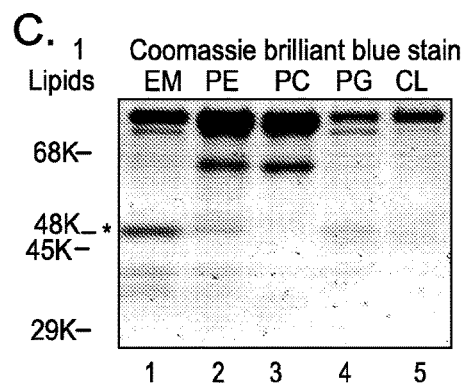
Figure 10C:
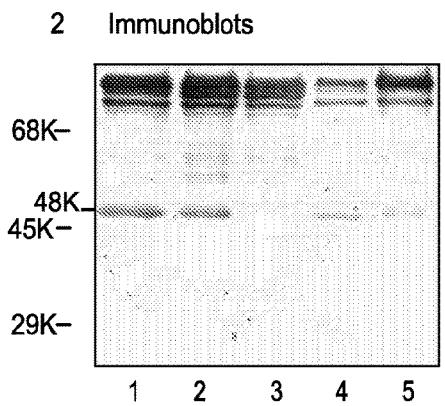
Figure 10D:
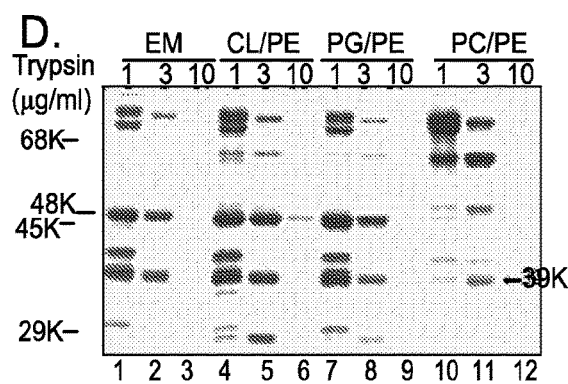
Figure 10E:
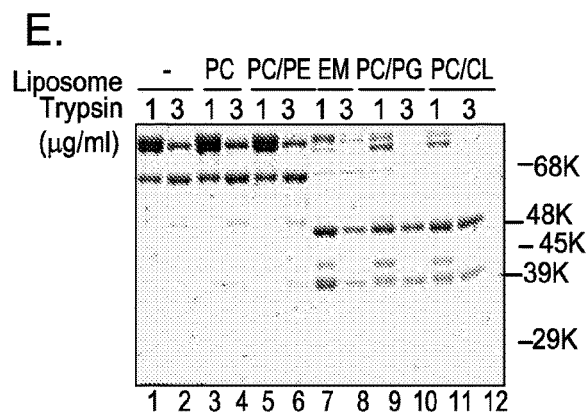
Figure 14A:
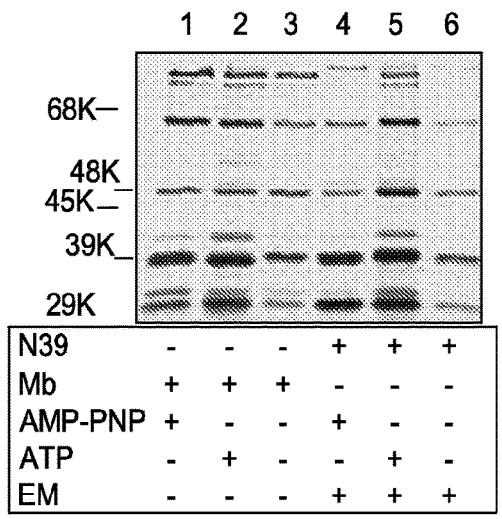
FIGS. 14A-14C.
Figure 14B:
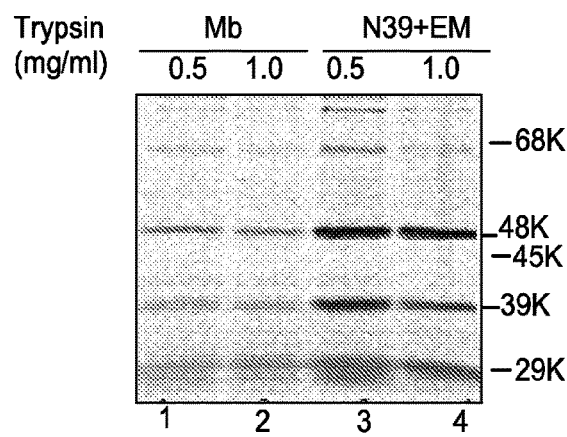

In contrast, liposomes comprised of phospholipid mixtures induced the formation of two specific domains (FIG. 10A, lanes 9, 10); one at M48 starting at 361EGVQIQN (SEQ ID NO:6), and the other at 39-kDa. The domains were mixtures of N-terminal fragments (Table 3). These were similar to the domains of the membrane-specific SecAM form. The other 68-kDa and the smaller 27-30-kDa fragments (FIG. 10A, lanes 9, 10) were probably integral to the SecAS form, as they were similar to those derived from the cytosolic form of SecA (FIG. 10A, lanes 3, 4). The 39-kDa mixtures could be derived from either SecAM or SecAS. The specificity of phospholipids to the formation of the lipid-specific M48 and N39 domains (as defined by the presence of trypsin-resistant fragments) was determined. The presence of phosphatidyl-choline (PC) had little effect (FIG. 10B, lanes 3, 4), and phosphatidylethanolamine (PE) alone had only a slight effect (lanes 7, 8), producing a minor M48 band (FIG. 10C, lane 2). PE alone did not form liposomes. This suggests that the effect of phospholipids on forming trypsin resistant bands may be subject to binding. The major anionic phospholipids, phosphatidlyglycerol (PG) and cardiolipin (CL) alone not only failed to promote the formation of lipid-specific M48 and N39 domains, but also induced SecA to adopt a conformation that was even more susceptible to trypsin digestion (FIG. 10B, lanes 9-12), even though anionic phospholipids are necessary for SecA to function. Since *E. coli* membrane phospholipids consist of 25-30% anionic lipids (PG and CL) and 70-75% PE, the effects of phospholipid mixtures were determined at PE:PG or PE:CL ratios of 3:1 to mimic the physiological ratios of phospholipids. Both combinations promoted the conformational changes to form the lipid-specific domains similar to the *E. coli* phospholipid mixtures (FIG. 10D). While PC could replace PE in these combinations (FIG. 5E, lanes 9-12), PC/PE mixtures could not (FIGS. 10D & 10E). These data indicate that the formation of phospholipid-bilayer liposomes using anionic phospholipids, PG and CL, in combination with PE or PC (in proportional amounts similar to *E. coli* phospholipid membrane mixtures) promote conformational changes in SecA that induce the formation of the lipid-specific domains of M48 and N39. As previously reported, ATP or AMP-PCP had no significant effect on the formation of these membrane-specific domains (data not shown, but see FIG. 14 for characterization of the protease-resistant domains from membrane or EM-associated SecA). All subsequent work was, therefore, carried out using liposomes consisting of *E. coli* phospholipid mixtures (CL:PG:PE ratio about 10:20:70) in the absence of nucleotides.

TABLE 3

| SecA fragment | SecA + liposome | SEQ ID NO | SecA − liposome | SEQ ID NO | N95 + liposome |
|---|---|---|---|---|---|
| 39 kDa | 1MLIKLLTK (80%) | 7 | | | 1MLIKLLtK (44%) |
| | 9VFGSRnDR (20%) | 8 | | | 9VfGSRNDR (39%) |
| | | | | | 14NDRtLRRM (17%) |
| 48 kDa | 361EGVQIQNE | 9 | | | |
| 50 kDa | | | 9VFGSRNDR | 8 | |

Figure 11A:
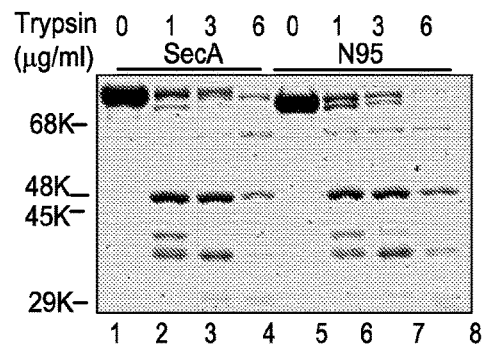
FIGS. 11A-11D are photographs of electrophoresis gels showing proteolysis of SecA and the N95 construct (FIG. 11A), soluble SecA and the N95 construct (FIG. 11B), EM-associated N95 and C95 constructs (FIG. 11C) and soluble N95 and C95 constructs (FIG. 11D), carried out in the presence of EM with indicated concentrations of trypsin. Lanes 1-8 are indicated (bottom) and molecular weight markers are indicated (left).

Amino acid (aa) sequence analysis of *E. coli* SecA fragments. *E. coli* SecA (EcSecA) fragments (FIG. 10A, lanes 3 for 50-kDa, lanes 9 for 39-kDa and 48-kDa; FIG. 11A, lane 2 for 39-kDa with N95) were subjected to peptide sequencing analysis. Identified SecA sequences were shown in single letter code. Upper case letters represent amino acids of the analyzed sequences which match the known EcSecA sequence, whereas lower case letters represent unconfirmed residues.

Example 9: The N-Terminal Residues, not the C-Terminus of SecA are Required for the Formation of Lipid Specific Domains Materials and Methods
Proteolysis Patterns of Soluble and Lipids-Associated SecA and SecA Variants The proteolysis patterns of soluble and lipid associated N95 and C95 were analyzed as described above, except that SecA and N95 were denatured in 8 M urea and renatured as with C95 by dialysis in DTK buffer, then proteolysis was carried out as described above.

Results

Figure 11B:
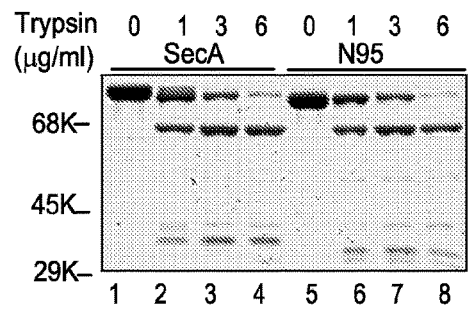
Figure 11C:
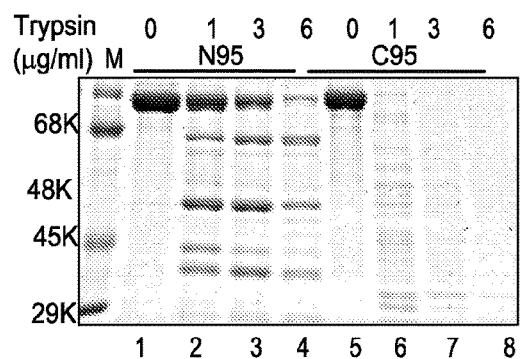
Figure 11D:
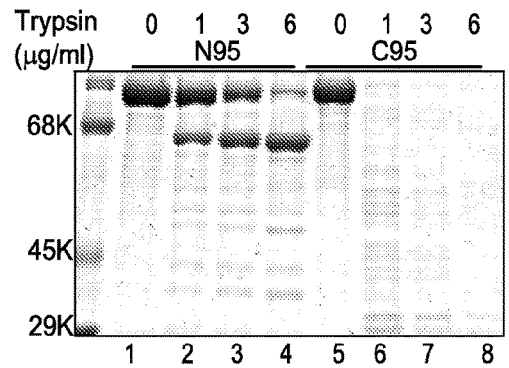

The lipid-specific M48 domain lies in the middle of the 901 residues of SecA-starting at Glu 361 and presumably ending at Arg805 (Table 3). Of the potential membrane-interacting domains of SecA, one domain lies at the N-terminus, while the other domains lie at the C-terminus where they have been shown to interact with SecB and lipids. Therefore, the possible roles of the two extreme termini in the formation of lipid-specific domains were examined. Two SecA deletion variants, C95 (residues 64-901) and N95 (residues 1-831) that have the potential to form the M48 fragment (residues 361-805), were purified and examined for their interactions with E. coli phospholipid liposomes. N95, which lacks the last 70 residues of the C-terminal lipid interacting domain, could generate the lipid specific M48 (FIG. 11A) and N39 N-terminal mixtures (Table 3), while C95, which lacks the N-terminal 63 residues, could not (FIG. 11C). Indeed, the C95 SecA variant showed quite different proteolytic sensitivity and profile from that of either N95 or SecA in the presence or absence of liposomes (FIGS. 11B-D). These data show that the N-terminal 63 amino acid residues, but not the C-terminal 70 residues, are critical for the formation of SecA domains, including specific interaction with phospholipids. These results correspond well with in vivo and in vitro translocation activity that N95 is found to possess, but that C95 does not. The N-terminal residues of SecA play a critical role in preprotein binding. It is, therefore, reasonable to assume that the formation of lipid-specific domains is dependent on the N-terminal residues of SecA.

Example 10: Membrane Proteins, not Necessarily SecYEG, Stabilize the Lipid-Specific Domains of SecA in Liposomes Results Even though E. coli phospholipid liposomes induce conformational changes in SecA to form the M48 and N39 domains, the greater sensitivity of these domains to trypsin at concentrations higher than 10 μg/ml (FIGS. 10 and 11) suggests that other factors, such as interactions of SecA with other membrane proteins, are involved in the resistance of these domains to high concentrations of trypsin (up to 1 mg/ml) when they are embedded in E. coli membranes. The proteolytic profiles of liposome- and membrane-associated SecA constructs were further examined. SecA (10 μg) was mixed with either liposomes (20 μg) or SecA-depleted BA13 membranes (20 μg lipids) on ice with trypsin for 15 minutes. Though their proteolytic profiles appear to be similar, the lipid-specific M48 and N39 domains of liposome-associated SecA were not very stable when treated with 30 μg/ml of trypsin. This is in contrast to the stable domains within similarly treated membrane-associated SecA (see FIG. 12A, lanes 4, 8; FIG. 12 demonstrates proteolysis of membrane-integrated SecA and various phospholipid-integrated SecA with trypsin). To mimic conditions where active protein translocation takes place, and to provide the necessary sensitivity for detection, radioactive-labeled SecA was used (1 μg SecA/20 μg membrane proteins) to examine the proteolytic profiles of SecA. Under these conditions, the lipid-specific M48 and N39 domains in liposome-associated SecA were more sensitive to trypsin digestion on ice than in membrane-associated SecA; complete digestion was observed at 10 μg/ml of trypsin treatment with the former, but not the latter (FIGS. 12B-C). The temperature-dependent protease sensitivity of these domains appeared to be related to the SecA-to-liposomes ratio and their interactions at 37° C. (FIG. 12D). Therefore, all subsequent trypsin treatments were carried out on ice. These results again indicate that the lipid-specific M48 and N39 domains of SecA are less stable at 37° C. than their membrane associated counterparts, and that some other membrane proteins may be involved in the stability of these lipid-specific SecA domains.

Figure 13A:
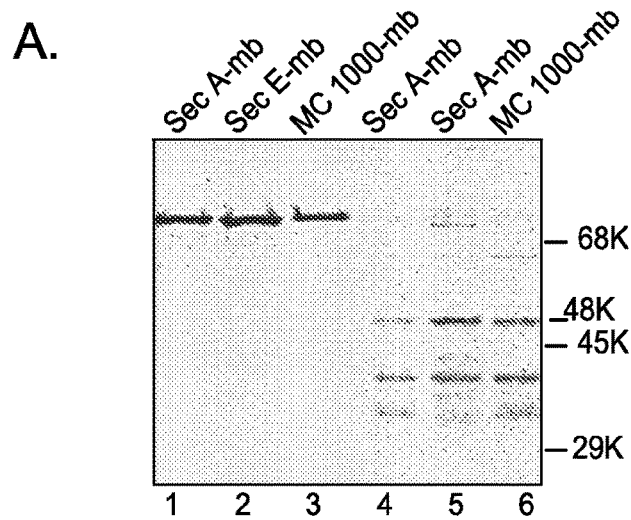
FIGS. 13A-13C.

SecYEG complexes have been shown to bind SecA with high-affinity. Therefore, SecYEG complexes are logical candidates to stabilize the SecA domains in the membrane. To determine whether SecYEG is essentially required for the stability of SecA lipid-specific domains, SecE-depleted membranes that contained no detectable SecE or SecY and little SecG (<1% of wild-type MC1000 membranes) as determined immunologically were employed. The SecYEG depleted membranes stabilized the M48 and N39 domains (1 μg of radioactive SecA) as well as wild type membranes or SecA-depleted BA13 membranes (FIG. 13A, lanes 4-6). FIG. 13 demonstrates that SecYEG are not required for the formation of M48. In the SecYEG-depleted membranes, SecA was overproduced approximately 5-6 fold. As a result, the amounts of SecA and SecYEG in the membrane are not directly related to the stability of lipid-specific domains.

Figure 13B:
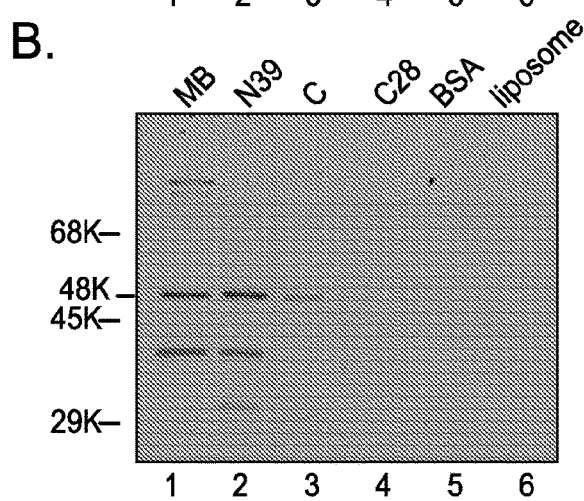
Figure 13C:
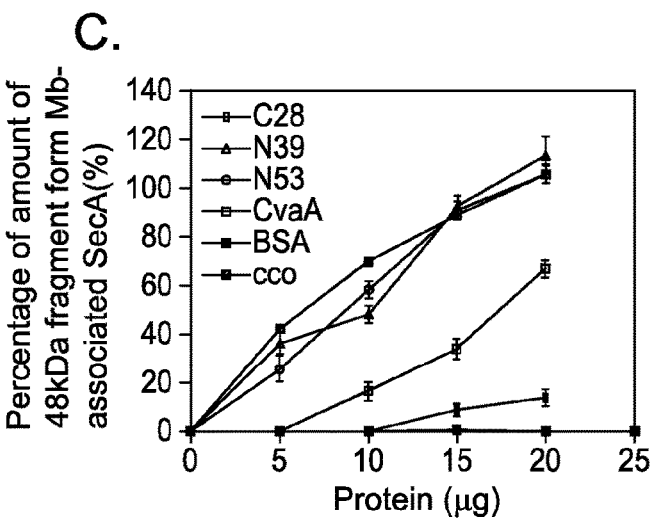

The major difference between liposomes and membranes with the same amount of phospholipids is the presence of equal amounts of proteins in the membrane. Therefore, whether the addition of proteins to liposomes mimics the enhancement in the stability of SecA domains in the membrane was examined. The addition of soluble bovine serum albumin (FIG. 13C) or cytochrome C had no stabilizing effect (FIG. 13B, lane 3), even though the latter binds loosely to liposomes (at 20 μg). Several fragments of SecA including the N39 (SecA1-350), N53 (SecA1-462), M48* (SecA344-810) as well as C28 (SecA662-901) were cloned, purified and tested. The purified N-terminal N39 and N53 fragments integrated into the liposomes and stabilized the formation of the radio-labeled tryptic M48 and N39 domains to the same extent as membranes, while C-terminal C28 had little effect (FIG. 13B). Such stabilizing effects were dependent on the protein concentration for the interaction of liposomes and SecA (FIG. 13C). To examine whether the stabilizing factor is restricted to N-terminal SecA fragments, an unrelated purified membrane protein, CvaA, which is a component of ABC transporter for colicin V, was used (FIG. 13C). Addition of a membrane protein CvaA did indeed stabilize the lipid-specific M48 (FIG. 13C) and N39 domains (data not shown) in a concentration-dependent manner, though it was not as effective as the addition of N39 or N53 SecA fragments (FIG. 13C). In addition, the presence of another unrelated membrane protein complex, cytochrome C oxidase complex also showed effective protection of stability (FIG. 13C). These results indicate that SecYEG complexes are not essential for stabilizing trypsin-resistant SecA domains in membranes as N-terminal domains of SecA are equally as effective, and even unrelated membrane proteins can also stabilize these lipid-specific domains, albeit with varying degrees of efficiency.

Example 11: Properties of Phospholipid-Specific Domains

Results

To determine whether the domains induced by proteoliposomes behave differently from those induced by membranes, the effects of ATP and its non hydrolyzable analog AMP-PCP on the protein's resistance to high concentration of trypsin in both proteoliposomes and membranes were examined. The presence of either nucleotide had little effect on the formation of M48 and N39 domains (FIG. 14A), indicating that the Walker binding sites are not critical for the stability for these lipid-specific domains. These domains were similarly resistant to trypsin treatment even up to concentrations as high as 1 mg/ml (FIG. 14B), as found previously. Moreover, the use of heparin to disrupt the ionic interaction of SecA with phospholipids had no effect, and $Na_2CO_3$ extraction after trypsin treatment also proved to be similar for the domains in proteoliposomes and in membranes (Table 4). Thus, the N68 and N39 domains could not be extracted by $Na_2CO_3$, indicating the integral nature of their association with liposomes and membranes (even though N68 is soluble without lipids) while the M48 domain was seen to be partially extracted (about 50%), indicating that it is in a more aqueous environment; as reported earlier under conditions of protein translocation.

To determine whether the formation of these domains and their resistance to trypsin were due to the intrinsic resistance of these domains or due to some protection conferred from being formed in the presence of proteoliposomes or membranes, detergents were added after the formation of SecA domains. The non-ionic detergents, Triton X-100 and maltododecylmaltoside, which have previously been shown to maintain SecYEG in soluble form and to allow the formation of an inserted 30-kDa SecA domain, were used. Neither conferred the subsequent protection to trypsin digestion, indicating that the M48 and N39 domains are specifically induced and maintained only in the presence of phospholipids.

Example 12: Structures of Lipid-Specific Domains as Observed by Atomic Force Microscopy (AFM)

Methods and Materials
Atomic Force Microscopy (AFM)

AFM images were obtained with a CP-Autoprobe (Park Scientific, Sunnyvale, Calif.) and a Multimode V scanning atomic force microscope (Veeco) by using the noncontact mode as previously described [14]. Briefly, SecA and SecA derivatives were mixed by vortexing for at least 20 seconds with TKM buffer (10 mM Tris-HCl, pH 8.0, 50 mM KCl and 2 mM $MgCl_2$) in the presence or absence of liposomes prepared from E. coli total lipid mixtures and incubated in an ice bath for 10 min before being applied onto the freshly calved mica. Samples were incubated at room temperature in a covered dish, rinsed by deionized water for 4 times, and dried in a desiccator until used.

Results

Figure 15A:
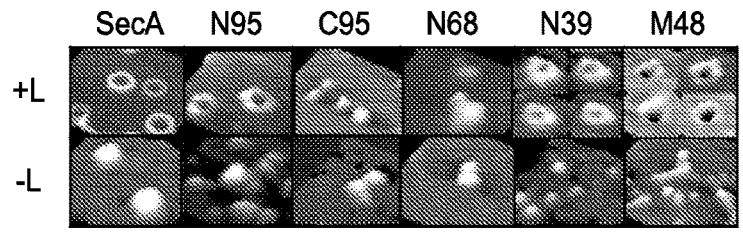
FIGS. 15A-15C.

The ability of SecA to form ring-like pore structures upon its interaction with phospholipids using both electron microscopy and atomic force microscopy has been demonstrated. Here AFM was the tool of choice to probe overt conformational changes of the SecA domains that could be induced by phospholipids. In agreement with limited proteolysis results, N95 but not C95 (lacking the first 63 N-terminal residues) formed a ring-like structure similar to those formed by wild-type SecA in the presence of phospholipids (FIG. 15A). FIG. 15A shows AFM images of SecA and its domains suggesting a model of a SecA channel for protein secretion.

These results further support the conclusion that the N-terminal, but not the C-terminal, of SecA is required for the formation of lipid specific domains. The structure of various SecA domains in lipids was examined. The lipid-specific domains of N39 and M48*, as well as the soluble domain of N68 were cloned, overexpressed, and purified. The lipid-specific domains of N39 and M48* formed imperfect partial ring structures, which appeared to be smaller than those of the intact SecA, while the soluble N68 domain (FIG. 15A) and C34 failed to form any ring structure at all (not shown). All ring structures that were observed were only formed in

TABLE 4

|  | Membrane (%) | | | Liposomes (%) | | | Liposomes + N39 (%) | | |
| --- | --- | --- | --- | --- | --- | --- | --- | --- | --- |
|  | TK | $Na_2CO_3$ | Heparin | TK | $Na_2CO_3$ | Heparin | TK | $Na_2CO_3$ | Heparin |
| SecA | 100 | 123 ± 7.2 | 68 ± 12 | 100 | 130 ± 9.5 | 81 ± 33 | 100 | 115 ± 12 | 95 ± 34 |
| 68 kDa | 100 | 113 ± 10 | 92 ± 23 | 100 | 128 ± 7.8 | 88 ± 31 | 100 | 110 ± 25 | 75 ± 23 |
| 48 kDa | 100 | 36 ± 4 | 102 ± 19 | 100 | 42 ± 8.3 | 100 ± 33 | 100 | 50 ± 20 | 106 ± 34 |
| 39 kDa | 100 | 101 ± 13 | 100 ± 28 | 100 | 130 ± 25 | 80 ± 36 | 100 | 100 ± 17 | 68 ± 9.3 |

Figure 14C:
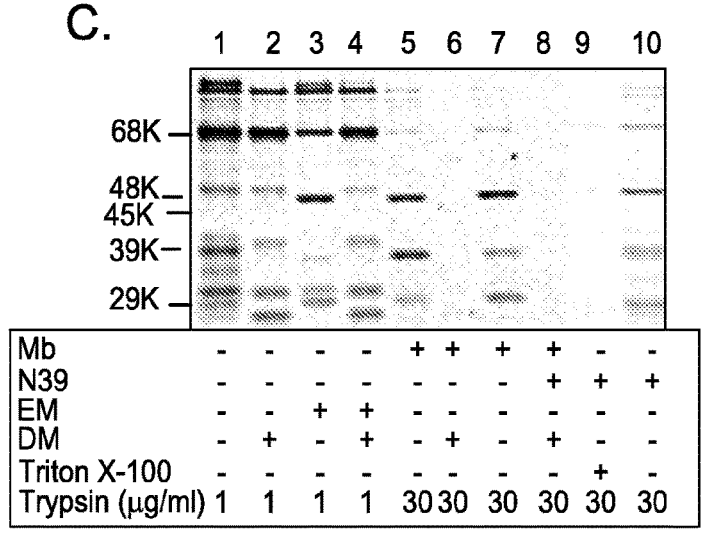
Figure 15B:
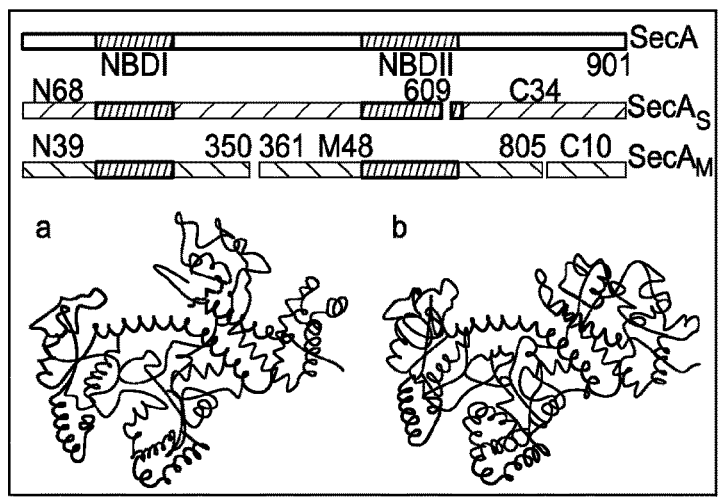

Reaction mixtures with 1 μg [$^{35}$S]SecA were incubated and treated as in FIG. 14C. The membranes, liposomes and liposomes with N39 (20 μg/ml) and were recovered by centrifugation and re-suspended in 100 μl of TK buffer, 10 mg/ml heparin or 0.1 M $Na_2CO_3$ (pH 11) respectively. After incubation on ice for 30 min, the liposomes and membranes were recovered by centrifugation and were analyzed by SDS-PAGE and autoradiography. The quantities of remaining SecA fragments in liposomes and membranes were determined by Quantity One software, using these in TK buffer as 100%. All experiments were carried out for 3-5 times.

the presence of phospholipid liposomes with no detergents and did not form in the absence of lipids. The N39 ring structure differed from that formed by the M48* domain in that the former appeared to be more anchored on the surface of the lipids, whereas the partial M48 ring structures showed a much more deeply indented cavity at the center of the ring structure (FIG. 15B). These data suggest that the lipid-specific domains of N39 and M48* do form part of the characteristic ring-like pore structures of SecA following its interaction with phospholipids, and further suggest that these lipid-specific domains are important components of SecA function in the membrane. It is interesting to note that N39 forms partial ring structures while the larger N68 did not, indicating the dynamic nature of the formation and maintenance of these domain structures.

Discussion of Results from Examples 8-12

Figure 15C:
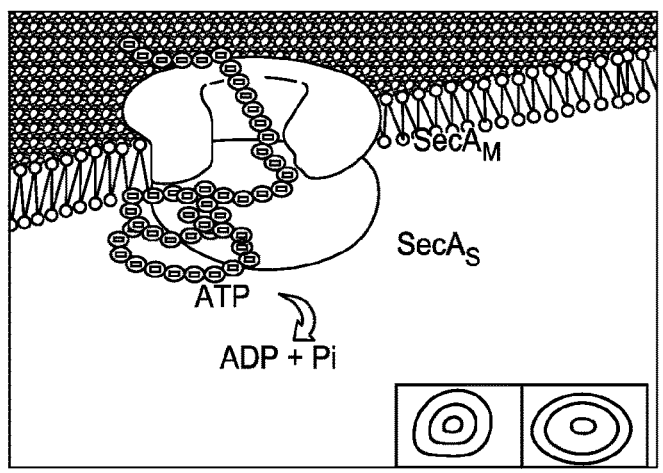

SecA forms ring-like structure upon interaction with *E. coli* phospholipids and SecA alone can promote protein translocation in liposomes and elicit ion-channel activity. In addition, dimeric SecA couples the preprotein translocation in an asymmetric manner. This study has demonstrated that SecA, in the presence of liposomes, forms the lipid-specific domains of N39 and M48, with characteristics similar to the membrane-specific domains, in addition to the N68 and C34 domains present in the soluble SecA and membrane SecAS forms. From X-ray structures of soluble *E. coli* SecA, the most likely tryptic cleavage site in SecAS that gives rise to N68 and C34 is 608-609RK, which is in a loop at the surface of the protein and probably lies within the Walker B motif of the NBDII region (FIG. 15B). As a result of the drastic conformational change with lipids, the cleavage sites for SecAM that give rise to N39 and M48 are probably at 348R in the PBD domain, and 805R in the an α-helix in IRA1 domain (FIG. 15B). To account for these observations, a model (FIG. 15C) in which the SecA dimer alone functions as the protein conducting-channel in promoting protein translocation and ion channel activity is proposed. In this model SecA adopts an asymmetric dimer configuration in the membrane, in which the membrane bound subunit SecAM is specific for membrane lipids and plays the structural role of a channel, while the other SecA subunit, SecAS, has essentially the same conformation as it does in its soluble form and functions as the ATPase motor.

SecA$_S$ has both the ATPase domain of N68 and the regulatory C34 domain, while SecA$_M$ is structurally composed of the N39 domain forming the surface part of the ring-pore structure and the M48 domain forming the more aqueous part of the channel (FIG. 15C), as well as a small C10 domain that is probably exposed to the periplasmic side. In their lipid dependent structural configuration, neither N39 nor M48 exhibit ATPase activity (data not shown), even though each possesses an adequate nucleotide binding domain (NBDI and NBDII, respectively) with each domain encompassing an intact Walker A and B sites (FIG. 15B). In this model for SecA-dependent protein translocation, SecA$_S$ alone would provide the ATPase activity that is capable of propelling the protein precursor(s) through the SecA$_M$ channel. While the proposed model depicted in FIG. 15C indicates a clear distinction between the two asymmetric units of the liposome-induced SecA dimer, it is not entirely inconsistent with the possibility of each subunit "flip-flopping" between each other conformation as the protein that is being translocated is propelled into the periplasmic space.

Example 13: Validation of Methods for Screening of Rose Bengal Analogs as SecA Inhibitors Materials and Methods
Bacterial Strain and Growth Conditions An outer membrane leaky mutant strain, *E. coli* NR698 (Ruiz et al., Cell, 2005, 121:307-317; provided by Thomas J Silhavy of Princeton University) and *B. subtilis* 168 (lab stock) were grown in Luria-Bertani (LB) medium at 37° C.
Protein Preparation EcSecAN68, a truncated mutant of EcSecA containing the N-terminal catalytic domain, EcSecA, and BsSecA were used to study the in vitro inhibition effect of RB analogs. These proteins were purified as previously described (Chen et al., *J. Biol. Chem.* 1996, 271:29698-29706; Chen et al., *J. Bacteriol.* 1998, 180:527-537).
In Vitro ATPase Activity Assay To evaluate the inhibitory effect of synthesized rose bengal ("RB") analogs (Table 5), EcSecA N68 was used for the initial enzymatic ATPase screening assay. EcSecA N68 is a truncated protein of *E. coli* SecA that lacks the down regulatory C-terminus, which allosterically inhibit the ATPase activity, and is the best SecA protein for screening a large number of compounds as described previously (Chen et al., *Bioorg Med Chem* 2010, 18(4), 1617-1625; Huang et al., *ChemMedChem* 2012, 7(4), 571-577). The initial screening was conducted at 100 µM.

The malachite green colorimetric assay was used to determine the inhibition effect of RB analogs against the ATPase activity of SecA proteins. In this assay, ATPase assays were carried out at different concentrations of the inhibitor, and IC$_{50}$ was defined as the concentration of the compound, which could inhibit 50% ATPase activity of the enzyme. Because RB analogs were dissolved in 100% DMSO, there was 5% DMSO in the final assay.
SecA-Liposomes Ion-Channel Activity Assays in the Oocytes Analogs that showed substantial inhibition in the initial screening were evaluated in the channel activity assay using both EcSecA and BsSecA. This is a semi-physiological assay in the oocytes (Hsieh et al., *J. Biol. Chem.* 2011, 286, 44702-44709; Lin et al., *J. Membr. Biol.* 2006, 214, 103-113; Lin et al., *J. Membr. Biol.* 2012, 245, 747-757) developed to measure SecA-mediated protein-channel activity in a liposome environment, which closely mimics the situation in bacteria. This method serves as an excellent confirmative assay and is used for the generation of quantitative data for SAR work.

The liposomes were prepared as described previously (Hsieh et al., *J. Biol. Chem.* 2011, 286, 44702-44709; Lin et al., *J. Membr. Biol.* 2006, 214, 103-113; Lin et al., *J. Membr. Biol.* 2012, 245, 747-757). *E. coli* total lipids (Avanti) were dried, re-suspended in 150 mM KCl, and sonicated in an ice water bath until the solution became clear (usually for 3-5 mins). Samples of the liposomes were stored at –80° C. and thawed only once before use. Oocytes were obtained from live frog *Xenopus laevis* (Xenopus Express, Inc) and injected with sample mixtures as described. 50 nl of the sample mixtures were injected into dark pole site of oocytes using Nanoject II injector (Drummond Scientific Co., Broomall, Pa.). The ion current was recorded three hours after injection. The amount for each component is 120 ng liposomes, 120 ng SecA, 14 ng proOmpA, 2 mM ATP, and 1 mM Mg$^{2+}$. The effective concentration of each component in the oocytes was based on the average volume of oocytes of 500 nl.
Results
In Vitro ATPase Activity Assay As can be seen from Table 5, two series of RB analogs, 22a-d and 23a-d showed significant inhibition of enzyme activities. RB analogs containing the 'D-ring' (ring bearing the carbonyl group) and the chloro groups from ring A removed, exhibited substantially reduced activity or essentially no activity. Compounds with these showed no antimicrobial activity against *E. coli* NR698 (MIC: >250 µM) either. Masking the hydroxyl group in 22a-d with a methyl group (21a-d, Table 5) or replacing hydroxyl group with N(CH3)$_2$ (30) also resulted in compounds with weak or no activity.

SecA-Liposomes Ion-Channel Activity Assays in the Oocytes

In the channel activity assay, many compounds showed potent inhibitory activities (Table 6). The potency is about the same against EcSecA and BsSecA with the exception of 22d, which is more potent against EcSecA than BsSecA by about 2-fold. The results suggest that the 9-position of xanthene can tolerate a fairly large degree of modifications including aryl groups and cycloaliphatic and linear aliphatic substitutions. Further, the synthesized new analogs do not need to have a carboxyl group on the group attached to the 9-position to show potency. Such results suggest that the biologically active form of RB is most like the lactone form, not the ring opening with a free caboxylate group. Such cyclization resulting from a Michael addition type of reaction of the quinoid moiety is well known for this class of compounds including fluorescein. For example, the lactone form is commercially available. Further studies with decarboxylate RB also showed inhibition potency equal or better than RB itself.

The in vitro enzymatic activity and ion-channel activity assays of these analogs do not always parallel that of antimicrobial activities. On one hand, this is not surprising since antimicrobial activities also depend on permeability and solubility, among other factors. For example, the higher molecular weight and the charged carboxylate group of RB could easily impede its membrane permeability and thus lead to reduced antimicrobial activity. Such phenomenon has been observed in other SecA analogs (Chen et al., *Bioorg Med Chem* 2010, 18:1617-1625; Huang et al., *ChemMedChem* 2012, 7:571-577). In addition, the modified RB analogs do not have the same planarity issues as RB and thus may not stack and aggregate as much, which should help improve solubility and consequently permeability.

TABLE 5

Structures of RB analogs

| Comp ID | MW | R | R1 | R2 | R3 | R4 | R5 | R6 |
|---|---|---|---|---|---|---|---|---|
| RB | 1017.6 | chlorinated benzoate | I | I | I | I | NaO | =O |
| 18a | 228.2 | =O | H | H | H | H | OH | OH |
| 18b | 543.8 | =O | Br | Br | Br | Br | OH | OH |
| 18c | 480.0 | =O | H | I | H | H | OH | OH |
| 20a | 308.4 | cyclopentylidene | H | H | H | H | OMe | OMe |
| 20b | 282.3 | propane-2-lidene | H | H | H | H | OMe | OMe |
| 21a | 310.4 | cyclopentane | H | H | H | H | OMe | OMe |
| 21b | 284.4 | iso-propyl | H | H | H | H | OMe | OMe |
| 21c | 326.4 | n-hexyl | H | H | H | H | OMe | OMe |
| 21d | 324.4 | cyclohexane | H | H | H | H | OMe | OMe |
| 22a | 282.3 | cyclopentyl | H | H | H | H | OH | OH |
| 22b | 256.3 | iso-propyl | H | H | H | H | OH | OH |
| 22c | 298.2 | n-hexyl | H | H | H | H | OH | OH |
| 22d | 296.2 | cyclohexyl | H | H | H | H | OH | OH |
| 23a | 597.9 | cyclopentyl | Br | Br | Br | Br | OH | OH |
| 23b | 785.9 | cyclopentyl | I | I | I | I | OH | OH |
| 23c | 660.0 | cyclopentyl | I | I | H | I | OH | OH |
| 23d | 759.9 | iso-propyl | I | I | I | I | OH | OH |
| 30 | 336.1 | cyclopentyl | H | H | H | H | NMe$_2$ | NMe$_2$ |

TABLE 6

Biological activities of RB analogs

| Comp ID | MW | Ion channel, IC$_{50}$ (μM) | | MIC (μM) | |
|---|---|---|---|---|---|
| | | EcSecA | BsSecA | *E. coli* NR698 | *B. subtilis* 168 |
| RB | 1017.6 | 0.4 | 0.3 | 5 | 100 |
| 22a | 282.3 | 3.4 | 3.0 | 45 | 25 |
| 22b | 256.3 | 4.3 | 4.9 | 90 | 75 |
| 22c | 298.2 | 2.3 | 2.5 | 19 | 13 |
| 22d | 296.3 | 2.8 | 6.6 | 25 | 22 |
| 23a | 597.9 | 2.3 | 2.4 | 2 | 22 |
| 23b | 785.9 | 2.5 | 3.8 | 1 | 6 |
| 23c | 660.0 | 2.2 | 2.8 | 6 | 6 |
| 23d | 759.9 | 2.8 | 2.5 | 4 | 6 |

REFERENCES

1. Gundersen, C. B., Miledi, R. & Parker, I. Messenger RNA from human brain induces drug- and voltage-operated channels in *Xenopus* oocytes. Nature 308, 421-424 (1984).
2. Miledi, R., Parker, I. & Sumikawa, K. Properties of acetylcholine receptors translated by cat muscle mRNA in *Xenopus* oocytes. Embo J 1, 1307-1312 (1982).
3. Thornhill, W. B. & Levinson, S. R. Biosynthesis of electroplax sodium channels in Electrophorus electrocytes and *Xenopus* oocytes. Biochemistry 26, 4381-4388 (1987).
4. Lin, B. R., Gierasch, L. M., Jiang, C. & Tai, P. C. Electrophysiological studies in *Xenopus* oocytes for the opening of *Escherichia coli* SecA-dependent protein-conducting channels. J Membr Biol 214, 103-113 (2006).
5. Goldin, A. L. in Expression and Analysis of Recombinant Ion Channels 1-25 (Wiley-VCH Verlag GmbH & Co. KGaA, 2006).
6. Miledi, R., Eusebi, F., Martinez-Torres, A., Palma, E. & Trettel, F. Expression of functional neurotransmitter receptors in *Xenopus* oocytes after injection of human brain membranes. Proceedings of the National Academy of Sciences of the United States of America 99, 13238-13242 (2002).
7. Locke, D. & Harris, A. L. Connexin channels and phospholipids: association and modulation. BMC biology 7, 52 (2009).

8. Fiori, M. C. et al. Permeation of calcium through purified connexin 26 hemichannels. The Journal of biological chemistry 287, 40826-40834 (2012).
9. Oliver, D. B. & Beckwith, J. Identification of a new gene (secA) and gene product involved in the secretion of envelope proteins in *Escherichia coli*. J Bacteriol 150, 686-691 (1982).
10. Hsieh, Y.-h. et al. SecA Alone Can Promote Protein Translocation and Ion Channel Activity. The Journal of biological chemistry 286, 44702-44709 (2011).
11. Hsieh, Y. H. et al. Reconstitution of functionally efficient SecA-dependent protein-conducting channels: transformation of low-affinity SecA-liposome channels to high-affinity SecA-SecYEG-SecDF.YajC channels. Biochem Biophys Res Commun 431, 388-392 (2013).
12. Lill, R., Dowhan, W. & Wickner, W. The ATPase activity of SecA is regulated by acidic phospholipids, SecY, and the leader and mature domains of precursor proteins. Cell 60, 271-280 (1990).
13. Chen, L. & Tai, P. C. ATP is essential for protein translocation into *Escherichia coli* membrane vesicles. Proceedings of the National Academy of Sciences of the United States of America 82, 4384-4388 (1985).
14. Oliver, D. B., Cabelli, R. J., Dolan, K. M. & Jarosik, G. P. Azide-resistant mutants of *Escherichia coli* alter the SecA protein, an azide-sensitive component of the protein export machinery. Proceedings of the National Academy of Sciences of the United States of America 87, 8227-8231 (1990).
15. Huang, Y. J. et al. Fluorescein analogues inhibit SecA ATPase: the first sub-micromolar inhibitor of bacterial protein translocation. ChemMedChem 7, 571-577 (2012).
16. Lin, B. R., Hsieh, Y. H., Jiang, C. & Tai, P. C. *Escherichia coli* Membranes Depleted of SecYEG Elicit SecA-Dependent Ion-Channel Activity but Lose Signal Peptide Specificity. J Membr Biol 245, 747-757 (2012).
17. Silhavy, T. J. & Beckwith, J. Isolation and characterization of mutants of *Escherichia coli* K12 affected in protein localization. Methods Enzymol 97, 11-40 (1983).
18. Gerido, D. A., DeRosa, A. M., Richard, G. & White, T. W. Aberrant hemichannel properties of Cx26 mutations causing skin disease and deafness. Am J Physiol Cell Physiol 293, C337-345 (2007).
19. Sanchez, H. A., Mese, G., Srinivas, M., White, T. W. & Verselis, V. K. Differentially altered Ca2+ regulation and Ca2+ permeability in Cx26 hemichannels formed by the A40V and G45E mutations that cause keratitis ichthyosis deafness syndrome. The Journal of general physiology 136, 47-62 (2010).
20. Le Caherec, F. et al. Incorporation of proteins into (*Xenopus*) oocytes by proteoliposome microinjection: functional characterization of a novel aquaporin. J Cell Sci 109 (Pt 6), 1285-1295 (1996).
21. Celis, J. E. Microinjection of somatic cells with micropipettes: comparison with other transfer techniques. Biochem J 223, 281-291 (1984).
22. Wang, H. W. et al. Ring-like pore structures of SecA: implication for bacterial protein-conducting channels. Proceedings of the National Academy of Sciences of the United States of America 100, 4221-4226 (2003).
23. Cabelli, R. J., Dolan, K. M., Qian, L. P. & Oliver, D. B. Characterization of membrane-associated and soluble states of SecA protein from wild-type and SecA51(TS) mutant strains of *Escherichia coli*. The Journal of biological chemistry 266, 24420-24427 (1991).
24. Chen, X., Brown, T. & Tai, P. C. Identification and characterization of protease-resistant SecA fragments: secA has two membrane-integral forms. J Bacteriol 180, 527-537 (1998).
25. Ramamurthy, V. & Oliver, D. Topology of the integral membrane form of *Escherichia coli* SecA protein reveals multiple periplasmically exposed regions and modulation by ATP binding. The Journal of biological chemistry 272, 23239-23246 (1997).
26. Chen, Y. et al. Molecular interaction and functional regulation of connexin50 gap junctions by calmodulin. Biochem J 435, 711-722 (2011).
27. Peracchia, C. Chemical gating of gap junction channels; roles of calcium, pH and calmodulin. Biochim Biophys Acta 1662, 61-80 (2004).
28. Sotkis, A. et al. Calmodulin colocalizes with connexins and plays a direct role in gap junction channel gating. Cell Commun Adhes 8, 277-281 (2001).
29. Yu, L., Yang, H., Ho, Q. & Tai, P. C. Expression, purification, and characterization of *Pseudomonas aeruginosa* SecA. Protein Expr Purif 50, 179-184 (2006).
30. Chen, X., Xu, H. & Tai, P. C. A significant fraction of functional SecA is permanently embedded in the membrane. SecA cycling on and off the membrane is not essential during protein translocation. The Journal of biological chemistry 271, 29698-29706 (1996)

---

We claim:

1. A method of reconstituting a recombinant protein of interest in the plasma membrane of an oocyte comprising:
   (a) combining the recombinant membrane protein or proteins of interest with a liposome to prepare a proteo-liposome;
   (b) allowing sufficient time for the protein or proteins of interest to fold, associate with, or insert into the liposome's lipid bilayer, and pre-assemble into a functional recombinant membrane protein; and
   (c) introducing the proteo-liposome into the oocyte;
   wherein the recombinant protein or proteins of interest in the proteo-liposome reconstitute in the plasma membrane of the oocyte.

2. The method of claim 1 wherein at least one of the recombinant proteins is a channel, transporter, receptor, cell adhesion molecule, enzyme, or a subunit thereof.

3. The method of claim 1 wherein the recombinant membrane protein or proteins of interest are 2 or more different recombinant proteins that together form a membrane complex or channel.

4. The method of claim 1 wherein (b) is sufficient to allow assembly of the complex or channel in the lipid bilayer of the proteo-liposome.

5. The method of claim 1 wherein the proteo-liposome is introduced into the oocyte by injection.

6. The method of claim 1 wherein the liposome comprises lipids from bacterial extracts.

7. The method of claim 1 wherein the liposome comprises one or more synthetic lipids.

8. The method of claim 1 wherein the liposome comprises phosphatidic acid (phosphatidate) (PA), phosphatidylethanolamine (cephalin) (PE), phosphatidylcholine (lecithin) (PC), phosphatidylserine (PS), cardiolipin, phosphatidylinositol (PI), phosphatidylinositol phosphate (PIP), phosphatidylinositol bisphosphate (PIP2), phosphatidylinositol triphosphate (PIP3), ceramide phosphorylcholine (sphingomyelin) (SPH), ceramide phosphorylethanolamine (sphingomyelin), (Cer-PE) ceramide phosphoryllipid or a combination thereof.

9. The method of claim 8 wherein the liposome comprises a ratio of PC/PS of 2:1.

10. The method of claim 8 wherein the liposome comprises a ratio of PE/PG of 3:1.

11. The method of claim 1 wherein at least one of the recombinant proteins is a connexin.

12. The method of claim 11 wherein the connexin is Cx26.

13. The method of claim 8 wherein the liposome comprises a ratio of PE/PC of 3:1.

14. The method of claim 8 wherein the liposome comprises a ratio of one lipid to another, which is 1:1, 1:2, 1:3, 1:4, 1:5, 1:6, 1:7, 1:8, 1:9, 1:10, or more.

15. The method of claim 1 wherein at least one of the proteins forms a bacterial channel.

16. The method of claim 15 wherein at least one of the proteins is SecA.

17. An oocyte modified according to the method of claim 1.

18. A method comprising subjecting the oocyte of claim 17 to a biochemical or physiological assay, wherein the biochemical or physiological assay detects or measures a structure, function, or activity of the membrane protein or proteins of interest.

19. A method of determining the effect of a lipid microenvironment of a membrane protein or proteins of interest comprising subjecting the oocyte of claim 18 to a biochemical or physiological assay, and comparing the result to a control oocyte having a different lipid microenvironment, wherein the biochemical or physiological assay detects or measures a structure, function, or activity of the membrane protein or proteins of interest, and wherein a difference in the structure, function, or activity of the membrane protein or proteins of interest in the oocyte as compared to the control oocyte indicates an effect of the lipid microenvironment on the membrane protein or proteins of interest.

20. The method of claim 19 comprising assaying two or more oocytes wherein the lipid composition of the proteo-liposomes introduced in the oocytes is different.

21. A method of screening test compounds comprising subjecting the oocyte of claim 17 to a biochemical or physiological assay before and after treatment with a test compound and selecting compounds that increase or decrease the function or activity of the protein or proteins of interest.

22. The method of claim 18 wherein the physiological assay is selected from the group consisting of two-electrode whole cell voltage-clamp, cut-open oocyte voltage-clamp, macropatch clamp, and single channel analysis.

23. The method of claim 18 wherein the protein is a recombinant mutant protein.

24. The method of claim 23 wherein the recombinant mutant protein has a mutation that causes or contributes to a human disease.

25. A proteo-liposome comprising an ion channel-forming recombinant protein and a PC/PS ratio of 2:1 and a PE/PG ratio of 3:1.

26. The method of claim 1, wherein the oocyte is a *Xenopus* oocyte.

27. The method of claim 1, wherein the recombinant protein or proteins of interest reconstituted in the plasma membrane of the oocyte substantially retain their native biological activity.

28. The method of claim 1, wherein introducing the proteo-liposome into the oocyte occurs in the presence of one or more additional factors.

29. The method of claim 28, wherein the one or more additional factors comprise an accessory protein, a membrane protein regulator, an ion chelator, or combinations thereof.

30. The method of claim 1, wherein the liposome comprises two or more different lipids.

31. The method of claim 1, wherein the recombinant protein or proteins of interest in the plasma membrane of the oocyte are functional within minutes after introducing the proteo-liposome into the oocyte.

32. A proteo-liposome comprising an ion channel-forming recombinant protein and a PE/PC ratio of 3:1.

33. An oocyte comprising a functional mammalian or bacterial channel-forming recombinant protein formed by introducing a proteo-liposome comprising the recombinant protein into the oocyte.

34. The oocyte of claim 33 wherein the channel is an ion channel.

35. The oocyte of claim 33 wherein the channel is a protein or peptide channel.

36. The oocyte of claim 33, wherein the channel-forming recombinant protein is reconstituted in the oocyte lipid membrane.

* * * * *

UNITED STATES PATENT AND TRADEMARK OFFICE
CERTIFICATE OF CORRECTION

PATENT NO. : 9,970,945 B2  
APPLICATION NO. : 14/896437  
DATED : May 15, 2018  
INVENTOR(S) : Phang-Cheng Tai et al.

Page 1 of 1

It is certified that error appears in the above-identified patent and that said Letters Patent is hereby corrected as shown below:

In the Claims

Claim 19, Column 56, Line 52, replace "the oocyte of claim 18" with --the oocyte of claim 17--.

Signed and Sealed this
Twenty-third Day of October, 2018

Andrei Iancu
*Director of the United States Patent and Trademark Office*

SEQUENCE LISTING

```
<160> NUMBER OF SEQ ID NOS: 10

<210> SEQ ID NO 1
<211> LENGTH: 28
<212> TYPE: DNA
<213> ORGANISM: Artificial Sequence
<220> FEATURE:
<223> OTHER INFORMATION: Synthetic Primer

<400> SEQUENCE: 1
gctcatatgc agggccgtcg ctggtccg                                28

<210> SEQ ID NO 2
<211> LENGTH: 45
<212> TYPE: DNA
<213> ORGANISM: Artificial Sequence
<220> FEATURE:
<223> OTHER INFORMATION: Synthetic Primer
```

<400> SEQUENCE: 2
ggatccttaa tgatgatgat gatgatgcat ggagaacgat tcacg                45

<210> SEQ ID NO 3
<211> LENGTH: 38
<212> TYPE: DNA
<213> ORGANISM: Artificial Sequence
<220> FEATURE:
<223> OTHER INFORMATION: Synthetic Primer

<400> SEQUENCE: 3
gggaattcca tatgtttcgc catgatgctt tagaaaac                         38

<210> SEQ ID NO 4
<211> LENGTH: 56
<212> TYPE: DNA
<213> ORGANISM: Artificial Sequence
<220> FEATURE:
<223> OTHER INFORMATION: Synthetic Primer

<400> SEQUENCE: 4
ccggaattct taatgatgat gatgatgatg tcattgatcg gtcctgttgc actgtg    56

<210> SEQ ID NO 5
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 5

Val Phe Gly Ser Arg Asn
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 6

Glu Gly Val Gln Ile Gln Asn
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 7

Met Leu Ile Lys Leu Leu Thr Lys
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 8

Val Phe Gly Ser Arg Asn Asp Arg

```
<210> SEQ ID NO 9
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 9

Glu Gly Val Gln Ile Gln Asn Glu
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 10

Asn Asp Arg Thr Leu Arg Arg Met
1               5
```